United States Patent
Picking et al.

(10) Patent No.: US 12,419,942 B2
(45) Date of Patent: *Sep. 23, 2025

(54) **USE OF THE *SALMONELLA* SPP TYPE III SECRETION PROTEINS AS A PROTECTIVE VACCINATION**

(71) Applicants: The Board of Regents for Oklahoma State University, Stillwater, OK (US); University of Kansas, Lawrence, KS (US)

(72) Inventors: Wendy L. Picking, Lawrence, KS (US); William D. Picking, Lawrence, KS (US)

(73) Assignees: University of Kansas, Lawrence, KS (US); The Board of Regents for Oklahoma State University, Stillwater, OK (US)

(*) Notice: Subject to any disclaimer, the term of this patent is extended or adjusted under 35 U.S.C. 154(b) by 227 days.

This patent is subject to a terminal disclaimer.

(21) Appl. No.: 17/938,851

(22) Filed: Oct. 7, 2022

(65) Prior Publication Data

US 2023/0136602 A1    May 4, 2023

Related U.S. Application Data

(63) Continuation of application No. 16/752,802, filed on Jan. 27, 2020, now Pat. No. 11,464,843, which is a continuation of application No. 15/950,735, filed on Apr. 11, 2018, now Pat. No. 10,548,962, which is a continuation-in-part of application No. 15/013,454, filed on Feb. 2, 2016, now Pat. No. 9,950,053, which is a continuation-in-part of application No. 14/437,535, filed as application No. PCT/US2013/066105 on Oct. 22, 2013, now abandoned.

(60) Provisional application No. 61/716,911, filed on Oct. 22, 2012.

(51) Int. Cl.
*A61K 39/112* (2006.01)
*A61K 39/00* (2006.01)

(52) U.S. Cl.
CPC .... *A61K 39/0275* (2013.01); *A61K 2039/543* (2013.01); *A61K 2039/552* (2013.01); *A61K 2039/55505* (2013.01); *A61K 2039/55544* (2013.01); *A61K 2039/55572* (2013.01); *A61K 2039/70* (2013.01); *Y02A 50/30* (2018.01)

(58) Field of Classification Search
CPC .................................................. A61K 39/0275
See application file for complete search history.

(56) References Cited

U.S. PATENT DOCUMENTS

| | | |
|---|---|---|
| 4,982,538 A | 1/1991 | Horstketter |
| 5,034,506 A | 7/1991 | Summerton et al. |
| 5,138,045 A | 8/1992 | Cook et al. |
| 5,168,062 A | 12/1992 | Stinski |
| 5,218,105 A | 6/1993 | Cook et al. |
| 5,258,498 A | 11/1993 | Huston et al. |
| 5,283,187 A | 2/1994 | Aebischer et al. |
| 5,385,839 A | 1/1995 | Stinski |
| 5,459,255 A | 10/1995 | Cook et al. |
| 6,083,486 A | 7/2000 | Weissleder et al. |
| 7,094,410 B2 | 8/2006 | Reisfeld et al. |
| 7,927,870 B2 | 4/2011 | Volkin et al. |
| 8,039,007 B2 | 10/2011 | Rappuoli et al. |
| 9,950,053 B2 | 4/2018 | Picking et al. |
| 10,548,962 B2 | 2/2020 | Picking et al. |
| 11,464,843 B2 * | 10/2022 | Picking .............. A61K 39/0275 |
| 2004/0009191 A1 | 1/2004 | Lowery et al. |
| 2008/0260776 A1 | 10/2008 | Bumann et al. |
| 2013/0149329 A1 | 6/2013 | Picking et al. |
| 2016/0220655 A1 | 8/2016 | Picking et al. |

FOREIGN PATENT DOCUMENTS

| | | |
|---|---|---|
| WO | WO9522618 | 8/1995 |
| WO | WO199718225 | 5/1997 |
| WO | WO200059537 | 10/2000 |
| WO | WO2002088346 | 11/2002 |

OTHER PUBLICATIONS

Felgner, P. et al, "Lipofection: a highly efficient, lipid-mediated DNA-transfection procedure", Proc. Natl. Acad. Sci., USA, vol. 84, pp. 7413-7417, (Nov. 1987).
Malone, R. el al, "Cationic liposome-mediated RNA transfection", Proc. Natl. Acad. Sci., USA, vol. 86, pp. 6077-6081, (Aug. 1989).
Leventis, R. et al, "Interactions of mammalian cells with lipid dispersions containing novel metabolizable cationic amphiphiles", Biochim. Biophys. Acta, vol. 1023(1), pp. 124-132, (Mar. 1990).
Behr, J. et al, "Efficient gene transfer into mammalian primary endocrine cells with lipopolyamine-coated DNA", Proc. Natl. Acad. Sci., USA, vol. 86, pp. 6982-6986, (Sep. 1989).
Medina, E. et al, "Pathogenicity island 2 mutants of *Salmonella typhimurium* are efficient carriers for heterologous antigens and enable modulation of immune responses", Infection and Immunity, vol. 67(3), pp. 1093-1099, Mar. 1, 1999.
Oberhauser, B. et al, "Effective incorporation of 2'-O-methyl oligoribonucleotides into liposomes and enhanced cell association through modification and thiocholesterol", Nucl. Acids Res, vol. 20(3), pp. 533-538, (1992).
Kabanov, A. et al, "A new class of antivirals: antisense oligonucleotides combined with a hydrophobic substituent effectively inhibit virus reproduction and synthesis of virus-specific proteins in MDCK cells", FEBS Lett., vol. 259(2), pp. 327-330, (Jan. 1990).

(Continued)

*Primary Examiner* — Brian Gangle
*Assistant Examiner* — Lakia J Jackson-Tongue
(74) *Attorney, Agent, or Firm* — Meunier Carlin & Curfman LLC

(57) ABSTRACT

Antigenic molecules and compositions described herein protect against infection by typhoidal and non-typhoidal *Salmonella* serovars. Methods of immunization comprise the use of the antigenic molecules.

4 Claims, 19 Drawing Sheets

Specification includes a Sequence Listing.

(56) References Cited

OTHER PUBLICATIONS

O'Garra, A., "Cytokines induce the development of functionally heterogeneous T helper cell subsets", Immunity, vol. 8, pp. 275-283, (Mar. 1998).
Saison-Behmoaras, T. et al, "Short modified antisense olionucleotides directed against Ha-ras point mutation induce selective cleavage of the nMRA and inhibit T24 cells proliferation", EMBO J., vol. 10(5), pp. 1111-1118, (May 1991).
Pollard, H. et al, "Polyethylenimine but not cationic lipids promotes transgene delivery to the nucleus in mammalian cells", J. Biol. Chem., vol. 273(13), pp. 7507-7511, (Mar. 1998).
Krumlauf, R. et al, "Developmental regulation of alpha-fetoprotein genes in transgenic mice", Mol. Cell. Biol., vol. 5(7), pp. 1639-1648, (Jul. 1985).
Letsinger, R., "Cholesteryl-conjugated oligonucleotides: synthesis, properties, and activity as inhibitors of replication of human immunodeficiency virus in cell cultures", Proc. Natl. Acad. Sci., USA, vol. 86, pp. 6553-6556, (Sep. 1989).
Shea, R. et al, "Snythesis, hybridization properties and antiviral activity of lipid-oligodeoxynucleotide conjugates", Nucl. Acids Res., vol. 18(13), pp. 3777-3783, (Jun. 1990).
Oppenheim, J. et al, "Prospects for Cytokine and chemokine biotherapy", Clin. Cancer Res., vol. 12(3), pp. 2682-2686, (Dec. 1997).
Henikoff, S. et al, "Amino acid substitution matrices from protein blocks", Proc. Natl. Acad. Sci., USA, vol. 89, pp. 10915-10919, (Nov. 1992).
Chen, Y. et al, "Expression of ssDNA in mammalian cells", BioTechniques, vol. 34(1), pp. 161-171, (Jan. 2003).
Curiel, D. et al, "Adenovirus enhancement of transferrin-polylysine-mediated gene delivery", PNAS, vol. 88(19), pp. 8850-8854, (Oct. 1991).
Geller, A. et al, "An HSV-1 vector expressing tyrosine hydroxylase causes production and release of I-DPOA from cultured rat striatal cells", J. Neurochem., vol. 64(2), pp. 487-496, (Feb. 1995).
Alexander, W. et al, "Expression of the c-myc oncogene under control of an immunoglobulin enhancer in Eu-myc transgenic mice", Mol. Cell. Biol., vol. 7, pp. 1436-1444, (Apr. 1987).
Geller, A. et al, "Infection of cultured central nervous system neurons with a defective herpes simplex virus 1 vector results in stable expression of *Escherichia coli* beta-galactosidase", Proc. Natl. Acad. Sci, USA, vol. 87(3), pp. 1149-1153, (Feb. 1990).
Geller, A. et al, "Long-term increases in neurotransmitter release from neuronal cells expressing a constitutively active adenylate cyclase from a herpes simplex virus type 1 vector", Proc. Natl. Acad. Sci., USA, vol. 90(16), pp. 7603-7607, (1993).
Birket, S. et al, "Preparation and characterization of translocator/chaperone complexes and their component proteins from shigella flexneri", Biochemistry, vol. 46(27), pp. 8128-8137, (Jun. 2007).
Ito, A. et al, "Synthetic Cationic Amphiphiles for liposome-mediated DNA transfection", Biochem. Intl., vol. 22(2), pp. 235-241, (Oct. 1990).
Yang, Y. et al, "Cellular and humoral immune responses to viral antigens create barriers to lung-directed gene therapy with recombinant adenoviruses", J. Virol., vol. 69(4), pp. 2004-2015, (Apr. 1995).
Kaplitt, M. et al, "Long-term gene expression and phenotypic correction using adeno-associated virus vectors in the mammalian brain", Nat. Genet., vol. B(2), pp. 148-154, (Oct. 1994).
Davis, H, et al, "Direct gene transfer into skeletal muscle in vivo: factors affecting efficiency of transfer and stability of expression", Hum Gene Ther, vol. 4(2), pp. 151-159, (1993).
Sambrook, D. et al, "Molecular cloning: a laboratory manual", Cold Spring Harbor Laboratory Press, (1989), Contents for Ch. 1-22, Appendices, and List of tables 34 pages.
Chen, X. et al, "Impact of detergent on biophysical properties and immune response of the IpaDB fusion protein, a candidate subunit vaccine against *Shigella* species", Infect. Immunol., 83:1:292-299, (2015).
Felgner, P. et al, "Cationic liposome-mediated transfection", Bethesda Res. Lab. Focus, vol. 11, pp. 21-25, (1989).
Pinkert, C. et al, "An albumin enhancer located 10 kb upstream functions along with its promoter to direct efficient, liver-specific expression in transgenic mice", Genes and Devel., vol. 1, pp. 268-276, (1987).
Quantin, B. et al, "Adenovirus as an expression vector in muscle cells in vivo", Proc. Natl. Acad. Sci., USA, vol. 89, pp. 2581-2584, (1992).
Stratford-Perricadet, L. et al, "Widespread long-term gene transfer to mouse skeletal muscles and heart", J. Clin. Invest., vol. 90, pp. 626-630, (Aug. 1992).
Choudhari, S. et al, "Studies of the conformational stability of invasion plasmid antigen B from Shigella", Protein Society., vol. 22(5), pp. 666-670, (2013).
Choudhari, S. et al, "Biophysical characterization of the type III secretion tip proteins and the tip proteins attached to bacterium-like particles", J. Pharm. Sci., doi: 10.1002/jps.24047, (Jun. 2014).
Martinez-Becerra, F. et al, "Parenteral immunization with IpaB/IpaD protects mice against lethal pulmonary infection by Shigella", Vaccine, 31(24), pp. 2667-2672, (2013b).
Wagner, M. et al, "Nucleotide sequence of the thymidine kinase gene of herpes simplex virus type 1", Proc. Natl. Acad. Sci., USA, vol. 78(3), pp. 1441-1445, (Mar. 1981).
Mosmann, T. et al, "The expanding universe of T-cell subsets: Th1, Th2 and more", Immunol. Today, vol. 17(3), pp. 138-146, (1996).
Villa-Komaroff, L. et al, "A bacterial clone synthesizing proinsulin", Proc. Natl. Acad. Sci., USA, vol. 75(8), pp. 3727-3731, (Aug. 1978).
Deboer, H. et al, "The tac promoter: a functional hybrid derived from the trp and lac promoters", Proc. Natl. Acad. Sci., USA, vol. 80, pp. 21-25, (Jan. 1983).
Swift, G. et al, "Tissue-specific expression of the rate pancreatic elastase I gene in transgenic mice", Cell, vol. 38, pp. 639-646, (Oct. 1984).
Abbas, A. et al, "Functional diversity of helper T lymphocytes", Nature, vol. 383, p. 787-793, (Oct. 1996).
Shani, M. et al, "Tissue specific and developmentally regulated expression of a Chimeric actin-globin gene in transgenic mice", Molecular and Cellular Biology, vol. 6(7), pp. 2624-2631, (Jul. 1986).
Banchereau, J. et al, "Dentritic cells and the control of immunity", Nature, vol. 392, p. 245-252, (Mar. 1988).
Gebeyehu, G. et al, "Novel biotinylated nucleotide—analogs for labeling and colormetric detection of DNA", Nucleic Acids Research, vol. 15(11), pp. 4513-4534, (1987).
Mason, A. et al, "The hypogonadal mouse: reproductive functions restored by gene therapy", Science, vol. 234, No. 4782, pp. 1372-1378, (Dec. 1986).
Wigler, M. et al, "Transfer of purified herpes virus thymidine kinase gene to cultured mouse cells", Cell, vol. 11, No. 1, pp. 223-232, (1977).
Kelsey, G. et al, "Species- and tissue-specific expression of human alpha1-antitrypsin in transgenic mice", Genes and Devel., vol. 1, pp. 161-171, (1987).
S-J Lee et al, "Identification of a common immune signature in murine and human systemic *Salmonellosis*", PNAS, vol. 109(13), pp. 4998-5003 (Mar. 27, 2012).
Nielsen, P. et al, "Sequence-selective recognition of DNA by strand displacement with a thymine-substituted polyamide", Science, vol. 254, pp. 1497-1500, (Dec. 1991).

* cited by examiner

Figures 10A-B
A.
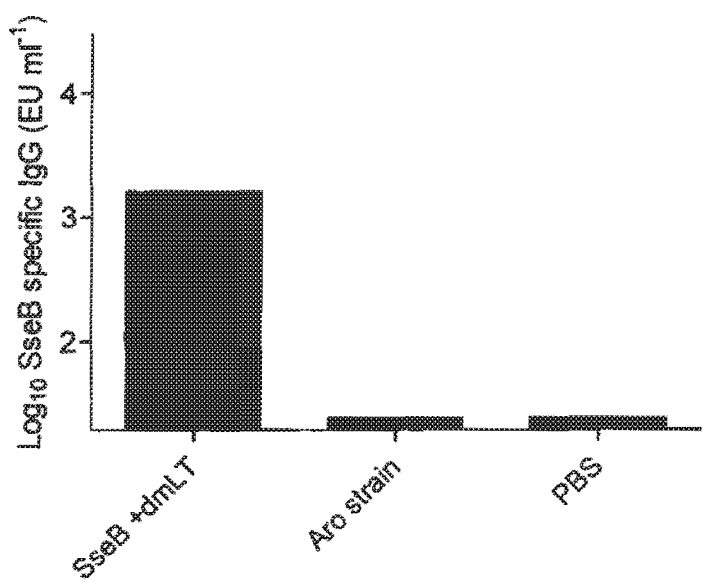
B.
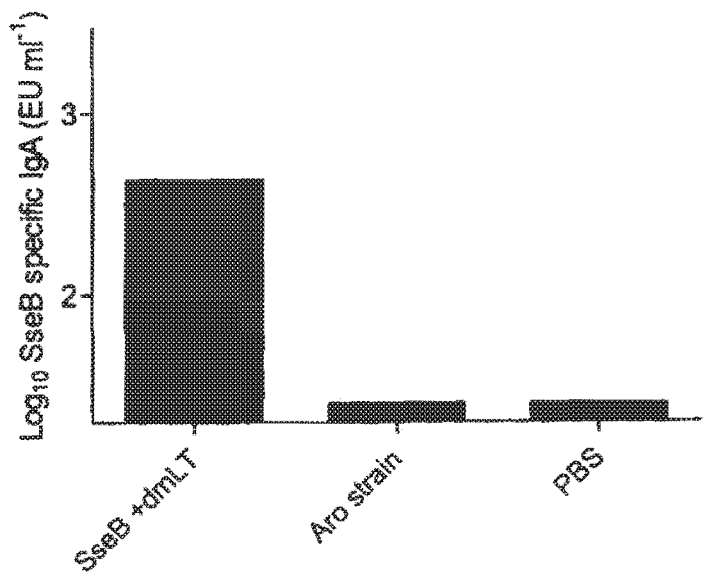

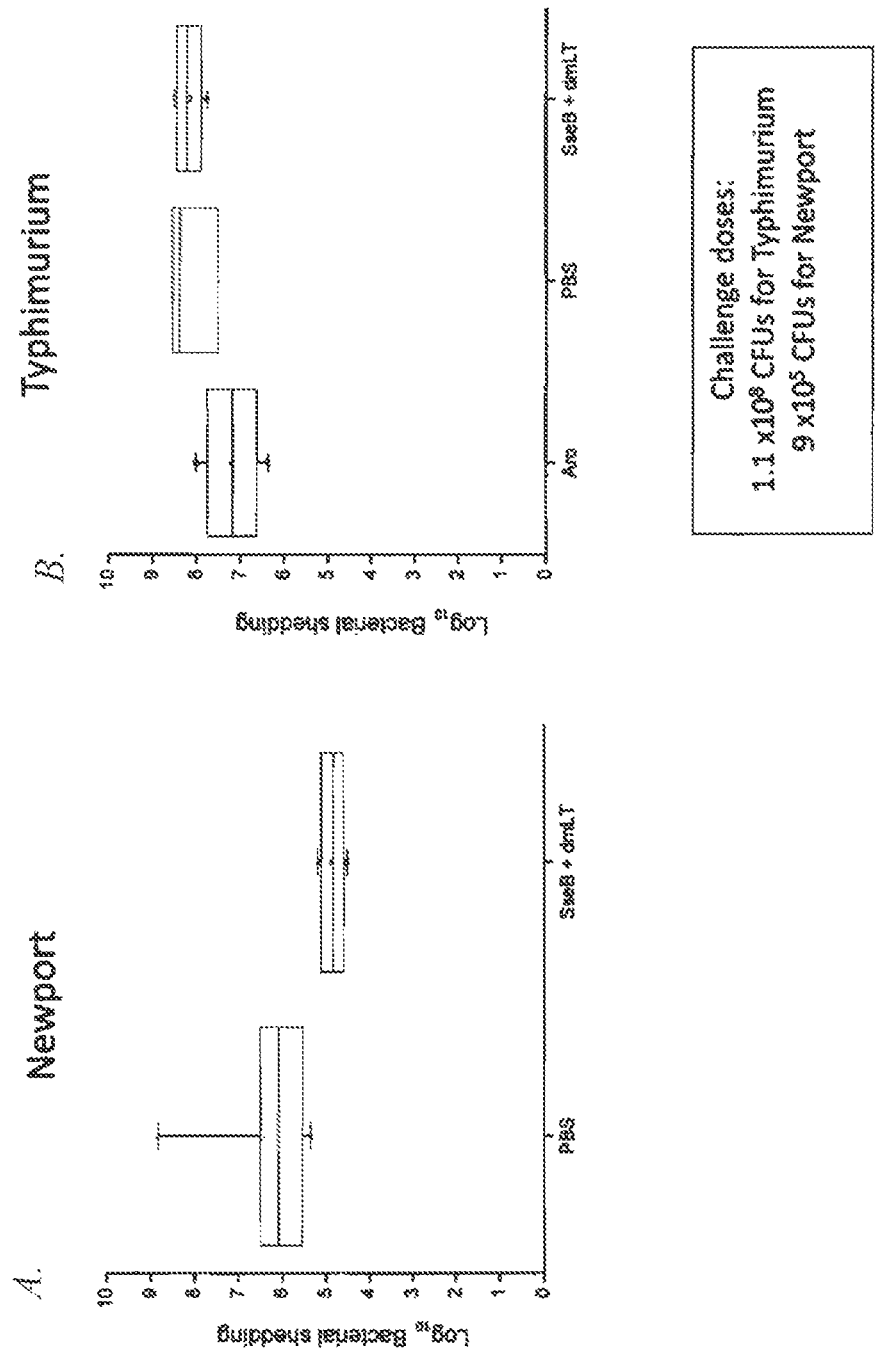
Figures 11A-B

A. MVNDASSISRSGYTQNPRLAEAAFEGVRKNTDFLKAADKAFKDVVATKAGDLKAGTKS
GESAINTVGLKPPTDAAREKLSSEGQLTLLLGKLMTLLGDVSLSQLESRLAVWQAMIES
QKEMGIQVSKEFQTALGEAQEATDLYEASIKKTDTAKSVYDAATKKLTQAQNKLQSLDP
ADPGYAQAEAAVEQAGKEATEAKEALDKATDATVKAGTDAKAKAEKADNILTKFQGTA
NAASQNQVSQGEQDNLSNVARLTMLMAMFIEIVGKNTEESLQNDLALFNALQEGRQAE
MEKKSAEFQEETRKAEETNRIMGCIGKVLGALLTIVSVVAAVFTGGASLALAAVGLAVM
VADEIVKAATGVSFIQQALNPIMEHVLKPLMELIGKAITKALEGLGVDKKTAEMAGSIVGA
IVAAIAMVAVIVVVAVVGKGAAAKLGNALSKMMGETIKKLVPNVLKQLAQNGSKLFTQG
MQRITSGLGNVGSKMGLQTNALSKELVGNTLNKVALGMEVTNTAAQSAGGVAEGVFIK
NASEALADFMLARFAMDQIQQWLKQSVEIFGENQKVTAELQKAMSSAVQQNADASRFI
LRQSRA (SEQ ID NO: 1)

B. ttatgcgcgactctggcgcagaataaaacgcgaagcatccgcatttgctgtaccgcagaagacatggcttttgcagttccg
ccgttaccttctggttttcaccaaatatttctacggattgttaagccactgctgaatctgatccatggcaaaacgggcgagcat
aaaatcagcaagcgcctcgctggcatttttaataaatacgccctggcaacaccacggctgactgggctgcggtattcgtg
actccatgcccaacgccactttatttagggtattacctaccagctctttacttaaggcattcgtttgcaggcccatcttgctaccc
acattacccagacgctagtaatacgttgcatccctgggtaaagagtttgctgccgtttgcgccaactgtttcagcacgtta
ggcaccaacttcttaatcgttcgcccatcattttgctcagcgcgttacccagtttcgccgccgcgcctttcccgacaactgcga
ccaccacaatgaccgccaccatggcaatagcggcgacaatcgcaccaacaatgctgccggccatctctgccgttttcttat
cgacgcctaatcctccagcgctttggtaatcgccttgccaatcagctccattaacggcttcagcacatgctccataatcgggt
ttagcgcctgctgaataaaacgacactcccgtcgccgcctcacaatttcatcgccaccattaccgcaagtccacacgcag
ccagcgccagactcgccccaccggtaaaaacagcggccacaaacgctgacaatggttagcagcgcgcgaggacttcc
cgatacatcccataatgcggttcgtttcctcggctttgcgcgtctcttctggaattcagccgatttctttccatctccgcctgacg
cccttcctgcaaggcgttgaaaagcgcaagatcgttttgcaggctttcttccgtattttgcccacaatctcaataaacatggcc
atgagcatagtgaggcgggcgacatttgacagattatcctgctcaccctgggaaacctgattctgagaggcggcattagcc
gttccctggaatttggtcagaatgttatccgctttctcggctttcgctttggcgtctgtgcctgctttaaccgtcgcatccgtggcctt
atctaaggcctcttcgcctctgtcgcttcttttccggcctgttctaccgcgcgcttcagcttgtgcatagccgggtcagccgggtc
cagcgattgcaatttattttgcgcctgcgtcagttttttggtcgcagcgtcataaacactcttggcgggtatccgtcttttgatactgg
cttcatagagatccgtcgcctcctgagcctctcccagagccgtctgaatctttcgataccctgaatccccatctcttttgtgact
caatcatgcctgccatacgccagacgagactccagttgagacagcgaaacatcgcccagtagggtcattaacttgcca
agcagtaatgtcaattgccctcgctggagagttttccgggcggcgtccgtaggcggctttagacccaccgtattaatagc
gctctcgccggactttgtccggctttaaggtcgcccgctttcgttgccaccacatctttaaaagctttatccgccgcttttaaaaa
gtccgtgttcttacgaacgccttcaaaaagccgcctcagcgaggcgcggattttgggtatatccgctacggctaatgctacttgc
gtcatttaccat (SEQ ID NO: 2)

*Figures 12A-B*

C. MLNIQNYSASPHPGIVAERPQTPSASEHAEIAVVPSTTEHRGTDIISLSQAATKIQQAQQ
TLQSTPPISEENNDERTLARQQLTSSLNALAKSGVSLSAEQNENLRSTFSARRRPYLAL
RLWPARTTISDAEIWDMVSQNISAIGDSYLGVYENVVAVYTDFYQAFSDILSKMGGWLS
PGKDGNTIKLNVDSLKSEISSLINKYTQINKNTILFPSQTGSGMTTATKAEAEQWIKELNL
PDSCLKASGSGYVVLVDTGPLSKMVSDLNGIGSGSALELDNAKYQAWQSGFKAQEEN
LKTTLQTLTQKYSNANSLYDNLVKVLSSTISSSLETAKSFLQG (SEQ ID NO: 3)

D. atgcttaatattcaaaattattccgcttctcctcatccggggatcgttgccgaacggccgcagactccttcggcgagcgagca
cgccgagattgccgtggtaccgtctaccacagaacatcgcggcacagatatcatttcattatcgcaggcggctactaaaatc
cagcaggcacagcagacgctgcagtcaacgccaccgatttctgaagagaataatgacgagcgcacgctggcgcgcca
acagttgaccagcagcctgaatgcgctggcgaagtccggcgtgtcattatccgcagaacaaaatgagaacctgcggagc
acgtttctgcgcgacgtggccttatttagcgcttcgcctatgccagcgagaacaaccattctgatgctgagattgggata
tggtttcccaaaatatatcggcgataggtgacagctacctgggcgttatgaaaacgttgtcgcagtctataccgattttatca
ggccttcagtgatattctttccaaaatggaggctggttatcgcctggtaaggatggaaataccattaagctaaatgttgactc
acttaaaagtgaaataagtagtttaattaataaatacactcaaataaataaaaatacgattttatttccctcgcaaactggcag
cggaatgacaacagcaacgaaagcggaagctgagcagtggattaaagaattgaattaccggacagctgtctaaaggc
gtctggttctggttatgtcgtactggtggatacggggccactgagcaaaatggttagcgatcttaatggaataggatcgggttc
agcccttgaactggataacgccaaatatcaagcctggcagtcgggttttaaagcacaggaagaaaatctgaaaaccaca
ttacagacgctgacgcaaaaatatagcaatgccaattcattgtacgacaacctggtaaaagtgctgagcagtacgataagt
agcagcctggaaaccgccaaaagcttcctgcaaggataa (SEQ ID NO: 4)

E. MSSGNILWGSQNPIVFKNSFGVSNADTGSQDDLSQQNPFAEGYGVLLILLMVIQAIANN
KFIEVQKNAERARNTQEKSNEMDEVIAKAAKGDAKTKEEVPEDVIKYMRDNGILIDGMTI
DDYMAKYGDHGKLDKGGLQAIKAALDNDANRNTDLMSQGQITIQKMSQELNAVLTQLT
GLISKWGEISSMIAQKTYS (SEQ ID NO: 5)

F. atgtcttcaggaaacatcttatggggaagtcaaaaccctattgtgtttaaaaatagcttcggcgtcagcaacgctgataccgg
gagccaggatgacttatcccagcaaaatccgtttgccgaagggtatggtgttttgcttattctccttatggttattcaggctatcgc
aaataataaatttattgaagtccagaagaacgctgaacgtgccagaaatacccaggaaaagtcaaatgagatggatgag
gtgattgctaaagcagccaaggggatgctaaaaccaaagaggaggtgcctgaggatgtaattaaatacatgcgtgata
atggtattctcatcgatggtatgaccattgatgattatatggctaaatatgcgatcatgggaagctggataaaggtggcctac
aggcgatcaaagcggctttggataatgacgccaaccggaataccgatcttatgagtcaggggcagataacaattcaaaa
aatgtctcaggagcttaacgctgtccttacccaactgacagggcttatcagtaagtgggggaaatttccagtatgatagcg
cagaaaacgtactcatga (SEQ ID NO: 6)

Figures 12C-F

```
MLNIQNYSASPHPGIVAERPQTPSASEHAEIAVVPSTTEHRGTDIISLSQAATKIQQAQQ
TLQSTPPISEENNDERTLARQQLTSSLNALAKSGVSLSAEQNENLRSTFSARRRPYLAL
RLWPARTTISDAEIWDMVSQNISAIGDSYLGVYENVVAVYTDFYQAFSDILSKMGGWLS
PGKDGNTIKLNVDSLKSEISSLINKYTQINKNTILFPSQTGSGMTTATKAEAEQWIKELNL
PDSCLKASGSGYVVLVDTGPLSKMVSDLNGIGSGSALELDNAKYQAWQSGFKAQEEN
LKTTLQTLTQKYSNANSLYDNLVKVLSSTISSSLETAKSFLQGVDMVNDASSISRSGYTQ
NPRLAEAAFEGVRKNTDFLKAADKAFKDVVATKAGDLKAGTKSGESAINTVGLKPPTDA
AREKLSSEGQLTLLLGKLMTLLGDVSLSQLESRLAVWQAMIESQKEMGIQVSKEFQTAL
GEAQEATDLYEASIKKTDTAKSVYDAATKKLTQAQNKLQSLDPADPGYAQAEAAVEQA
GKEATEAKEALDKATDATVKAGTDAKAKAEKADNILTKFQGTANAASQNQVSQGEQDN
LSNVARLTMLMAMFIEIVGKNTEESLQNDLALFNALQEGRQAEMEKKSAEFQEETRKAE
ETNRIMGCIGKVLGALLTIVSVVAAVFTGGASLALAAVGLAVMVADEIVKAATGVSFIQQ
ALNPIMEHVLKPLMELIGKAITKALEGLGVDKKTAEMAGSIVGAIVAAIAMVAVIVVVAVV
GKGAAAKLGNALSKMMGETIKKLVPNVLKQLAQNGSKLFTQGMQRITSGLGNVGSKM
GLQTNALSKELVGNTLNKVALGMEVTNTAAQSAGGVAEGVFIKNASEALADFMLARFA
MDQIQQWLKQSVEIFGENQKVTAELQKAMSSAVQQNADASRFILRQSRA
(SEQ ID NO: 7)
```

*Figure 13A*

```
ATGCTTAATATTCAAAATTATTCCGCTTCTCCTCATCCGGGGATCGTTGCCGAACGGCCGCAGACTCCCT
CGGCGAGCGAGCACGTCGAGACTGCCGTGGTACCGTCTACCACAGAACATCGCGGTACAGATATCATTTC
ATTATCGCAGGCGGCTACTAAAATCCACCAGGCACAGCAGACGCTGCAGTCAACGCCACCGATCTCTGAA
GAGAATAATGACGAGCGCACGCTGGCGCGCCAGCAGTTGACCAGCAGCCTGAATGCGCTGGCGAAGTCCG
GCGTGTCATTATCCGCAGAACAAAATGAGAACCTGCGGAGCGCGTTTTCTGCGCCGACGTCGGCCTTATT
TAGCGCTTCGCCTATGGCGCAGCCGAGAACAACCATTTCTGATGCTGAGATTTGGGATATGGTTTCCCAA
AATATATCGGCGATAGGTGACAGCTATCTGGGCGTTTATGAAAACGTTGTCGCAGTCTATACCGATTTTT
ATCAGGCCTTCAGTGATATTCTTTCCAAAATGGGAGGCTGGTTATTACCAGGTAAGGACGGTAATACCGT
TAAGCTAGATGTTACCTCACTCAAAAATGATTTAAACAGTTTAGTCAATAAATATAATCAAATAAACAGT
AATACCGTTTTATTTCCAGCGCAGTCAGGCAGCGGCGTTAAAGTAGCCACTGAAGCGGAAGCGAGACAGT
GGCTCAGTGAATTGAATTTACCGAATAGCTGCCTGAAATCTTATGGATCCGGTTATGTCGTCACCGTTGA
TCTGACGCCATTACAAAAAATGGTTCAGGATATTGATGGTTTAGGCGCGCCGGGAAAAGACTCAAAACTC
GAAATGGATAACGCCAAATATCAAGCCTGGCAGTCGGGTTTTAAAGCGCAGGAAGAAAATATGAAAACCA
CATTACAGACGCTGACGCAAAAATATAGCAATGCCAATTCATTGTACGACAACCTGGTAAAAGTGCTGAG
CAGTACGATAAGTAGCAGCCTGGAAACCGCCAAAAGCTTCCTGCAAGGAGTCGACATGGTAAATGACGCA
AGTAGCATTAGCCGTAGCGGATATACCCAAAATCCGCGCCTCGCTGAGGCGGCTTTTGAAGGCGTTCGTA
AGAACACGGACTTTTTAAAAGCGGCGGATAAAGCTTTTAAAGATGTGGTGGCAACGAAAGCGGGCGACCT
TAAAGCCGGAACAAAGTCCGGCGAGAGCGCTATTAATACGGTGGGTCTAAAGCCGCCTACGGACGCCGCC
CGGGAAAAACTCTCCAGCGAAGGGCAATTGACATTACTGCTTGGCAAGTTAATGACCCTACTGGGCGATG
TTTCGCTGTCTCAACTGGAGTCTCGTCTGGCGGTATGGCAGGCGATGATTGAGTCACAAAAAGAGATGGG
GATTCAGGTATCGAAAGAATTCCAGACGGCTCTGGGAGAGGCTCAGGAGGCGACGGATCTCTATGAAGCC
AGTATCAAAAGACGGATACCGCCAAGAGTGTTTATGACGCTGCGACCAAAAAACTGACGCAGGCGCAAA
ATAAATTGCAATCGCTGGACCCGGCTGACCCCGGCTATGCACAAGCTGAAGCCGCGGTAGAACAGGCCGG
AAAAGAAGCGACAGAGGCGAAAGAGGCCTTAGATAAGGCCACGGATGCGACGGTTAAAGCAGGCACAGAC
GCCAAAGCGAAAGCCGAGAAAGCGGATAACATTCTGACCAAATTCCAGGGAACGGCTAATGCCGCCTCTC
AGAATCAGGTTTCCCAGGGTGAGCAGGATAATCTGTCAAATGTCGCCCGCCTCACTATGCTCATGGCCAT
GTTTATTGAGATTGTGGGCAAAAATACGGAAGAAAGCCTGCAAAACGATCTTGCGCTTTTCAACGCCTTG
CAGGAAGGGCGTCAGGCGGAGATGGAAAAGAAATCGGCTGAATTCCAGGAAGAGACGCGCAAAGCCGAGG
AAACGAACCGCATTATGGGATGTATCGGGAAAGTCCTCGGCGCGCTGCTAACCATTGTCAGCGTTGTGGC
CGCTGTTTTTACCGGTGGGGCGAGTCTGGCGCTGGCTGCGGTGGACTTGCGGTAATGGTGGCCGATGAA
ATTGTGAAGGCGGCGACGGGAGTGTCGTTTATTCAGCAGGCGCTAAACCCGATTATGGAGCATGTGCTGA
AGCCGTTAATGGAGCTGATTGGCAAGGCGATTACCAAAGCGCTGGAAGGATTAGGCGTCGATAAGAAAAC
GGCAGAGATGGCCGGCAGCATTGTTGGTGCGATTGTCGCCGCTATTGCCATGGTGGCGGTCATTGTGGTG
GTCGCAGTTGTCGGGAAAGGCGCGGCGGCGAAACTGGGTAACGCGCTGAGCAAAATGATGGGCGAAACGA
TTAAGAAGTTGGTGCCTAACGTGCTGAAACAGTTGGCGCAAAACGGCAGCAAACTCTTTACCCAGGGGAT
GCAACGTATTACTAGCGGTCTGGGTAATGTGGGTAGCAAGATGGGCCTGCAAACGAATGCCTTAAGTAAA
GAGCTGGTAGGTAATACCCTAAATAAAGTGGCGTTGGGCATGGAAGTCACGAATACCGCAGCCCAGTCAG
CCGGTGGTGTTGCCGAGGGCGTATTTATTAAAAATGCCAGCGAGGCGCTTGCTGATTTATGCTCGCCCG
TTTTGCCATGGATCAGATTCAGCAGTGGCTTAAACAATCCGTAGAAATATTTGGTGAAAACCAGAAGGTA
ACGGCGGAACTGCAAAAAGCCATGTCTTCTGCGGTACAGCAAAATGCGGATGCTTCGCGTTTTATTCTGC
GCCAGAGTCGCGCATAA (SEQ ID NO: NO:8)
```

Figure 13B

USE OF THE *SALMONELLA* SPP TYPE III SECRETION PROTEINS AS A PROTECTIVE VACCINATION

CROSS REFERENCE TO RELATED APPLICATIONS

In accordance with 37 C.F.R. § 1.76, a claim of priority is included in an Application Data Sheet filed concurrently herewith. The present application is a continuation of U.S. patent application Ser. No. 15/950,735, filed Apr. 11, 2018, which is a continuation in part application of U.S. patent application Ser. No. 15/013,454, filed Feb. 2, 2016, now U.S. Pat. No. 9,950,053, issued Apr. 24, 2018, which is a continuation in part application of U.S. patent application Ser. No. 14/437,535 filed Apr. 22, 2015, now abandoned, which is a 35 U.S.C. § 371 U.S. National stage application of PCT/US2013/66105 filed Oct. 22, 2013 which claims priority to U.S. Provisional application No. 61/716,911 filed Oct. 22, 2012, the complete disclosures of which are herein incorporated by reference.

SEQUENCE LISTING

A Sequence Listing was filed in electronic format on Oct. 7, 2022. The Sequence Listing was provided as a file entitled "10776_023US2_Sequence_Listing.xml", created Oct. 7, 2022, which is 35630 bytes in size. The information in the electronic format of the Sequence Listing is incorporated herein by reference in its entirety.

FIELD OF THE INVENTION

The invention generally relates to protecting against *Salmonella*-type pathogens and, more particularly, to compositions and methods for immunizing against infection by typhoidal and non-typhoidal *Salmonella* serovars.

BACKGROUND

*Salmonella* is a genus of over 2000 serovars and includes organisms that cause a wide range of human and animal diseases. For example, *Salmonella enterica* serovars *Typhi* and Paratyphi A and B cause enteric ("typhoid") fever, *Salmonella enterica* serovars *Typhimurium* and *Enteritidis* are known as the non-typhoidal *Salmonella* (NTS) and cause *salmonellosis-a* gastroenteritis which is usually a self-limiting illness in healthy individuals.

As is the case with many gram-negative pathogens, *Salmonella* spp. use type III secretion systems (T3SSs) as virulence factors to deliver proteins into host cells and to subsequently cause/induce infection. The T3SS is a molecular "syringe and needle" apparatus, also known as a "type III secretion apparatus" (T3SA) which promotes uptake of the bacterium by the host cell, and then adaptation of the intracellular environment of the host cell to allow a productive infection. *Salmonella* has two functionally distinct T3SS's which are encoded by *Salmonella* "pathogenicity islands" 1 and 2 (SPI-1 and -2). The SPI-1 T3SS is central to the ability of *Salmonella* to invade no phagocytic cells via the injection, from the bacteria and into the cell by way of the T3SA conduit, effector proteins which trigger extensive actin rearrangements on the surface of host cells. While this allows ingress of the pathogen into the host cell, a second T3SS island, SPI-2, is essential for bacterial replication/proliferation inside host cells. Upon intracellular activation of SPI-2, the bacteria proliferate within membrane-bound vacuoles of phagocytic eukaryotic cells (*Salmonella*-containing vacuoles, SCVs), with macrophages being the main cell type supporting bacterial growth in vivo. Bacterial effector proteins are translocated across the vacuolar membrane via the SPI-2 T3SS apparatus and into the host endomembrane system and cytoplasm, causing systemic disease.

The *Salmonella* NTS serotypes are a primary cause of foodborne illnesses worldwide. In the U.S. NTS are a leading cause of hospitalization and death due to foodborne illnesses, with *Salmonella enterica* serovar *Typhimurium* being the most frequent cause, 95% of the total cases of NTS are caused by contaminated food. Unfortunately, absolute protection from infection by enhanced agricultural surveillance is not feasible. Vaccines against these pathogens could provide a major weapon in controlling this disease. However, although some progress has been made in recent years, vaccines against *Salmonella* spp. have not proven to be broadly protective, and almost all are entirely directed only to the typhoid causing serovars. A Salmonella serotype-independent subunit vaccine that could target both typhoid and NTS serovars would be of tremendous public health value.

SUMMARY

Proteins associated with the tip of the T3SA in both SPI-1 and SPI-2 are extracellular, and thus are excellent candidates for the development of broadly protective serotype-independent subunit vaccines against *Salmonella*. Herein, the successful use of extracellular SPI-1 and SPI-2 proteins to immunize mammals against the effects of *Salmonella* infection is shown. Accordingly, compositions (e.g. immunogenic compositions) comprising one or more of the SPI-1 and SPI-2 proteins, or immunogenic fragments thereof, are provided, as are methods of using the compositions to elicit an immune response in and/or to vaccinate a mammal. Advantageously, in some aspects the methods and compositions provide broad serovar-independent protection against infection by both typhoid and NTS *Salmonella* serovars.

In one aspect, the invention provides methods of eliciting an immune response against at least one *Salmonella* serovar in a subject in need thereof. The methods comprise the steps of administering to the subject a composition comprising i) at least one *Salmonella* pathogenicity island 1 (SPI-1) and/or *Salmonella* pathogenicity island 2 (SPI-2) extracellular protein; and ii) a physiologically acceptable carrier; wherein said composition is administered in an amount so as to elicit an immune response to the at least one *Salmonella* serovar in said subject. In some aspects, the composition further comprises an adjuvant. In other aspects, the composition comprises an extracellular protein selected from the group consisting of: SipD, SipB, SseB and SseC. For example, the composition may comprise SipD and SipB; and the composition may further comprise SseB. In some aspects, the *Salmonella* serovar is *Salmonella enterica* serovar. In further aspects, the at least one *Salmonella enterica* serovar may be: typhoid serovar *Typhi*, typhoid serovar Paratyphi A, typhoid serovar Paratyphi B, non-typhoidal serovar *Typhimurium* and non-typhoidal serovar *Enteritidis*. In additional aspects, the subject is selected from a human and an agricultural animal, with exemplary agricultural animals including cattle, poultry, swine, horses, sheep and goats.

In other aspects, the invention provides immunogenic compositions comprising i) at least one *Salmonella* pathogenicity island 1 (SPI-1) and/or *Salmonella* pathogenicity island 2 (SPI-2) extracellular protein; and it) a physiologically acceptable carrier. In some aspects, the immunogenic composition further comprises an adjuvant. In further aspects, the at least one SPI-1 and/or SPI-2 extracellular protein is SipD, SipB, SseB or SseC. In some aspects, the at least one SPI-1 and/or SPI-2 extracellular proteins in the immunogenic compositions include SipD and SipB. In other aspects, the immunogenic compositions further comprise SseB.

In other aspects of the invention, what is provided are methods of treating or preventing *Salmonella* infection by one or both of a typhoid *Salmonella* serovar and a non-typhoid *Salmonella* serovar in a subject in need thereof. The methods comprise administering to the subject an amount of a composition comprising i) at least one *Salmonella* pathogenicity island 1 (SPI-1) and/or *Salmonella* pathogenicity island 2 (SPI-2) extracellular protein; and ii) a physiologically acceptable carrier. In some aspects, the immunogenic composition further comprises an adjuvant. In further aspects, the at least one SPI-1 and/or SPI-2 extracellular protein is SipD, SipB, SseB or SseC. In some aspects, the at least one SPI-1 and/or SPI-2 extracellular proteins in the immunogenic compositions include SipD and SipB. In other aspects, the immunogenic compositions further comprise SseB. The amounts that are administered are sufficient to treat or prevent said *Salmonella* infection in said subject.

In yet other aspects, the invention provides methods of lessening the severity of symptoms of *Salmonella* infection in a subject in need thereof, comprising administering to the subject an amount of a composition comprising i) at least one *Salmonella* pathogenicity island 1 (SPI-1) and/or *Salmonella* pathogenicity island 2 (SPI-2) extracellular protein; and if) a physiologically acceptable carrier. In some aspects, the immunogenic composition further comprises an adjuvant. In further aspects, the at least one SPI-1 and/or SPI-2 extracellular protein is SipD, SipB, SseB or SseC. In some aspects, the at least one SPI-1 and/or SPI-2 extracellular proteins in the immunogenic compositions include SipD and SipB. In other aspects, the immunogenic compositions further comprise SseB. The amounts that are administered are sufficient to lessen the severity of said symptoms in said subject.

In additional aspects, the invention provides methods of decreasing fecal shedding of *Salmonella* from a subject who is or is likely to be infected with *Salmonella*, comprising administering to the subject an amount of a composition comprising i) at least one *Salmonella* pathogenicity island 1 (SPI-1) and/or *Salmonella* pathogenicity island 2 (SPI-2) extracellular protein; and ii) a physiologically acceptable carrier. In some aspects, the immunogenic composition further comprises an adjuvant. In further aspects, the at least one SPI-1 and/or SPI-2, extracellular protein is SipD, SipB, SseB or SseC. In some aspects, the at least one SPI-1 and/or SPI-2 extracellular proteins in the immunogenic compositions include SipD and SipB. In other aspects, the immunogenic compositions further comprise SseB. The amount that is administered is sufficient to lessen the severity of said symptoms in said subject.

The foregoing has outlined in broad terms the more important features of the invention disclosed herein so that the detailed description that follows may be more clearly understood, and so that the contribution of the instant inventors to the art may be better appreciated. The instant invention is not limited in its application to the details of the construction and to the arrangements of the components set forth in the following description or illustrated in the drawings. Rather the invention is capable of other embodiments and of being practiced and carried out in various other ways not specifically enumerated herein. Additionally, the disclosure that follows is intended to apply to all alternatives, modifications and equivalents as may be included within the spirit and the scope of the invention as defined by the appended claims. Further, it should be understood that the phraseology and terminology employed herein are for the purpose of description and should not be regarded as limiting, unless the specification specifically so limits the invention.

BRIEF DESCRIPTION OF THE DRAWINGS

Other objects and advantages of the invention will become apparent upon reading the following detailed description and upon reference to the drawings in which:

FIGS. 5C and 5D: number of SipD specific ASCs at days 42 and 56, respectively: FIGS. 5E and 5F: number of SseB specific ASCs at days 42 and 56, respectively.

FIG. 6A: SipB specific IgG; FIG. 6B: SipD specific IgG; FIG. 6C: SseB specific IgG.

FIGS. 10A and 10B. Antibody titers of calves immunized as described in Example 3, on day 56 post-immunization. FIG. 10A: serum IgG; FIG. 10B; saliva IgA.

FIGS. 11A and 11B. Bacterial shedding in response to challenge with *S. enterica* Newport (FIG. 11A) or *S. enterica Typhimurium* (FIG. 11B) in calves on day 56 post-immunization.

FIGS. 12A-12F. Sequences of proteins of interest and nucleic acid sequence encoding them. FIG. 12A: amino acid sequence of SipB (SEQ ID NO: 1); FIG. 12B: nucleic acid sequence encoding SipB (SEQ ID NO: 2); FIG. 12C: amino acid sequence of SipD (SEQ ID NO: 3); FIG. 12D: nucleic acid sequence encoding SipD (SEQ ID NO: 4); FIG. 12E: amino acid sequence of SseB (SEQ ID NO: 5); FIG. 12F: nucleic acid sequence encoding SseB (SEQ ID NO: 6).

FIGS. 13A and 13B. FIG. 13A: Amino acid; and FIG. 13B; encoding nucleic acid sequences of SipD-SipB chimera (SEQ ID NOS: 7 and 8, respectively).

Figures 16A, 16B:
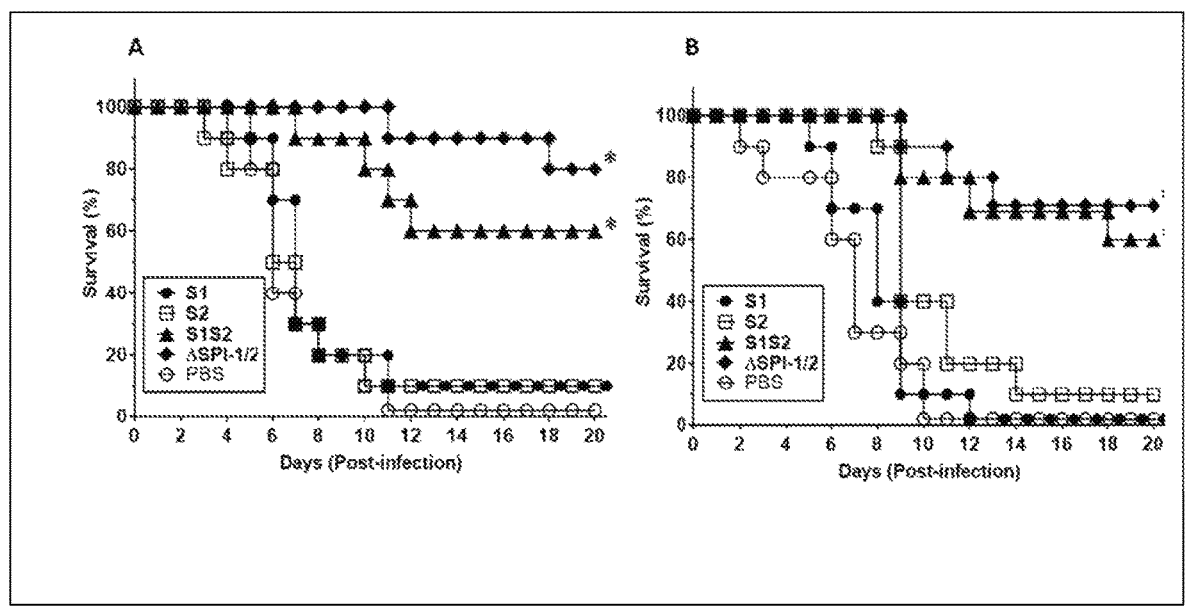

FIGS. 16A and 16B are graphs showing the results from an orogastric/systemic challenge with *S. typhimurium* SL1344 and *S. enteritidis* P125109. Immunized mice (n=10) were challenged with (FIG. 16A) $2 \times 10^8$ cfu *S. typhimurium* SL1344 and (FIG. 16B) $8 \times 10^7$ cfu *S. enteritidis* orogastrically. Survival was monitored for 21 days. $p<0.05$ for ΔSPI-1/2 and SIF+S2F compared to PBS group.

Figure 17:
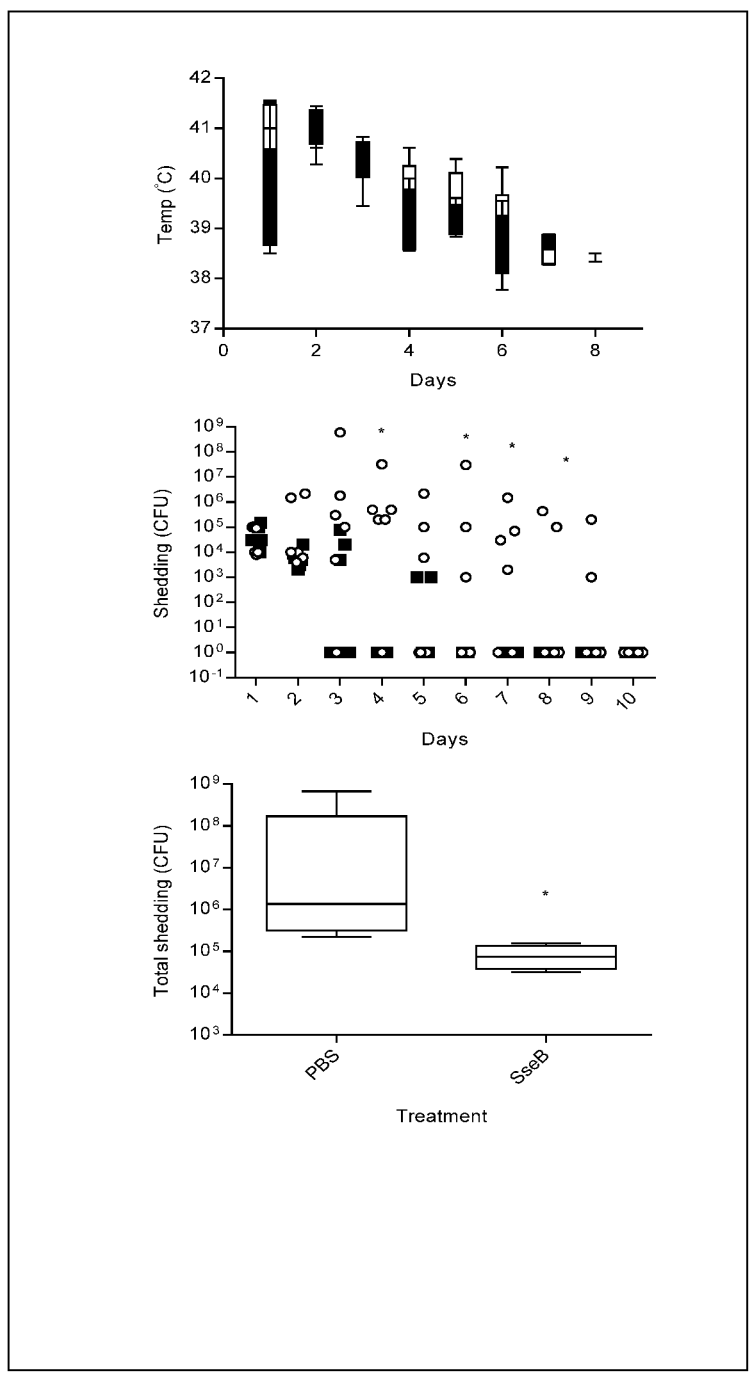

FIG. 17 is a series of graphs showing rRectal temperatures and shedding of S. Newport following bacterial challenge of calves. Top: Temperatures of the calves over the course of eight days after challenge. Black boxes indicate temperature from calves vaccinated with SseB+dmLT and white boxes are sham-vaccinated calves. Middle: fecal shedding (CFUs/gram of feces) for individual calves over the ten day study. Black boxes indicate shedding from each calf vaccinated with SseB+dmLT and white circles are sham-vaccinated calves, Bottom: Total shedding of bacteria (CFUs) over the entire ten day period. * $P<0.05$ comparing groups that received SseB+dmLT and PBS using T test.

Figure 18:
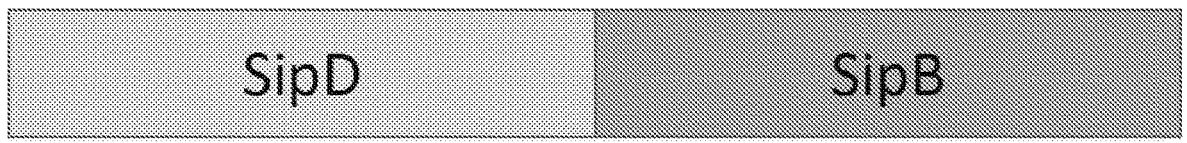

FIG. 18 is a schematic representation of the $1 Fusion (S1 or SIF). SIF is a genetic fusion of SipD and SipB. Upon protein purification, the linear model is depicted in the diagram where SipD is expressed first (light grey) with translation continuing into SipB (dark, grey).

Figure 19:
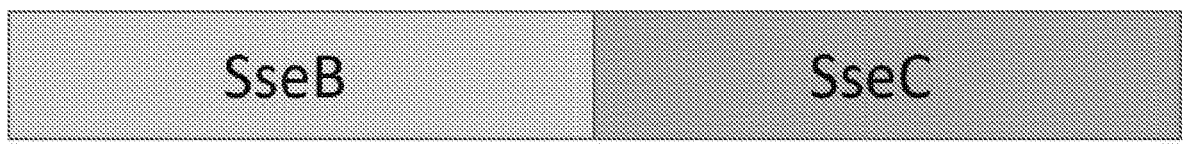

FIG. 19 is a schematic representation of the S2 Fasion (S2 or $2F). S2F is a genetic fusion of SseB and SseC. Upon protein purification, the linear model is depicted in the drawing where SseB is expressed first (light grey) with translation continuing into SipB (dark grey).

DETAILED DESCRIPTION

While this invention is susceptible of embodiment in many different forms, there is shown in the drawings, and will herein be described hereinafter in detail, some specific embodiments of the instant invention. It should be understood, however, that the present disclosure is to be considered an exemplification of the principles of the invention and is not intended to limit the invention to the specific embodiments or algorithms so described.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It should be noted that where reference is made herein to a method comprising two or more defined steps, the defined steps can be carried out in any order or simultaneously (except where context excludes that possibility), and the method can also include one or more other steps which are carried out before any of the defined steps, between two of the defined steps, or after all of the defined steps (except where context excludes that possibility).

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Thus, for example, reference to includes reference to one or more of such serovars, unless otherwise specified. The use of plural terms is also not intended to be limiting, unless otherwise specified. Furthermore, to the extent that the terms "including", "includes", "having", "has", "with", or variants thereof are used in either the detailed description and/or the claims, such terms are intended to be inclusive in a manner similar to the term "comprising."

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 100%, up to 59%, or up to 19% of a given value or range. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed. The recitation of numerical ranges by endpoints includes all numbers within that range (e.g., 1 to 5 includes 1, 1.5, 2, 2.75, 3, 3.80, 4, and 5).

The term "at least" followed by a number is used herein to denote the start of a range beginning with that number (which may be a ranger having an upper limit or no upper limit, depending on the variable being defined). For example, "at least I" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%.

When, in this specification, a range is given as "(a first number) to (a second number)" or "(a first number) (a second number)", this means a range whose lower limit is the first number and whose upper limit is the second number. For example, 25 to 100 should be interpreted to mean a range whose lower limit is 25 and whose upper limit is 100. Additionally, it should be noted that where a range is given, every possible subrange or interval within that range is also specifically intended unless the context indicates to the contrary. For example, if the specification indicates a range of 25 to 100 such range also is intended to include subranges such as 26 to 100, 27 to 100, etc., 25 to 99, 25 to 98, etc., as well as any other possible combination of lower and upper values within the stated range, e.g., 33-47, 60-97, 41-45, 28-96, etc. Note that integer range values have been used in this paragraph for purposes of illustration only and decimal ranges (e.g., 46.7-91,3) should also be understood to be intended as a possibility unless specifically excluded.

As used herein, a "chimeric" molecule is one which comprises one or more unrelated types of components, moieties or two or more chemically distinct regions which can be conjugated to each other, fused, linked, transcribed, translated, attached via a linker, chemically synthesized, expressed from a nucleic acid sequence, etc. For example, a fusion gene, a peptide and a nucleic acid sequence, a peptide and a detectable label, two or more peptide sequences, two or more nucleic acid sequences (e.g. from different regions of a genome, nucleic acid sequences not found contiguous in nature, fusion genes) and the like. As used herein, a "fusion gene" is a gene created by removing the stop protein from the sequence of a gene and attaching the DNA sequence of a second gene to the first. By fusing one nucleotide sequence to another, the host cell will express the sequences together, as a single fused protein. Fusion genes may contain two or more fused genes. Accordingly, "fusion protein" as used herein is a protein produced by expression of a fusion gene or two or more proteins fused or connected by any method. The term encompasses peptides, mutants, derivatives and any variants.

As used herein, the terms "conjugated," "linked." "attached," "fused" and "tethered," when used with respect to two or more moieties, means that the moieties or domains are physically associated or connected with one another, either directly or via one or more additional moieties that serve as a linking agent, to form a structure that is sufficiently stable so that the moieties remain physically associated under the conditions in which the structure is used, e.g., physiological conditions. The linkage can be based on genetic fusion according to the methods known in the art and described herein or can be performed by, e.g., chemical cross-linking. The additional domain present in the construct may be linked by a flexible linker, such as a polypeptide linker to one of the binding site domains; the polypeptide linker can comprise plural, hydrophilic or peptide-bonded amino acids of a length sufficient to span the distance between the C-terminal end of one of the domains and the N-terminal end of the other of the domains when the polypeptide assumes a conformation suitable for binding when disposed in aqueous solution. The term "connected" will be used for the sake of brevity and is meant to include all possible methods of physically associating each domain of the chimeric molecule to each other.

As used herein, unless otherwise indicated, the terms "peptide", "polypeptide" or "protein" are used interchangeably herein, and refer to a polymer of amino acids of varying sizes. These terms do not connote a specific length of a polymer of amino acids. Thus, for example, the terms oligopeptide, protein, and enzyme are included within the definition of polypeptide or peptide, whether produced using recombinant techniques, chemical or enzymatic synthesis, or be naturally occurring. This term also includes polypeptides that have been, modified or derivatized ("derivatives"), such as by glycosylation, acetylation, phosphorylation, and the like.

As used herein, "variants" of polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE software (DNASTAR).

As used herein, a "nucleic acid" or "nucleic acid sequence" or "cDNA" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs, and refers to nucleic acid sequences in which one or more introns have been removed. The terms "nucleic acid sequence", "polynucleotide," and "gene" are used interchangeably throughout the specification and includes linear or circular oligomers or polymers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. The nucleic acid sequences may be composed of different regions. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, for instance, DNA which is part of a hybrid gene encoding additional polypeptide sequences.

A "polynucleotide" means a single strand or parallel and anti-parallel strands of a nucleic acid. Thus, a polynucleotide may be either a single-stranded or a double-stranded nucleic acid.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, SIRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

By "encoding" or "encoded", "encodes" with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type target gene products. Variants may result from at least one mutation in a nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs.) or single base mutations in which the polynucleotide sequence varies by one base. The presence of SNPs may be indicative of, for example, a certain population with a propensity for a disease state, that is susceptibility versus resistance.

The term "*Salmonella*" is meant to include all *Salmonella* species and subspecies, including both typhoidal and non-typhoidal species, and all *S. enterica* subspecies.

The terms "*Salmonella* pathogenicity island 1 (SPI-1)" and "*Salmonella* pathogenicity island 2 (SPI-2)" is meant to include all of the genes encoded by SPI-1 and SPI-2 respectively. Reference to each of the molecules embodied herein, is meant to include, without limitation, nucleic acids, polynucleotides, oligonucleotides, peptides, polypeptides, proteins, homologous and/or orthologous molecules, mutants, variants, alleles, different species, and active fragments thereof. Accordingly, the terms "SPI-1", "SPI-2", "SipD", "SipB", "SicA", "SseB", "SseC", "SscA" etc., includes, for each of these molecules: nucleic acids, polynucleotides, oligonucleotides, peptides, polypeptides, proteins, homologous and/or orthologous molecules, mutants, variants, alleles, different species, and active fragments thereof.

"Vaccine" as used herein is a preparation that stimulates an immune response that produces immunity against particular antigens, e.g. *Salmonella* serotypes or serovars. Vaccines may be used to prevent infection, to create resistance to an infection or to ameliorate the effects of infection. Vaccines may contain, but are not limited to, live, attenuated infectious material such as viruses or bacteria, and dead or inactivated organisms or purified products derived therefrom. A vaccine can be administered by injection, orally or by inhalation. Injection may be, but are not limited to, subcutaneous (se), intramuscular (im), intraperitoneal (ip), intradermal (id) or intravenous (iv).

As used herein, the terms "elicit an immune response", "induces or enhances an immune response", or "stimulates an immune response" are used interchangeably herein, and refer to a statistically measurable induction or increase in an immune response over a control sample to which the peptide, polypeptide or protein has not been administered. Preferably the induction or enhancement of the immune response results in a prophylactic or therapeutic response in a subject. The subject mounts one or both of an innate and/or an adaptive immune reaction against antigenic determinants of the proteins or antigenic portions thereof that are administered. In particular, the adaptive immune reaction entails production of e.g. B and T cell lymphocytes and antibodies specific for binding and forming complexes with the antigenic determinants. In some embodiments, the proteins and/or antigenic fragments thereof elicit a protective immune response in the subject, i.e. administration of one or more of the proteins and/or antigenic portions thereof results in an immune response that is protective against later challenge by the disease causing organism itself, either preventing infection altogether, or lessening the impact of infection by decreasing disease symptoms that would otherwise occur, had the subject not been vaccinated as described herein. The compositions embodied herein, induce immune responses to all *Salmonella* serovars and include typhoidal and non-typhoidal serovars as well as *Salmonella* subspecies.

As used herein, an "adjuvant" is a substance that is able to favor or amplify the cascade of immunological events, ultimately leading to a better immunological response, i.e., the integrated bodily response to an antigen. An adjuvant is in general not required for the immunological response to occur, but favors or amplifies this response.

The term "immunoregulatory" is meant a vaccine, composition or substance that is immunogenic (i.e. stimulates or increases an immune response) or immunosuppressive (i.e. reduces or suppresses an immune response).

"Immunogen" or "antigen" as used herein is a substance that is foreign to the body that stimulates an immune response, such as the production of antibodies when introduced into the body. Immunogens or antigens are also capable of reacting with the products of an immune response. Immunogens or antigens may include, but are not limited to proteins or polypeptides, enzymes, toxins, bacteria, viruses, foreign tissues, foreign blood cells, and the cells of transplanted organs. Correspondingly, "immunogenicity" is the ability of an immunogen or antigen to stimulate an immune response. In the context of this invention, an "antigen" or "antigenic" composition or "immunogen" include without limitation any SPI-1 and/or SPI-2 molecules comprising proteins, polypeptides, peptides, polynucleotides, oligonucleotides, fragments, derivatives or variants thereof. Accordingly, an antigen includes the chimeric molecules comprising SipD, SipB, SseB or SseC proteins, polypeptides, peptides, polynucleotides, oligonucleotides, fragments, derivatives or variants thereof, as embodied herein.

"Cells of the immune system" or "immune cells", is meant to include any cells of the immune system that may be assayed, including, but not limited to, B lymphocytes, also called B cells, T lymphocytes, also called T cells, natural killer (NK) cells, natural killer T (NK) cells, lymphokine-activated killer (LAK) cells, monocytes, macrophages, neutrophils, granulocytes, mast cells, platelets. Langerhans cells, stem cells, dendritic cells, peripheral blood mononuclear cells, tumor-infiltrating (TIL) cells, gene modified immune cells including hybridomas, drug modified immune cells, and derivatives, precursors or progenitors of the above cell types.

"Immune effector cells" refers to cells capable of binding an antigen and which mediate an immune response selective for the antigen. These cells include, but are not limited to, T cells (T lymphocytes), B cells (B lymphocytes), monocytes, macrophages, natural killer (NK) cells and cytotoxic T lymphocytes (CTLs), for example CTL lines, CTL clones, and CTLs from tumor, inflammatory, or other infiltrates.

"Immune related molecules" refers to any molecule identified in any immune cell, whether in a resting ("non-stimulated") or activated state, and includes any receptor, ligand, cell surface molecules, nucleic acid molecules, polypeptides, variants and fragments thereof.

"T cells" or "T lymphocytes" are a subset of lymphocytes originating in the thymus and having heterodimeric receptors associated with proteins of the CD3 complex (e.g., a rearranged T cell receptor, the heterodimeric protein on the T cell surfaces responsible for antigen/MHC specificity of the cells). T cell responses may be detected by assays for their effects on other cells (e.g., target cell killing, activation of other immune cells, such as B-cells) or for the cytokines they produce.

A "secondary immune response" or "adaptive immune response" may be active or passive, and may be humoral (antibody based) or cellular that is established during the life of an animal, is specific for an inducing antigen, and is marked by an enhanced immune response on repeated encounters with said antigen. A key feature of the T lymphocytes of the adaptive immune system is their ability to detect minute concentrations of pathogen-derived peptides presented by MHC molecules on the cell surface.

"Antibody" or "immunoglobulin," as used herein is a protein produced by the immune system that helps destroy disease-causing organisms. Antibodies are made and secreted by B lymphocytes in response to stimulation by antigens, which may include vaccines. Antibodies are generally specific, binding only to the specific antigen that stimulated its production. A given antigen can have many epitopes, each on reacting with the immune system to create antibodies specific for each of the epitopes. Antibodies can be effective defenders against both bacteria and viruses, in addition to toxins. Antibodies can be polyclonal or monoclonal.

As used herein, the terms "protect"; "protecting", "provide protection to", "providing protection to", and "aids in the protection" do not require complete protection from any indication of infection. For example, "aids in the protection" can mean that the protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. Accordingly, "treating" or "treatment" of a state, disorder or condition includes: (1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition: (2) inhibiting the state, disorder or condition, i.e., arresting, reducing or delaying the development of the disease or a relapse thereof (in case of maintenance treatment) or at least one clinical of subclinical symptom thereof; or (3) relieving the disease, i.e., causing regression of the state, disorder or condition or at least one of its clinical or subclinical symptoms. The benefit to an individual to be treated is either statistically significant or at least perceptible to the patient or to the physician.

The terms "patient" or "individual" or "subject" are used interchangeably herein, and refers to an animal, such as a mammalian subject to be treated, with human patients being preferred, or a companion or domesticated or food- or feed-producing or livestock or game or racing or sport animal, for instance, a cow, a horse, a dog, a cat, a goat, a sheep or a pig, or fowl such as chickens, duck, turkey or any other organism which can benefit from the treatments embodied herein. In some cases, the methods of the invention find use in experimental animals, in veterinary application, and in the development of animal models for disease, including but not limited to, rodents including mice, rats, and hamsters; and primates.

As defined herein, a "therapeutically effective" amount of a compound or agent (i.e., an effective dosage) means an amount sufficient to produce a therapeutically (e.g., clinically) desirable result. The compositions can be administered from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compounds of the invention can include a single treatment or a series of treatments:

As defined herein, an "effective" amount of a compound or agent (i.e., an effective dosage) means an amount sufficient to produce a (e.g., clinically) desirable result. Accordingly, an "efficacious" vaccine comprises a therapeutically effective amount of a given antigen.

As used herein, a "pharmaceutically acceptable" component/carrier etc. is one that is suitable for use with humans and/or animals without undue adverse side effects (such as toxicity, irritation, and allergic response) commensurate with a reasonable benefit/risk ratio. When it is used, for example, to describe an excipient in a pharmaceutical vaccine, it characterizes the excipient as being compatible with the other ingredients of the composition and not disadvantageously deleterious to the intended recipient.

The term "carrier" refers to a diluent, adjuvant, excipient, or vehicle with which the compound is administered. Pharmaceutical acceptable carriers can be sterile liquids, such as water and/or oils, including those of petroleum, animal, vegetable or synthetic origin, such as peanut oil, soybean oil, mineral oil, sesame oil and the like. Water or aqueous solution saline solutions and aqueous dextrose and glycerol solutions can be employed as carriers, particularly for injectable solutions.

General Techniques

For further elaboration of general techniques useful in the practice of this invention, the practitioner can refer to standard textbooks and reviews in cell biology, microbiology, bacteriology, molecular biology tissue culture, and physiology.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999): Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Some reagents, cloning vectors, and kits for genetic manipulation referred to in this disclosure are available from commercial vendors. For example, such as BioRad, Stratagene, Invitrogen, Sigma-Aldrich, and ClonTech.

Composition

A vaccine that prevents colonization of *Salmonella* in deeper tissues (i.e. lymph nodes) reduces the risk of introducing this broad host-range pathogen from contaminating food products going into the market. The result is a safe source of protein that is important for consumer nutrition. Animal protein is an important component of a balanced diet for children in the United States. Children tend to be some of the hardest hit when *Salmonella* outbreaks occur. Their immune system is still developing and they have not been exposed to the variety of immunogens that boost that system. Foods in the meat category, such as, hamburgers, chicken and deli meats are the foods most likely to be contaminated with *Salmonella*. *Salmonella* has also been associated with dairy, plants, fruits and vegetables, such as, spinach, lettuce, tomatoes, cantaloupe and the like; and, processed foods such as peanut butter, ice cream, and the like.

The surface-exposed proteins at the tip of the two type III secretion (TTS) apparatus needles of *Salmonella* (both SPI-1 and SPI-2), as described herein for the development of vaccines, are protective against all *S. enterica* subspecies, as disclosed in detail in the examples section which follows. These include, but are not limited to: the initial tip protein SipD and the first 'translocator' protein SipB from *Salmonella* pathogenicity island-1 (SPI-1). Without being bound by theory, it is believed that disruption of the function of SPI-1 (e.g. by antibody binding to one or more of these proteins) prevents *Salmonella* protein delivery to host cells and thus blocks bacterial effects on the host cell. In addition, after entry into the cell, the proteins from SPI-2 are expressed and are surface exposed, and these proteins, which include but are not limited to: SseB and SseC, also provide vaccine targets. Without being bound by theory, it is believed that disruption of the SPI-2 apparatus (e.g. by antibody binding to one or more of these proteins) prevents successful replication of the bacteria within the host, and also blocks spread of the bacteria within the host, preventing systemic infection.

The present invention provides compositions for use in eliciting an immune response and/or vaccinating an individual against *Salmonella* infection, and/or against disease symptoms caused by *Salmonella* infection. The compositions include one or more substantially purified proteins, polypeptides or antigenic regions thereof as described herein, or substantially purified nucleic acid sequences (e.g. DNA cDNA, RNA, etc.) encoding such proteins, polypeptides or antigenic regions thereof, and a pharmacologically suitable/compatible carrier. By "substantially purified" it is meant that the molecule is largely free of other organic molecules, cellular debris, solvents, etc. when tested using standard techniques known to those of skill in the art (e.g. gel electrophoresis, column chromatography, sequencing, mass spectroscopy, etc.). For example, the molecule is generally at least about 50, 55, 60, 65, 70, or 75% pure by wt/%, and preferably is at least about 80, 85, 90, 95% or more pure (e.g. 96, 97, 98, 99 or even 100% pure). The preparation of proteins, polypeptides, and peptides as described herein is well-known to those in the art, and includes, for example, recombinant preparation; isolation from a natural source; chemical synthesis; etc. The purification of proteinaceous materials is also known. However, specific exemplary methods for preparing the vaccinating agents utilized in the practice of the invention are described in detail in the Examples section below.

Accordingly, proteins which make up SPI-1 and/or the SPI-2 of *Salmonella*, or antigenic portions thereof, are used to elicit an immune response in subjects to whom they are administered.

Exemplary proteins which may be used in the practice of the invention include but are not limited to: SipD. SipB, SseB and SseC, which may be administered alone or in various forms and combinations as described herein. Exemplary full length sequences of SipD. SipB, and SseB and nucleic acids that encode them are provided in FIGS. 12A-12F (SEQ ID NOS: 1-6). The phrase(s) "SipD, SipB, SseB and SseC protein(s)" as used herein refer to both the full length proteins as depicted in the figures, to antigenic regions (portions, fragments, etc.), derivatives, or variants thereof.

The proteins, polypeptides/peptides, polynucleotides, oligonucleotides, derivatives or variants thereof, which may be used in the practice of the invention include sequences which have at least about 50, 55, 60, 65, 70, 75, 80, 85, or 90% identity to the sequences comprising SEQ ID NOS: 1-8, 13-16, or 23-24, or to sections of those sequences: which correspond to antigenic regions. Typically, the level of identity is at least about 92, 93, 94, 95, 96, 97, 98 or 99%. Those of skill in the art are familiar with methods and software programs Tor sequence comparison to determine identity.

The proteins, polypeptides/peptides, polynucleotides, oligonucleotides, derivatives or variants thereof, which may be used in the practice of the invention, include SipD, SipB, SseB and SseC, which have at least about 50, 55, 60, 65, 70, 75, 80, 85, or 90% identity to the sequences presented herein, or to sections of those sequences which correspond to antigenic regions. Typically, the level of identity is at least about 92, 93, 94, 95, 96, 97, 98 or 99%, Those of skill in the art are familiar with methods and software programs for sequence comparison to determine identity.

The invention also encompasses the use of nucleic acids encoding the proteins/polypeptides/peptides, chimeric molecules described herein, i.e. nucleic acid vaccines are also contemplated, as are vectors for producing the proteins. Exemplary nucleic acid sequences encoding e.g. SipD, SipB, and SseB are presented in FIGS. 12B, 12D and 12F (SEQ ID NOS: 2, 4 and 6, respectively). An exemplary nucleic acid sequence encoding e.g. SipD-SipB and SseB-SseC chimeric molecules comprise SEQ ID NOS: 13 and 15 respectively, However, those of skill in the art will appreciate that the genetic code is redundant and that many sequences may encode a given amino acid sequence. All nucleic acid sequences (e.g. DNA, RNA, cDNA, DNA/RNA hybrids, etc.) which successfully encode and express the proteins/polypeptides/peptides described herein may be used in the practice of the invention, so long as administration results in elicitation of an immune response (e.g. a protective immune response) as described herein.

In some embodiments of the invention, the proteins, polypeptides or peptides that are used in the vaccine are chimeric or fusion proteins. The chimeric protein is translated from a single, contiguous nucleic acid molecule, and which comprises sequences from at least two different proteins or antigenic regions thereof. For example, a chimera of the invention may include two or more of SipD, SipB, SseB and SseC, or antigenic regions of two or more of these. Typically, the individual sequences are joined via a linker or spacer sequence of e.g. from about 2 to about 20 amino acids, usually from about 2 to about 10 amino acids. The amino acids in linking sequences are typically uncharged and the linker sequence usually does not exhibit secondary or tertiary structure, but does allow the fused protein/peptide segments to adopt functional secondary, tertiary, etc. conformations. One such exemplary chimera includes SipB and SipD. The amino acid sequence of this chimera is shown in FIG. 13A (SEQ ID NO: 7). The chimera may be encoded by any suitable nucleic acid sequence, e.g. the exemplary nucleic acid sequence depicted in FIG. 13B (SEQ ID NO: 8). In one embodiment the chimeric peptide is SEQ ID NOS: 14 or 16.

In some embodiments, the compositions of the invention comprise one or more molecules having at least about 60% sequence identity to SEQ ID NOS: 1-8, 13-16, or 23-24. In some embodiments, the compositions of the invention comprise one or more molecules of SEQ ID NOS: 1-8, 13-16, or 23-24. In some embodiments, the compositions of the invention comprise one or more molecules of SEQ ID NOS: 1-8, 13-16, or 23-24 proteins, polypeptides, peptides, polynucleotides, oligonucleotides, fragments, derivatives or variants thereof.

In an embodiment, a vaccine comprises a therapeutically effective amount of a chimeric molecule, the chimeric molecule comprising at least one *Salmonella* pathogenicity island 1 (SPI-1) and/or *Salmonella* pathogenicity island 2 (SPI-2) molecule or variants thereof. In embodiments, the SPI-1 and/or SPI-2 molecules comprise proteins, polypeptides, peptides, polynucleotides, oligonucleotides, fragments, derivatives or variants thereof. In other embodiments, the chimeric molecule comprises SipD, SipB, SseB or SseC proteins, polypeptides, peptides, polynucleotides, oligonucleotides, fragments, derivatives or variants thereof. In one embodiment, the chimeric molecule comprises a SipD protein, peptide, derivative or variants thereof connected to a SipB protein, peptide, derivative or variants thereof. In another embodiment, the chimeric molecule comprises an SseB protein, peptide, derivative or variants thereof, connected to an SseC protein, peptide or variants thereof. The vaccine can be formulated in a pharmaceutically acceptable carrier and/or an adjuvant. Alternatively, the adjuvant may be administered separately.

In another embodiment, the vaccine comprises a therapeutically effective amount of a chimeric molecule comprising a SipD protein, peptide, derivative or variants thereof connected to a SipB protein, peptide, derivative or variants thereof; and, a therapeutically effective amount of a chimeric molecule comprising an SseB protein, peptide or variants thereof, connected to an SseC protein, peptide, derivative or variants thereof. In another embodiment, the vaccine comprises a therapeutically effective amount of a chimeric molecule comprising a SipD protein, peptide, derivative or variants thereof connected to at least one of: a SipB, and/or an SseB, and/or an SseC, protein, peptide, derivative or variants thereof.

In another embodiment, the vaccine comprises a therapeutically effective amount of a chimeric molecule comprising a SipB protein, peptide, derivative or variants thereof connected to at least one of: a SipD, and/or an SseB, and/or an SseC, protein, peptide, derivative or variants thereof.

In another embodiment, the vaccine comprises a therapeutically effective amount of a chimeric molecule comprising an SseB protein, peptide, derivative or variants thereof connected to at least one of: a SipB, and/or SipD, and/or an SseC, protein, peptide, derivative or variants thereof.

In another embodiment, the vaccine comprises a therapeutically effective amount of a chimeric molecule comprising an SseC protein, peptide, derivative or variants thereof connected to at least one of: a SipB, and/or a SipD, and/or an SseB, protein, peptide, derivative or variants thereof.

In yet another embodiment, the vaccine comprises a therapeutically effective amount of one or more of: a SipB, a SipD, an SseB, an SseC, proteins, peptides, derivatives or variants thereof. The different molecules can be combined in doses over a period of time, administered separately or in any combination as determined by a health professional based on the severity of disease, age, sex or health of the subject.

In yet another embodiment, the vaccine comprises a therapeutically effective amount of SipB proteins, peptides, derivatives or variants thereof.

In yet another embodiment, the vaccine comprises a therapeutically effective amount of SipD proteins, peptides, derivatives or variants thereof.

In yet another embodiment, the vaccine comprises a therapeutically effective amount of SseB proteins, peptides, derivatives or variants thereof.

In yet another embodiment, the vaccine comprises a therapeutically effective amount of SseC proteins, peptides, derivatives or variants thereof.

In another embodiment, the vaccine comprises an expression vector encoding one or more molecules comprising at least one *Salmonella* pathogenicity island 1 (SPI-1) and/or *Salmonella* pathogenicity island 2 (SPI-2) molecules, derivatives or variants thereof. In embodiments, the expression vector encodes for at least one of SipD, SipB, SseB or SseC proteins, fragments, derivatives, variants or any combinations thereof. In one embodiment, the expression vector encodes for a SipD protein, peptide, derivative or variants thereof connected to a SipB protein, peptide, derivative or variants thereof. In another embodiment, the expression vector encodes for an SseB protein, peptide, derivative or variants thereof, connected to an SseC protein, peptide or variants thereof.

In another embodiment, the vaccine comprises an expression vector encoding a chimeric molecule comprising a SipB protein, peptide, derivative or variants thereof connected to at least one of: a SipD, and/or an SseB, and/or an SseC protein, peptide, derivative or variants thereof.

In another embodiment, the vaccine comprises an expression vector encoding a chimeric molecule comprising an SseB protein, peptide, derivative or variants thereof connected to at least one of: a SipB, and/or SipD, and/or an SseC protein, peptide, derivative or variants thereof.

In another embodiment, the vaccine comprises an expression vector encoding a chimeric molecule comprising an SseC protein, peptide, derivative or variants thereof connected to at least one off a SipB, and/or a SipD, and/or an SseB protein, peptide, derivative or variants thereof.

In yet another embodiment, the vaccine comprises an expression vector encoding one or more of: a SipB, a SipD, an SseB, an SseC protein, peptide, derivative or variants thereof.

In yet another embodiment, the vaccine comprises an expression vector encoding SipB proteins, peptides, derivatives or variants thereof.

In yet another embodiment, the vaccine comprises an expression vector encoding SipD proteins, peptides, derivatives or variants thereof.

In yet another embodiment, the vaccine comprises an expression vector encoding SseB proteins, peptides, derivatives or variants thereof.

In yet another embodiment, the vaccine comprises an expression vector encoding SseC proteins, peptides, derivatives or variants thereof.

In yet another embodiment, the vaccine comprises an expression vector comprising at least one of SEQ ID NOS; 1-8, 13-16, or 23-24.

In another embodiment, a chimeric molecule comprises at least one *Salmonella* pathogenicity island 1 (SPI-1) and/or *Salmonella* pathogenicity island 2 (SPI-2) protein, peptides, variants, derivatives or combinations thereof. In some embodiments, the SPI-1 proteins, peptides, derivatives or variants thereof, are SipD and SipB. In other embodiments, the SPI-2 protein, peptides, derivatives or variants thereof are SseB and SseC. In an embodiment, a chimeric molecule comprises a SipD protein, peptide, derivatives or variants thereof, connected to a SipB protein, peptide or variants thereof. In another embodiment, the chimeric molecule comprises an SseB protein, peptide, derivatives or variants thereof, connected to an SseC protein, peptide, derivatives or variants thereof.

In one embodiment, the chimeric molecule comprises a molecule having at about 50% sequence identity to SEQ ID NOS: 1-8, 13-16, or 23-24. In other embodiments the chimeric molecule comprises any one of SEQ ID NOS: 1-8, 13-16, or 23-24.

In yet another embodiment, a chimeric molecule comprises a nucleic acid sequence encoding at least one *Salmonella* pathogenicity island 1 (SPI-1) and/or *Salmonella* pathogenicity island 2 (SPI-2) protein, peptides, variants, derivatives or combinations thereof. In an embodiment, the SPI-1 nucleic acid sequence encodes for SipD and/or SipB proteins, peptides, derivatives or variants thereof. In another embodiment, the SPI-2 nucleic acid sequence encodes for SseB and/or SseC protein, peptides, derivatives or variants thereof.

In another embodiment, a chimeric molecule comprises a nucleic acid sequence encoding at least one *Salmonella* pathogenicity island 1 (SPI-1) and at least one *Salmonella* pathogenicity island 2 (SPI-2) protein, peptides, derivatives, variants or combinations thereof. Preferably, the SPI-1 and SPI-2 protein, peptides, derivatives or variants comprise SipD, SipB, SseB, or SseC.

In another embodiment, a vaccine formulation comprises a therapeutically effective amount of a first chimeric molecule and a second chimeric molecule in a pharmaceutically acceptable carrier, the first chimeric molecule comprising at least one *Salmonella* pathogenicity island 1 (SPI-1) molecule linked or connected to at least one SPI-1 molecule; the second chimeric molecule comprising at least one *Salmonella* pathogenicity island 2 (SPI-2) linked or connected to at least one SPI-2 molecule. In one embodiment, the at least one SPI-1 molecule is connected to an SPI-2 molecule.

In certain embodiments, the SPI-1 and/or SPI-2 molecules of the invention can be administered to cells as a single protein containing SipD, SipB, SseB, or SseC (or active domains thereof), separated by a cleavable linker. Examples of cleavable linkers are known in the art (see, e.g., U.S. Pat. Nos. 5,258,498 and 6,083,486.)

Modified polypeptides: The invention is not limited to wild type SPI-1 and SPI-2 molecules but includes without limitation, allelic variants, species variants, splicing variants, mutants, fragments, and the like.

In an embodiment, SPI-1 and SPI-2 includes the peptide itself, chemical equivalents thereto, isomers thereof (e.g., isomers, stereoisomers, retro isomers, retro-inverso isomers; all-[D] isomers, all-[L] isomers, or mixed [L] and [D] isomers thereof), conservative substitutions therein, precursor forms thereof, endoproteolytically-processed forms thereof, such as cleavage of single amino acids from N or C terminals or immunologically active metabolites of the peptides of the invention, pharmaceutically-acceptable salts and esters thereof, and other forms resulting from post-translational modification. Also included is any parent sequence, up to and including 10, 9, 8, 7, 6, 5 and 4 amino acids in length (cyclized, or linear, or branched from the core parent sequence), for which the specified sequence is a subsequence. A person skilled in the art would appreciate that where the peptide can be a monomer, dimer, a trimer, etc. The uses of the peptides of the present invention include use of peptides wherein the active fragment or fragments are complexed to one or more binding partners. Modified peptides which retain the activity of the peptides of the invention are encompassed within the scope of the present invention.

In another embodiment, SPI-1 and SPI-2 peptides, or antigenic domains thereof, comprise at least one non-native amino acid residue or a non-amino acid molecule. A "non-native" amino acid residue comprises any change to an amino acid which is encoded by the SPI-1 and SPI-2 nucleic acid sequences. Thus, a non-native amino acid residue or non-amino acid molecule comprises, without limitation: a chemical equivalent, analog, synthetic molecule, derivative, variant, substitution, peptide nucleic acid, a linker molecule, inorganic molecule etc.

The mutations can be introduced at the nucleic acid level or at the amino acid level. With respect to particular nucleic acid sequences, because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. If mutations at the nucleic acid level are introduced to encode a particular amino acid, then one or more nucleic acids are altered. For example proline is encoded by CCC, CCA, CCG, CCU; thus, one base change, e.g. CCC (proline) to GCC gives rise to alanine. Thus by way of example every natural or non-natural nucleic acid sequence herein which encodes a natural or non-natural polypeptide also describes every possible silent variation of the natural or non-natural nucleic acid. One of skill will recognize that each codon in a natural or non-natural nucleic acid (except AUG, which is ordinarily the only codon for methionine, and TGG, which is ordinarily the only codon for tryptophan) can be modified to yield a functionally identical molecule or a different molecule. Accordingly, each silent variation of a natural and non-natural nucleic acid which encodes a natural and non-natural polypeptide is implicit in each described sequence.

As to amino acid sequences, individual substitutions, deletions or additions to a nucleic acid, peptide, polypeptide, or protein sequence which alters, adds or deletes a single natural and non-natural amino acid or a small percentage of natural and non-natural amino acids in the encoded sequence, the alteration results in the deletion of an amino acid, addition of an amino acid, or substitution of a natural and non-natural amino acid with a chemically similar amino acid. Conservative substitution tables providing functionally similar natural amino acids are well known in the art. Such conservatively modified variants are in addition to and do not exclude polymorphic variants, interspecies homologs, and alleles of the methods and compositions described herein.

A "non-natural amino acid" refers to an amino acid that is not one of the 20 common amino acids or pyrolysine or selenocysteine. Other terms that may be used synonymously with the term "non-natural amino acid" is "non-naturally encoded amino acid," "unnatural amino acid," "non-naturally-occurring amino acid," and variously hyphenated and non-hyphenated versions thereof. The term "non-natural amino acid" includes, but is not limited to, amino acids which occur naturally by modification of a naturally encoded amino acid (including but not limited to, the 20 common amino acids or pyrrolysine and selenocysteine) but are not themselves incorporated, without user manipulation, into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phosphotyrosine. Additionally, the term "non-natural amino acid" includes, but is not limited to, amino acids which do not occur naturally and may be obtained synthetically or may be obtained by modification of non-natural amino acids.

In some cases, the non-natural amino acid substitution(s) or incorporation(s) will be combined with other additions, substitutions, or deletions within the polypeptide to affect other chemical, physical, pharmacologic and/or biological traits. In some cases, the other additions, substitutions or deletions may increase the stability (including but not limited to, resistance to proteolytic degradation) of the polypeptide or increase affinity of the polypeptide for its appropriate receptor, ligand and/or binding proteins. In some cases, the other additions, substitutions or deletions may increase the solubility of the polypeptide. In some embodiments sites are selected for substitution with a naturally encoded or non-natural amino acid in addition to another site for incorporation of a non-natural amino acid for the purpose of increasing the polypeptide solubility following expression in recombinant host cells. In some embodiments, the polypeptides comprise another addition, substitution, or deletion that modulates affinity for the associated ligand, binding proteins, and/or receptor, modulates (including but not limited to, increases or decreases) receptor dimerization, stabilizes receptor dimers, modulates circulating half-life, modulates release or bio-availability, facilitates purification, or improves or alters a particular route of administration. Similarly, the non-natural amino acid polypeptide can comprise chemical or enzyme cleavage sequences, protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification, transport thru tissues or cell membranes, prodrug release or activation, size reduction, or other traits of the polypeptide.

The methods and compositions described herein include incorporation of one or more non-natural amino acids into a polypeptide. One or more non-natural amino acids may be incorporated at one or more particular positions which do not disrupt activity of the polypeptide. This can be achieved by making "conservative" substitutions, including but not limited to, substituting hydrophobic amino acids with non-natural or natural hydrophobic amino acids, bulky amino acids with non-natural or natural bulky amino acids, hydrophilic amino acids with non-natural or natural hydrophilic amino acids) and/or inserting the non-natural amino acid in a location that is not required for activity.

A variety of biochemical and structural approaches can be employed to select the desired sites for substitution with a non-natural amino acid within the polypeptide. Any position of the polypeptide chain is suitable for selection to incorporate a non-natural amino acid, and selection may be based on rational design or by random selection for any or no particular desired purpose. Selection of desired sites may be based on producing a non-natural amino acid polypeptide (which may be further modified or remain unmodified) having any desired property or activity, binding partner conformation modulators, dimer or multimer formation, no change to activity or property compared to the native molecule, or manipulating any physical or chemical property of the polypeptide such as solubility, aggregation, or stability. For example, locations in the polypeptide required for antigenicity of a polypeptide can be identified using methods including, but not limited to, point mutation analysis, alanine scanning or homolog scanning methods. Residues other than those identified as critical to biological activity by methods including, but not limited to, alanine or homolog scanning mutagenesis may be good candidates for substitution with a non-natural amino acid depending on the desired activity sought for the polypeptide. Alternatively, the sites identified as critical to biological activity may also be good candidates for substitution with a non-natural amino acid, again depending on the desired activity sought for the polypeptide. Another alternative would be to make serial substitutions in each position on the polypeptide chain with a non-natural amino acid and observe the effect on the activities of the polypeptide. Any means, technique, or method for selecting a position for substitution with a non-natural amino acid into any polypeptide is suitable for use in the methods, techniques and compositions described herein.

The structure and activity of naturally occurring mutants of a polypeptide that contain deletions can also be examined to determine regions of the protein that are likely to be tolerant of substitution with a non-natural amino acid. Once residues that are likely to be intolerant to substitution with non-natural amino acids have been eliminated, the impact of proposed substitutions at each of the remaining positions can be examined using methods including, but not limited to, the three-dimensional structure of the relevant polypeptide, and any associated ligands or binding proteins. X-ray crystallographic and NMR structures of many polypeptides are available in the Protein Data Bank (PDB, www.resb.org), a centralized database containing three-dimensional structural data of large molecules of proteins and nucleic acids, one can be used to identify amino acid positions that can be substituted with non-natural amino acids. In addition, models may be made investigating the secondary and tertiary structure of polypeptides, if three-dimensional structural data is not available. Thus, the identity of amino acid positions that can be substituted with non-natural amino acids can be readily obtained. Exemplary sites of incorporation of a non-natural amino acid include, but are not limited to, those that are excluded from potential receptor binding regions, or regions for binding to binding proteins or ligands may be fully or partially solvent exposed, have minimal or no hydrogen-bonding interactions with nearby residues, may be minimally exposed to nearby reactive residues, and/or may be in regions that are highly flexible as predicted by the three-dimensional crystal structure of a particular polypeptide with its associated receptor, ligand or binding proteins.

A wide variety of non-natural amino acids can be substituted for, or incorporated into, a given position in a polypeptide. By way of example, a particular non-natural amino acid may be selected for incorporation based on an examination of the three dimensional crystal structure of a polypeptide with its associated ligand, receptor and/or binding proteins e.g. immunoglobulins, a preference for conservative substitutions As further used herein, a "chemical equivalent" of a peptide of the invention is a molecule which possesses the same desired activity, e.g. immunological activity, as peptides described herein, and exhibits a trivial chemical different, or a molecule which is converted, under mild conditions, into a peptide of the invention (e.g., esters, ethers, reduction products, and complexes of the peptides of the invention).

The term "analogue", as used herein, includes any peptide having an amino acid sequence substantially identical to a sequence described herein, in which at least one residue has been conservatively substituted with a functionally-similar residue. An "analogue" includes functional variants and obvious chemical equivalents of an amino acid sequence of SPI-1 and SPI-2 peptides, or functional domains thereof. As further used herein, the term "functional variant" refers to the activity of a peptide that demonstrates an ability to signal; interacting with one or more molecules; activating a transcription pathway, etc. An "analogue" further includes any pharmaceutically-acceptable salt of an analogue as described herein.

A "derivative", as used herein, refers to a peptide of the invention having one or more amino acids chemically derivatized by reaction of a functional side group. Exemplary derivatized molecules include, without limitation, peptide molecules in which free amino groups have been derivatized to form salts or amides, by adding acetyl groups, amine hydrochlorides, carbobenzoxy groups, chloroacetyl groups, formyl groups, p-toluene sulfonyl groups, or t-butyloxycarbonyl groups. Free hydroxyl groups may be derivatized to form O-acyl or O-alkyl derivatives. Furthermore, free carboxyl groups may be derivatized to form salts, esters (e.g methyl and ethyl esters), or hydrazides. Thus, a "derivative" further includes any pharmaceutically-acceptable salt of a derivative as described herein.

The peptides embodied herein, can a modified C-terminus and/or a modified N-terminus. For example, an amidated C-terminus, the amino terminus can be acetylated (Ac) or the carboxy terminus can be amidated ($NH_2$). However, the peptides of the invention are preferably not acetylated if such a modification would result in loss of desired immunological activity. Amino terminus modifications include methylating (i.e., —NHCH, or —$NH(CH)_2$, acetylating, adding a carbobenzoyl group, or blocking the amino terminus with any blocking group containing a carboxylate functionality defined by RCOO—, where R is selected from the group consisting of naphthyl, acridinyl, steroidyl, and similar groups. Carboxy terminus modifications include replacing the free acid with a carboxamide group or forming a cyclic lactam at the carboxy terminus to introduce structural constraints.

In one embodiment backbone substitutions can be made, such as NH to NCH; The SPI-1 and SPI-2 peptides may also be a modification (e.g., a point mutation, such as an insertion or a deletion, or a truncation). By way of example, the peptide may comprise an amino acid sequence comprising a modified residue by at least one point insertion of a D amino acid as long as desired immunogenicity is retained. In particular, proline analogs in which the ring size of the proline residue is changed from 5 members to 4, 6, or 7 members can be employed. Cyclic groups can be saturated or unsaturated, and if unsaturated, can be aromatic or non-aromatic.

In another embodiment, the naturally occurring side chains of the 20 genetically encoded amino acids (or D amino acids) are replaced with other side chains with similar properties, for instance with groups such as alkyl, lower alkyl, cyclic 4-, 5-, 6-, to 7-membered alkyl amide, amide lower alkyl amide di(lower alkyl), lower alkoxy, hydroxy, carboxy and the lower ester derivatives thereof, and with 4-, 5-, 6-, to 7-membered heterocyclic.

Such substitutions can include but are not necessarily limited to: (1) non-standard, positively charged amino acids, like: ornithine, Nlys; N-(4-aminobutyl)-glycine which has the lysine side chain attached to the "N-terminus" and compounds with aminopropyl or aminoethyl groups attached to the amino group of glycine. (2). Non-naturally occurring amino acids with no net charge and side-chains similar to arginine, such as, Cit: citrulline and Hei; citrulline with one more methylene group; (3) non-standard non-naturally occurring amino acids with OH (e.g., like serine), such as, hSer; homoserine (one more methylen group, Hyp; hydroxyproline, Val (BOH); hydroxyvaline, Pen; penicillamin, (Val (BSH); (4) proline derivatives, such as, D-Pro, such as, 3,4-dehydroproline, Pyr; pyroglutamine (proline with C═O) in ring), Proline with fluorine substitutions on the ring, 1,3-thiazolidine-+carboxylic acid (proline with S in ring); (5) Histidine derivative, such as, Thi; beta-(2-thienyl)-alanine; or (6) alkyl derivatives, such as, Abu; 2-aminobutyric acid (ethyl group on Cα), Nva; norvaline (propyl group on Ca), Nle; norleucine (butyl group on Cα), Hol; homoleucine (propyl group on Cα), Aib, alpha-aminoisobutyric acid (valine without methylene group). A person skilled in the art would appreciate that those substitutions that retain the activity of the parent peptide/sequence.

In another alternative embodiment, the C-terminal carboxyl group or a CHterminal ester can be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride ($CH_2Cl_2$), dimethyl formamide (DMF) mixtures. The cyclic peptide is then formed by internal displacement of the activated ester with the N-terminal amine. Internal cyclization as opposed to polymerization can be enhanced by use of very dilute solutions. Such methods are well known in the art.

The peptides of the invention can be cyclized, or a desamino or descarboxy residue at the termini of the peptide can be incorporated, so that there is no terminal amino or carboxyl group, to decrease susceptibility to proteases or to restrict the conformation of the peptide. C-terminal functional groups of the compounds of the present invention include amide, amide lower alkyl, amide di(lower alkyl), lower alkoxy, hydroxy, and carboxy, and the lower ester derivatives thereof, and the pharmaceutically acceptable salts thereof.

The peptides of the invention can be cyclized by adding an N and/or C terminal cysteine and cyclizing the peptide through disulfide linkages or other side chain interactions.

A desamino or descarboxy residue at the termini of the peptide can be incorporated, so that there is no terminal amino or carboxyl group, to decrease susceptibility to proteases or to restrict the conformation of the peptide.

Mutant polypeptides, e.g. SPI-1 and SPI-2, molecules comprising SipD, SipB, SseB or SseC or antigenic domains thereof, can be assessed in one or more of the assays described herein. The polypeptides can include amino acid residues (naturally occurring, synthetic, analogs, derivatives, or modified (e.g., glycosylated or phosphorylated residues) that are linked by a peptide bond.

In addition to containing one or more mutations, a polypeptide of the invention can be substantially pure (i.e., separated from one or more of the components that naturally accompany the polypeptide). Typically, a polypeptide is substantially pure when it is at least 60%, by weight, free from naturally occurring organic molecules. Alternatively, the preparation can be at least 75%, at least 90%, or at least 99%, by weight, of mutant polypeptide. A substantially pure mutant polypeptide can be obtained, for example, by expression of a recombinant nucleic acid encoding a mutant polypeptide, e.g. SipD. SipB, SseB or SseC, or by chemically synthesizing the polypeptide. Purity can be measured by any appropriate method, including column chromatography, polyacrylamide gel electrophoresis, or HPLC analysis. Polypeptides that are derived from eukaryotic organisms but synthesized in E. coli, or other prokaryotes, and polypeptides that are chemically synthesized will be substantially free from their naturally associated components.

A wild type SipD, SipB, SseB or SseC can be a polypeptide that is identical to the naturally occurring SipD, SipB, SseB or SseC polypeptide. A mutant polypeptide can be a polypeptide or portion thereof having at least one mutation relative to the wild-type molecule.

Mutations in polypeptides can be effected in many following ways, for example: deletion of one or more of the amino acids, addition of one or more amino acids, or substitution of one or more of the amino acids. In the event the mutation is a substitution, the substitution can be a conservative or non-conservative substitution, Non-conservative substitutions occur when one amino acid residue in a polypeptide sequence is replaced by another amino acid that has a different physical property (e.g., a different size, charge, or polarity) as the amino acid being replaced. For example, substitution of a non-aromatic amino acid in the place of an aromatic amino acid (e.g., substitution of an alanine in the place of tryptophan) is an example of a non-conservative substitution. Alternately, the substitution can be a conservative amino acid substitution. A conservative substitution can be the replacement of one amino acid in a polypeptide sequence by another amino acid, wherein the replacement amino acid has similar physical properties (e.g., size, charge, and polarity) as the amino acid being replaced. For example, replacing one aromatic amino acid with another aromatic amino acid can be a conservative substitution. Some typical examples of conservative amino acid substitutions include substitutions with the following groups: glycine and alanine; valine, isoleucine, and leucine: aspartic acid and glutamic acid; asparagine and glutamine; serine and threonine; lysine and arginine; and phenylalanine and tyrosine. The substitution can be, for example, a non-aromatic amino acid substitution. The substitution can also be at the corresponding position of a polypeptide from another species (for example, a domesticated animal such as a cow, pig, sheep, rabbit, goat, dog or cat). The term "conservative substitutions", as defined herein, includes substitutions having an inconsequential effect on the ability of the peptide of the invention to enhance innate immunity.

The polypeptides described herein can include a heterologous (i.e., non-SipD, -SipB, -SseB or -SseC) sequence.

Polynucleotide: A mutant polypeptide, whether alone or as a part of a chimeric polypeptide, can be encoded by a nucleic acid molecule, and substantially pure nucleic acid molecules that encode the mutant polypeptides described herein are within the scope of the invention. The nucleic acid can be a molecule of genomic DNA, cDNA, synthetic DNA, or RNA. The nucleic acid molecule encoding, for example, a SipD, SipB, SseB or SseC polypeptide will be at least 65%, at least 75%, at least 85%, or at least 95% (e.g., 99%) identical to the nucleic acid encoding wild-type molecules. For nucleic acids, the length of comparison sequences will generally be at least 50 nucleotides, preferably at least 60 nucleotides, more preferably at least 75 nucleotides, and most preferably 10 nucleotides.

The polynucleotides e.g. SPI-1 and SPI-2 molecules comprising SipD, SipB, SseB or SseC can also comprise modifications. Examples of some modified polynucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. In some embodiments, modified SPI-1 and SPI-2 polynucleotides comprise those with phosphorothioate backbones and those with heteroatom backbones, $CH_2$—NH—O—$CH_2$, $CH_2$—N($CH_3$)—O—$CH_2$ [known as a methylene (methylimino) or MMI backbone], $CH_2$—O—N($CH_3$)—$CH_2$, $CH_2$—N ($CH_3$)—N($CH_3$)—CH, and O—N($CH_3$)—$CH_2$—$CH_2$ backbones, wherein the native phosphodiester backbone is represented as O—P—O—CH). The amide backbones disclosed by De Mesmaeker et al. Acc. Chem. Res. 1995, 28:366-374) are also embodied herein. In some embodiments, the oligonucleotides having morpholino backbone structures (Summerton and Weller, U.S. Pat. No. 5,034,506), peptide nucleic acid (PNA) backbone wherein the phosphodiester backbone of the oligonucleotide is replaced with a polyamide backbone, the nucleobases being bound directly or indirectly to the aza nitrogen atoms of the polyamide backbone (Nielsen et al. Science 1991, 254, 1497). Oligonucleotides may also comprise one or more substituted sugar moieties. Oligonucleotides may also have sugar mimetics such as cyclobutyls in place of the pentofuranosyl group.

Polynucleotides may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (L). Modified nucleobases include nucleobases found only infrequently or transiently in natural nucleic acids, e.g., hypoxanthine, 6-methyladenine, S-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino) adenine, 2-(imidazolylalkyl) adenine, 2-(aminoalklyamino) adenine or other heterosubstituted alkyladenines, 2-thiouracil, 2-thiothymine, 5-bromouracil, 5-hydroxymethyluracil, 8-azaguanine, 7-deazaguanine, No (6-aminohexyl) adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are presently preferred base substitutions.

Another modification of the polynucleotides of the invention involves chemically linking to the polynucleotide, one or more moieties or conjugates which enhance the activity of cellular uptake of the polynucleotide. Such moieties include but are not limited to lipid moieties such as a cholesterol moiety, a cholesteryl moiety (Letsinger et al., *Proc. Natl. Acad. Sci. USA* 1989, 86, 6553), cholic acid (Manoharan et al. *Bioorg, Med. Chem. Let.* 1994, 4, 1053), a thioether, e.g., hexyl-S-tritylthiol (Manoharan et al. *Ann. N.Y. Acad. Sci.* 1992, 660, 306; Manoharan et al. *Bioorg. Med. Chem. Let.* 1993, 3, 2765), a thiocholesterol (Oberhauser et al., *Nucl. Acids Res.* 1992, 20, 533), an aliphatic chain, e.g., dodecandiol or undecyl residues (Saison-Behmoaras et al. *EMBO J.* 1991, 10, 111; Kabanov et al. *FEBS Lett.* 1990, 259, 327; Svinarchuk et al. *Biochimie* 1993, 75, 49), a phospholipid, e.g., di-hexadecyl-rac-glycerol or triethylammonium 1,2-di-O-hexadecyl-rac-glycero-3-H-phosphonate (Manoharan et al. *Tetrahedron Lett.* 1995, 36, 3651; Shea et al. *Nucl. Acids Res.* 1990, 18, 3777), a polyamine or a polyethylene glycol chain (Manoharan et al. *Nucleotides & Nucleotides* 1995, 14, 969), or adamantane acetic acid (Manoharan et al. *Tetrahedron Lett.* 1995, 36, 3651). Polynucleotides comprising lipophilic moieties and methods for preparing such polynucleotides are known in the art, for example, U.S. Pat. Nos. 5,138,045, 5,218,105 and 5,459,255.

It is not necessary for all positions in a given polynucleotide to be uniformly modified, and in fact more than one of the aforementioned modifications may be incorporated in a single polynucleotide or even at within a single nucleoside within a polynucleotide. The present invention also includes polynucleotides which are chimeric polynucleotides as hereinbefore defined.

Vectors Expressing SP1-1 and/or SPI-2 Molecules

Also encompassed are vectors which contain such nucleic acid sequences (e.g. plasmids, cosmida, various expression vectors, etc.), and host cells such as bacteria, insect cells, etc., which comprise the nucleic acid sequences and/or the vectors. Such vectors typically include one or more expressible gene sequences encoding one or more or the proteins/polypeptides/peptides of interest, operably linked to at least one transcription element (e.g. a promoter) that drives expression of the gene. The vectors may be used for production of the proteins/fragments thereof, or may be used as a vaccinating agent, i.e. the invention also encompasses nucleic acid vaccines. Those of skill in the art are aware of the many protocols for preparing and administering nucleic acid vaccines, such as those described in issued U.S. Pat. Nos. 7,927,870 and 7,094,410, the complete contents of which are hereby incorporated by referenced in entirety. Sequence identity may be determined in various ways that are within the skill in the art, e.g., using publicly available computer software such as BLAST, BLAST-2, ALIGN or Megalign (DNASTAR) software, which are used to perform sequence alignments and then calculate sequence identity. Exemplary software programs available from the National Center for Biotechnology Information (NCBI) on the website nebi.nlm.nih.gov include blastp, blastn, blastx, tblastn and tblastx. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are used at the default settings. The default scoring matrix used by blastp, blastx, tblastn, and tblastx is the BLOSUM62 matrix (Henikoff et al, (1992) *Proc. Natl. Acad, Sci, USA* 89; 10915-10919). In one approach, the percent identity can be determined using the default parameters of blastp, version 2.2.26 available from the NCBI In a preferred embodiment, an expression vector comprises a nucleic acid molecule with a sequence encoding polypeptides described herein. The vector can be capable of directing expression of a SipD, SipB, SseB or SseC polypeptide in, for example, a cell that has been transduced with the vector. These vectors can be viral vectors, such as retroviral, adenoviral, or adenoviral-associated vectors, as well as plasmids or cosmids. Prokaryotic or eukaryotic cells that contain and express DNA encoding any of the molecules comprising SipD. SipB. SseB or SseC; mutant SipD, SipB, SseB or SseC; SipD, SipB, SseB or SseC antigenic epitopes, fusion peptides (e.g. SEQ ID NOS: 14 and 16) etc. are also features of the invention. The method of transduction, the choice of expression vector, and the host cell may vary. The precise components of the expression system are not critical. It matters only that the components are compatible with one another, a determination that is well within the abilities of skilled artisans. Furthermore, for guidance in selecting an expression system, skilled artisans may consult Ausubel et al., Current Protocols in Molecular Biology (1993, John Wiley and Sons, New York, N.Y.) and Pouwels et al., Cloning Vectors: A Laboratory Manual (1987). The vector can also have a sequence that encodes a detectable marker, such as β-galactosidase, α-glucuronidase (GUS), luciferase, horseradish peroxidase (HRP), alkaline phosphatase, acetylcholinesterase, or chloramphenicol acetyl transferase. Fluorescent reporter genes include, but are not limited to, green fluorescent protein (GFP), red fluorescent protein (RFP), cyan fluorescent protein (CFP), and blue fluorescent protein (BFP). The detectable marker can also be an epitope tag, such as a myc, FLAG, or HA tag.

In an embodiment, a vector comprises one or more polynucleotides comprising SEQ ID NOS: 1-8, 13-16, or 23-24, variants, mutants, derivatives or fragments thereof. The vector can be administered to a patient wherein expression of SEQ ID NOS: 1-8, 13-16, or 23-24, variants, mutants, derivatives or fragments thereof, induce response. A number of vectors are known to be capable of mediating transfer of gene products to mammalian cells, as is known in the art and described herein. A "vector" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest in gene therapy. Vectors include, for example, viral vectors (such as adenoviruses ("Ad"), adeno-associated viruses (AAV), and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Other vectors include those described by Chen et al, *BioTechniques,* 34:167-171 (2003). Large varieties of such vectors are known in the art and are generally available.

A "recombinant viral vector" refers to a viral vector comprising one or more heterologous gene products or sequences. Since many viral vectors exhibit size-constraints associated with packaging, the heterologous gene products or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying gene products necessary for replication and/or encapsidation). Modified viral vectors in which a polynucleotide to be delivered is carried on the outside of the viral particle have also been described (see, e.g., Curiel, D T, et al. PNAS 88:8850-8854, 1991).

Suitable nucleic acid delivery systems include viral vector, typically sequence from at least one of an adenovirus, adenovirus-associated virus (AAV), helper-dependent adenovirus, retrovirus, or hemagglutinating virus of Japan-liposome (HVJ) complex. Preferably, the viral vector comprises a strong eukaryotic promoter operably linked to the polynucleotide e.g., a cytomegalovirus (CMV) promoter:

Additionally preferred vectors include viral vectors, fusion proteins and chemical conjugates. Retroviral vectors include Moloney murine leukemia viruses and HIV-based viruses. One HIV-based viral vector comprises at least two vectors wherein the gag and pol genes are from an HIV genome and the eny gene is from another virus. DNA viral vectors are preferred. These vectors include pox vectors such as orthopox or avipox vectors, herpesvirus vectors such as a herpes simplex I virus (HSV) vector [Geller, A. L. et al., *J. Neurochem,* 64:487 (1995); Lim. F., et al., in DNA Cloning: Mammalian Systems, D. Glover, Ed. (Oxford Univ. Press, Oxford England) (1995); Geller, A. L. et al., *Proc Natl. Acad. Sci. U.S.A.:* 90 7603 (1993); Geller, A. L, et al., *Proc Natl, Acad. Sci USA:* 87:1149 (1990)], Adenovirus Vectors [LeGal LaSalle et al., *Science,* 259:988 (1993); Davidson, et al., *Nat. Genet.* 3:219 (1993); Yang, et al., *J. Virol.* 69:2004 (1995)] and Adeno-associated Virus Vectors [Kaplitt, M. G., et al., *Nat. Genet,* 8:148 (1994)].

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors may be an indication for some invention embodiments. The adenovirus vector results in a shorter term expression (e.g., less than about a month) than adeno-associated virus, in some embodiments, may exhibit much longer expression. The particular vector chosen will depend upon the target cell and the condition being treated. The selection of appropriate promoters can readily be accomplished. Preferably, one would use a high expression promoter. An example of a suitable promoter is the 763-base-pair cytomegalovirus (CMV) promoter. The Rous sarcoma virus (RSV) (Davis, et al., *Hum Gene Ther* 4:151 (1993)) and MMT promoters may also be used. Certain proteins can expressed using their native promoter. Other elements that can enhance expression can also be included such as an enhancer or a system that results in high levels of expression such as a tat gene and tar element. This cassette can then be inserted into a vector, e.g., a plasmid vector such as, pUC19, pUC118, pBR322, or other known plasmid vectors, that includes, for example, an *E. coli* origin of replication. See, Sambrook, et al., Molecular Cloning: A Laboratory Manual, Cold Spring Harbor Laboratory press, (1989). The plasmid vector may also include a selectable marker such as the β-lactamase gene for ampicillin resistance, provided that the marker polypeptide does not adversely affect the metabolism of the organism being treated. The cassette can also be bound to a nucleic acid binding moiety in a synthetic delivery system, such as the system disclosed in WO 95/22618.

If desired, the polynucleotides of the invention may also be used with a microdelivery vehicle such as cationic liposomes and adenoviral vectora. For a review of the procedures for liposome preparation, targeting and delivery of contents, see Mannino and Gould-Fogerite, *BioTechniques,* 6:682 (1988). See also, Felgner and Holm, Bethesda Res. Lab. Focus, 11 (2): 21 (1989) and Maurer, R. A., Bethesda Res. Lab. Focus, 11 (2): 25 (1989).

Replication-defective recombinant adenoviral vectors, can be produced in accordance with known techniques. See, Quantin, et al., *Proc. Natl, Acad. Sci. USA,* 89:2581-2584 (1992); Stratford-Perricadet, et al., *J. Clin. Invest.,* 90:626-630 (1992); and Rosenfeld, et al., *Cell,* 68:143-155 (1992).

Another delivery method is to use single stranded DNA producing vectors which can produce the SPI-1 and/or SPI-2 molecules intracellularly. See for example, Chen et al. *BioTechniques,* 34:167-171 (2003), which is incorporated herein, by reference, in its entirety.

Expression of SPI-1 and/or SPI-2 molecules may be controlled by any promoter/enhancer element known in the art, but these regulatory elements must be functional in the host selected for expression. Promoters which may be used to control gene expression include, but are not limited to, cytomegalovirus (CMV) promoter (U.S. Pat. Nos. 5,385,839 and 5,168,062), the SV40 early promoter region (Benoist and Chambon, 1981, *Nature* 290:304-310), the promoter contained in the 3' long terminal repeat of Rous sarcoma virus (Yamamoto, et al., *Cell* 22:787-797, 1980), the herpes thymidine kinase promoter (Wagner et al., *Proc. Natl. Acad. Sci. U.S.A.* 78:1441-1445, 1981), the regulatory sequences of the metallothionein gene (Brinster et al., *Nature* 96 39-42, 1982); prokaryotic expression vectors such as the β-lactamase promoter (Villa-Kamaroff, et al., *Proc. Natl. Acad. Sci. U.S.A.* 75:3727-3731, 1978), or the tac promoter (DeBoer, et al., *Proc. Natl. Acad. Sci. U.S.A.* 80:21-25, 1983); promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., *Cell* 38:639-

646, 1984; Ornitz et al., Cold Spring Harbor Symp. *Quant. Biol.* 50:399-409, 1986; MacDonald, *Hepatology* 7:425-515, 1987); insulin gene control region which is active in pancreatic beta cells (Hanahan, *Nature* 315:115-122, 1985), immunoglobulin gene control region which is active in lymphoid cells (Grosschedl et al., *Cell* 38:647-658, 1984; Adames et al., *Nature* 318:533-538, 1985; Alexander et al., *Mol. Cell. Biol,* 7:1436-1444, 1987), mouse mammary tumor virus control region which is active in testicular, breast, lymphoid and mast cells (Leder et al., *Cell* 45:485-495, 1986), albumin gene control region which is active in liver (Pinkert et al., *Genes and Devel.* 1:268-276, 1987), alpha-fetoprotein gene control region which is active in liver (Krumlauf et al., *Mol, Cell. Biol.* 5:1639-1648, 1985; Hammer et al., *Science* 235:53-58, 1987), alpha I-antitrypsin gene control region which is active in the liver (Kelsey et al., *Genes and Devel,* 1:161-171, 1987), beta-globin gene control region which is active in myeloid cells (Mogram et al., *Nature* 315:338-340, 1985; Kollias et al., *Cell* 46:89-94, 1986), myelin basic protein gene control region which is active in oligodendrocyte cells in the brain (Readhead et al., *Cell* 48:703-712, 1987), myosin light chain-2 gene control region which is active in skeletal muscle (Sani, *Nature* 314:283-286, 1985), and gonadotropic releasing hormone gene control region which is active in the hypothalamus (Mason et al., *Science* 234:1372-1378, 1986).

A wide variety of host/expression vector combinations may be employed in expressing the nucleic acid sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMal-C2, pET, pGEX, pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the 2μ plasmid or derivatives thereof, vectors useful in eukaryotic cells, such as vectors useful in insect or mammalian cells; vectors derived from combinations of plasmids and phage DNAs, such as plasmids that have been modified to employ phage DNA or other expression control sequences; and the like.

Yeast expression systems can also be used according to the invention to express SPI-1 and/or SPI-2 molecules. For example, the non-fusion pYES2 vector (XbaI, SphI, ShoI, NotI, GstXI, EcoRI, BstXI, BamHI, SaeI, KpnI, and HindIII cloning sites; Invitrogen) or the fusion pYESHisA, B, C (XbaI, SphI, ShoI, NotI, BstXI, EcoRI, BamHI, SacI, KpnI, and HindIII cloning sites, N-terminal peptide purified with ProBond resin and cleaved with enterokinase; Invitrogen), to mention just two, can be employed according to the invention. A yeast two-hybrid expression system can be prepared in accordance with the invention.

In certain embodiments, a single DNA construct expressing SPI-1 and/or SPI-2 molecules as two separate genes can be introduced into a cell or subject. In certain embodiments, a single DNA construct expressing SipD, SipB, SseB, or SseC as four separate genes can be introduced into a cell or subject. Exemplary expression constructs can be formulated as a pharmaceutical composition, e.g., for administration to a subject. DNA constructs and the therapeutic use of such constructs are well known to those of skill in the art (see, e.g. Chiarella et al. (2008) Recent Patents Anti-Infect, Drug Disc. 3:93-101; Gray et al. (2008) *Expert Opin. Biol. Ther.* 8:911-922; Melman et al. (2008) *Hum. Gene Ther.* 17:1165-1176). Naked DNA constructs typically include one or more therapeutic nucleic acids and a promoter sequence. A naked DNA construct can be a DNA vector, commonly referred to as pDNA. Naked DNA typically does not integrate into chromosomal DNA. Generally, naked DNA constructs do not require, or are not used in conjunction with, the presence of lipids, polymers, or viral proteins. Such constructs may also include one or more of the non-therapeutic components.

DNA vectors are known in the art and typically are circular double stranded DNA molecules. DNA vectors usually range in size from three to five kilo-base pairs (e.g., including inserted therapeutic nucleic acids). Like naked DNA, DNA vectors can be used to deliver and express one or more therapeutic proteins in target cells. DNA vectors do not integrate into chromosomal DNA.

Generally, DNA vectors include at least one promoter sequence that allows for replication in a target cell. Uptake of a DNA vector may be facilitated by combining the DNA vector with, for example, a cationic lipid, and forming a DNA complex. Typically, viral vectors are double stranded circular DNA molecules that are derived from a virus. Viral vectors typically are larger in size than naked DNA and DNA vector constructs and have a greater capacity for the introduction of foreign (i.e., not virally encoded) genes. Like naked DNA and DNA vectors, viral vectors can be used to deliver and express one or more therapeutic nucleic acids in target cells. Unlike naked DNA and DNA vectors, certain viral vectors stably incorporate themselves into chromosomal DNA. Typically, viral vectors include at least one promoter sequence that allows for replication of one or more vector encoded nucleic acids, e.g., a therapeutic nucleic acid, in a host cell. Viral vectors may optionally include one or more non-therapeutic components described herein. Advantageously, uptake of a viral vector into a target cell does not require additional components, e.g., cationic lipids. Rather, viral vectors transfect or infect cells directly upon contact with a target cell.

The approaches described herein include the use of retroviral vectors, adenovirus-derived vectors, and/or adeno-associated viral vectors as recombinant gene delivery systems for the transfer of exogenous genes in vivo, particularly into humans. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14, and other standard laboratory manuals.

Viruses that are used as transduction agents of DNA vectors and viral vectors such as adenoviruses, retroviruses, and lentiviruses may be used in practicing the present invention. Illustrative retroviruses include, but are not limited to: Moloney murine leukemia virus (M-MuLV), Moloney murine sarcoma virus (MoMSV), Harvey murine sarcoma virus (HaMuSV), marine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV) and lentivirus. As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; caprine arthritis-encephalitis virus (CABV); equine infectious anemia virus (EIAV); feline immunodeficiency virus (FIV); bovine immune deficiency virus (BIV); and simian immunodeficiency virus (SIV).

In certain embodiments, an adenovirus can be used in accordance with the methods described herein. The genome of an adenovirus can be manipulated such that it encodes and expresses a gene product of interest but is inactivated in terms of its ability to replicate in a normal lytic viral life cycle. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells. Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors.

Adeno-associated virus is a naturally occurring defective virus that requires another virus, such as an adenovirus or a herpes virus, as a helper virus for efficient replication and a productive life cycle. It is also one of the few viruses that may integrate its DNA into non-dividing cells, and exhibits a high frequency of stable integration.

In various embodiments, one or more viral vectors that expresses the SPI-1 and/or SPI-2 molecules encoding a polypeptide or polypeptides of the invention is administered by direct injection to a cell, tissue (e.g. i.m.), or organ of a subject, in vivo.

In some embodiments of the invention, it may be desirable to use a cell, cell type, cell lineage or tissue specific expression control sequence to achieve cell type specific, lineage specific, or tissue specific expression of the SPI-1 and/or SPI-2 polynucleotide sequences, for example SEQ ID NOS: 14, 16, to express a particular nucleic acid encoding a polypeptide in only a subset of cell types, cell lineages, or tissues, or during specific stages of development.

Certain embodiments of the invention provide conditional expression of the SPI-1 and/or SPI-2 polynucleotides of interest. For example, expression is controlled by subjecting a cell, tissue, organism, etc., to a treatment or condition that causes the polynucleotide to be expressed or that causes an increase or decrease in expression of the polynucleotide encoded by the polynucleotide of interest. Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the “GeneSwitch” mifepristone-regulatable system (Sirin et al, 2003, *Gene,* 323:67), the cumate inducible gene switch (WO 2002/088346), tetracycline-dependent regulatory systems, etc.

In certain embodiments, vectors comprise a selection gene, also termed a selectable marker. Typical selection genes encode proteins that (a) confer resistance to antibiotics or other toxins, e.g., ampicillin, neomycin, hygromycin, methotrexate, Zeocin, Blastocidin, or tetracycline, (b) complement auxotrophic deficiencies, or (c) supply critical nutrients not available from complex media, e.g., the gene encoding D-alanine racemase for Bacilli. Any number of selection systems may be used to recover transformed cell lines. These include, but are not limited to, the herpes simplex virus thymidine kinase (Wigler et al, (1977) *Cell,* 11:223-232) and adenine phosphoribosyltransferase (Lowy et al. (1990) *Cell,* 22:817-823) genes which can be employed in tk- or aprt-cells, respectively.

The vector may comprise any regulatory sequence allowing proper expression of the coding nucleic acid in a selected host cell, e.g., a promoter, terminator, polyA, origin of replication, integration region (e.g., homologous region), intron, UTR sequences, marker gene, etc.

In another preferred embodiment, an expression vector comprising a nucleic acid molecule as defined above is provided, including a signal peptide, operably linked to regulatory elements allowing expression of said nucleic acid in a mammalian host or host cell. Preferred regulatory elements include a promoter, which may be selected, without limitation, from viral, cellular and synthetic promoters, including constitutive, tissue-specific or regulated promoters, in particular from the group consisting of the CMV promoter, E1Fa promoter and metallothionein promoter. Further regulatory elements that may be contained within the vectors of this invention include, without limitation, a Bcl-2 gene, UTR sequences and MAR sequences.

The above nucleic acids and vectors may be used for instance to produce recombinant SipD, SipB, SseB or SseC polypeptides in various competent host or host cells, as well as for gene therapy purposes.

The vector may be a plasmid, virus, phage, cosmid, episome, etc. Preferred vectors are viral vectors (e.g., recombinant adenoviruses) and plasmids, which can be produced based on commercially available backbones, such as pBR, pcDNA, pUC, pET, pVITRO, etc. The vector typically comprises regulatory elements or sequences to control or mediate expression of a polypeptide. The regulatory sequences may be chosen from promoters, enhancers, silencers, tissue-specific signals, peptide signals, introns, terminators, polyA sequences, GC regions, etc., or a combination thereof. Such regulatory elements or sequences may be derived from mammalian, fungal, plant, bacterial, yeast, bacteriophage or viral genes, or from artificial sources. Useful promoters for prokaryote expression (such as *E. coli*) include T7 RNA polymerase promoter (pT7), TAC promoter (pTAC), Trp promoter, Lac promoter, Tre promoter, PhoA promoter for example. Suitable promoters for expression in mammalian cells include viral promoters (e.g., CMV, LTR, RSV, SV40, TK, pCAG, etc.), domestic gene promoters (e.g., Elfu, chicken Pactine, Ubiquitine, INSM1, etc.), hybrid promoters (e.g., actine/globin, etc.), etc. A vector may comprise more than one promoter. The promoters may be inducible or regulated. For instance, the use of inducible or regulated promoters allows a better control of production by dissociating the culture from production phases. Inducible or regulated promoters may be found in the literature, such as the Tetracycline system, the Geneswitch system, the Ecdysone system, the Oestradiol system, the RU486 system, the Cumate system, the metallothionein promoter etc. Other systems are based on electric currents or microwaves, such as focalized ultrasound system, AIR induced expression system and the like. These systems can be used to control expression of a polypeptide according to the invention.

The polypeptides may be co-expressed with other factors. The cDNAs coding for each may be both placed downstream of the same promoter, but separated by an IRES sequence, or each of them downstream of its own promoter.

The vector may further comprise an origin of replication and/or a marker gene, which may be selected from conventional sequences. An amplification selection marker such as the DHFR gene can be inserted in the backbone of the vector. The vector may further comprise various combinations of these different elements which may be organized in different ways.

In certain embodiments, DNA delivery may occur by use of liposomes, nanocapsules, microparticles, microspheres, lipid particles, vesicles, optionally mixing with cell penetrating polypeptides, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out.

Cells: The present invention also provides for cells comprising a nucleic acid or a vector as described above.

In a preferred embodiment, a cell comprises any of the polypeptides described herein, any of the nucleic acid molecules described herein, or any of the expression vectors described herein (for example, a stem cell, cell-line, an APC, a T cell or a B cell, in culture or in vivo).

In another embodiment, a cell expressing a chimeric molecule wherein the chimeric molecule comprises at least one *Salmonella* pathogenicity island 1 (SPI-1) and at least one *Salmonella* pathogenicity island 2 (SP1-2) protein, peptides, derivatives, variants or combinations thereof. In embodiments, the cell comprises: an animal cell, a mammalian cell, a bacterial cell, a yeast cell, a tumor cell, a transformed cell, a cell-line or any combinations thereof. The cells expressing the SPI-1 and SPI-2 molecules can be transfected or transformed and administered to the subject. The cells can secrete the encoded SPI-1 and SPI-2 molecules into blood and lymphatic system. Alternatively, the cells can express the SPI-1 and/or SPI-2 molecules on the cell surface such that they are presented to immune cell to stimulate an immune response. Accordingly, the cells encoding for: SPI-1, SPI-2, SPI-1 chimeric molecules, SPI-2 chimeric molecules, or any peptides thereof, can be presented to the immune system for priming the immune system to eliciting an antigen specific response against any *Salmonella* serovars. The administration of the cells can be accompanied with an adjuvant.

The host cell may be selected from any eukaryotic and prokaryotic cells, typically from a mammalian cell (in particular a human, rodent, canine cell), a bacterial cell (in particular *E. coli, Bacillus brevis, Bacillus subtilis*), a yeast cell, a plant cell and an insect cell. These host cells may be adapted to serum-free media. Production may also be accomplished in a transgenic animal or plant.

In some embodiments, recombinant host cells are selected from mammalian cells, in particular human cells as well as derivatives or mutants thereof, including bone marrow cells stem cells, cells of the immune system and the like. Other examples of suitable host cells include Chinese Hamster Ovary (CHO) cells, Baby Hamster Kidney (BHK) cells, Human Embryonic Kidney (HEK-293) cells, human epidermal keratinocytes (HEK), human stromal or epithelial cells, PERC6, etc. In such mammalian cells, polypeptides may be produced as a secreted protein using functional signal peptide sequences.

Vaccination and Immunogenicity

Immune systems are classified into two general systems, the "innate" or "primary" immune system and the "acquired/adaptive" or "secondary" immune system. It is thought that the innate immune system initially keeps the infection under control, allowing time for the adaptive immune system to develop an appropriate response. The various components of the innate immune system trigger and augment the components of the adaptive immune system, including antigen-specific B and T lymphocytes (Kos, *Immunol, Res.* 1998, 17:303; Romagnani, *Immunol, Today,* 1992, 13:379; Banchereau and Steinman, N 1988, 392:245). A "primary immune response" refers to an innate immune response that is not affected by prior contact with the antigen. The main protective mechanisms of primary immunity are the skin (protects against attachment of potential environmental invaders), mucous (traps bacteria and other foreign material), gastric acid (destroys swallowed invaders), antimicrobial substances such as interferon (IFN) (inhibits viral replication) and complement proteins (promotes bacterial destruction), fever (intensifies action of interferons, inhibits microbial growth, and enhances tissue repair), natural killer (NK) cells (destroy microbes and certain tumor cells, and attack certain virus infected cells), and the inflammatory response (mobilizes leukocytes such as macrophages and dendritic cells to phagocytose invaders).

Some cells of the innate immune system, including macrophages and dendritic cells (DC), function as part of the adaptive immune system as well by taking up foreign antigens through pattern recognition receptors, combining peptide fragments of these antigens with major histocompatibility complex (MHC) class I and class II molecules, and stimulating naive $CD8^+$ and $CD4^+$ T cells respectively (Banchereau and Steinman, supra; Holmskov et al., *Immunol. Today,* 1994, 15:67; Ulevitch and Tobias Annu. *Rev. Inununol,* 1995, 13:437): Professional antigen-presenting cells (APCs) communicate with these T cells, leading to the differentiation of naive $CD4^+$ T cells into T-helper 1 (Th1) or T-helper 2 (Th2) lymphocytes that mediate cellular and humoral immunity, respectively (Trinchieri *Annu, Rev. Immunol.* 1995, 13:251; Howard and O'Garra, *Immunol, Today,* 1992, 13:198; Abbas et al., *Nature.* 1996, 383:787; Okamura et al., *Adv. Immunol.* 1998, 70:281; Mosmann and Sad, *Immunol. Today.* 1996, 17:138; O'Garra Immunity. 1998, 8:275).

In adaptive immunity, adaptive T and B cell immune responses work together with innate immune responses. The basis of the adaptive immune response is that of clonal recognition and response. An antigen selects the clones of cell which recognize it, and the first element of a specific immune response must be rapid proliferation of the specific lymphocytes. This is followed by further differentiation of the responding cells as the effector phase of the immune response develops. These effector T lymphocytes, in the context of the embodiments, are the tumor specific T lymphocytes.

Delivery of an immunogen to appropriate cells can be effected ex vivo, in situ, or in vivo by use of any suitable approach known in the art. For example, for in vivo therapy, a nucleic acid encoding the SPI-1 and/or SPI-2 chimeric molecules, either alone or in conjunction with a vector, liposome, or precipitate may be injected directly into the subject, and in some embodiments, may be injected at the site where the expression of the molecules is desired. In other embodiments, cells comprising the nucleic acids encoding the SPI-1 and/or SPI-2 chimeric molecules are administered to a subject in need thereof, wherein the cells producing the immunogenic SPI-1 and/or SPI-2 peptides elicit an immune response to the immunogens. For ex vivo treatment, the subject's cells are removed, the nucleic acid is introduced into these cells, and the modified cells are returned to the subject either directly or, for example, encapsulated within porous membranes which are implanted into the patient. See, e.g. U.S. Pat. Nos. 4,892,538 and 5,283,187.

There are a variety of techniques available for introducing nucleic acids into viable cells. The techniques vary depending upon whether the nucleic acid is transferred into cultured cells in vitro or in vivo in the cells of the intended host. Techniques suitable for the transfer of nucleic acid into mammalian cells in vitro include the use of liposomes, electroporation, microinjection, cell fusion, chemical treatments, DEAB-dextran, and calcium phosphate precipitation. Other in vivo nucleic acid transfer techniques include transfection with viral vectors (such as adenovirus, Herpes simplex I virus, adeno-associated virus or retrovirus) and lipid-based systems. The nucleic acid and transfection agent are optionally associated with a microparticle. Exemplary transfection agents include calcium phosphate or calcium chloride co-precipitation, DBAE-dextran-mediated transfection, quaternary ammonium amphiphile DOTMA ((diolcoyloxypropyl)trimethylammonium bromide, commercialized as LIPOFECTIN by GIBCO-BRL)) (Felgner et al. (1987) *Proc. Natl. Acad. Sci. USA* 84, 7413-7417; Malone et al. (1989) *Proc. Natl. Acad. Sci. USA* 86 6077-6081); lipophilic glutamate diesters with pendent trimethylammonium heads (Ito et al. (1990) *Biochem, Biophys. Acta* 1023, 124-132); the metabolizable parent lipids such as the cationic lipid dioctadecylamido glycylspermine (DOGS, Transfectam, Promega) and dipalmitoylphosphatidyl ethanolamylspermine (DPPES) (J. P. Behr (1986) *Tetrahedron Lett:* 27, 5861-5864; J. P. Behr et al. (1989) *Proc. Natl. Acad. Sci. USA* 86, 6982-6986); metabolizable quaternary ammonium salts (DOTB, N-(1-[2,3-dioleoyloxy] propyl)-N,N,N-trimethylammonium methylsulfate (DOTAP) (Boehringer Mannheim), polyethyleneimine (PEI), dioleoyl esters, ChoTB, ChoSC, DOSC) (Leventis et al. (1990) Biochim. Inter: 22, 235-241); 3β[N-(N'N' dimethylaminoethane)-carbamoyl]cholesterol (DC-Chol), dioleoylphosphatidyl ethanolamine (DOPE)/3β[N-(N',N'-dimethylaminoethane)-carbamoyl]cholesterolDC-Chol in one to one mixtures (Gao et al., (1991) *Biochim. Biophys. Acta* 1065, 8-14), spermine, spermidine, lipopolyamines (Behr et al., *Bioconjugate Chem*, 1994, 5:382-389), lipophilic polylysines (LPLL) (Zhou et al., (1991) *Biochim. Biophys. Acta* 939, 8-18), [[(1,1,3,3-tetramethylbutyl) cre-soxy]ethoxy]ethyl]dimethylbenzylammonium hydroxide (DEBDA hydroxide) with excess phosphatidylcholine/cholesterol (Ballas et al., (1988) *Biochim. Biophys. Acta* 939, 8-18), cetyltrimethylammonium bromide (CTAB)/DOPE mixtures (Pinnaduwage et al. (1989) *Biochim. Biophys, Acta* 985, 33-37), lipophilic diester of glutamic acid (TMAG) with DOPE, CTAB, DEBDA, didodecylammonium bromide (DDAB), and stearylamine in admixture with phosphatidylethanolamine (Rose et al., (1991) *Biotechniques* 10, 520-525), DDAB/DOPE (TransfectACE, GIBCO BRL), and oligogalactose bearing lipids. Exemplary transfection enhancer agents that increase the efficiency of transfer include, for example, DEAE-dextran, polybrene, lysosome-disruptive peptide (Ohmori N I et al, *Biochem Biophys Res Comniun* Jun. 27, 1997; 23 5 (3): 726-9), chondroitan-based proteoglycans, sulfated proteoglycans, polyethylenimine, polylysine (Pollard H et al. *J Biol Chem,* 1998 273 (13): 7507-11), integrin-binding peptide CYGGRGDTP (SEQ ID NO: 25), linear dextran nonasaccharide, glycerol, cholesteryl groups tethered at the 3" terminal internucleoside link of an oligonucleotide (Letsinger, R. L. 1989 *Proc Natl Acad Sci USA* 86: (17): 6553-6), lysophosphatide, lysophosphatidylcholine, lysophosphatidylethanolamine, and I-oleoyl lysophosphatidylcholine.

Embodiments of the invention include methods of inducing an immune response in a subject comprising delivering an antigen to a subject in need thereof. In certain embodiments, the method comprises providing an antigen presenting cell (APC) and contacting (stimulating) them in vitro, vivo or in vivo with an SPI-1 and/or SPI-2 antigen either by incubation with the SPI-1 and/or SPI-2 peptides or with the cells expressing or secreting the SPI-1 and/or SPI-2 antigens. In certain embodiments, the antigen is delivered to the APC in the body of the subject. In certain embodiments, administration of a cell expressing one or more SPI-1 and/or SPI-2 molecules to the subject results in delivery of the antigen into an APC and T cell activation in the subject.

In another embodiment, an APC of the subject is isolated from the subject, the antigen is delivered to the APC outside of the body of the subject, and the APC comprising the delivered antigen is later administered to the subject.

In an embodiment, a method of enhancing the immune response in a mammal comprises the steps of contacting one or more lymphocytes with the antigenic compositions, wherein the antigen is presented by an immune cell, such as an APC. The enhanced immune response may be an active or a passive immune response. The response may be part of an adoptive immunotherapy approach in which APCs, such as dendritic cells, B cells or monocytes/macrophages, are obtained from a subject (e.g., a patient), then pulsed with a composition comprising the antigenic composition, and then administering the APC to a subject in need thereof. In certain embodiments, the method of the invention comprises ex vivo immunization and/or in vivo therapy in a subject. In one embodiment, the subject is a mammal. Preferably, the mammal is a human. Ex vivo procedures are well known in the art. Briefly, cells are isolated from a subject (preferably a human) and contacted with the antigenic compositions to produce an antigen-loaded APC. The antigen-loaded APC can be administered to a recipient to provide a therapeutic benefit. The recipient may be a human and the antigen-loaded APC can be autologous with respect to the recipient. Alternatively, the APC can be allogeneic, syngeneic or xenogeneic with respect to the recipient.

In addition to using a cell-based vaccine in terms of ex vivo immunization, the present invention also provides compositions and methods for in vivo immunization to elicit an immune response directed against an antigen in a patient.

The preparation of compositions for use as vaccines is known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared (e.g. lyophilized, freeze-dried forms, etc.). The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of protein, polypeptide or peptide (or encoding nucleic acids) in the formulations may vary. However, in general, the amount of vaccinating/immunizing agent in the formulations will be from about 1 to about 99%.

In some embodiments, the immunogenic compositions embodied herein are administered with an immune modulating effector molecules or adjuvants. In one embodiment, an immune modulating effector molecule is administered in conjunction with or at alternative times the antigenic compositions or cells comprising the antigenic compositions. An immune-modulating effector molecule positively and/or negatively influences the humoral and/or cellular immune system, particularly its cellular and/or non-cellular components, its functions, and/or its interactions with other physiological systems. The immune-modulating effector molecule comprises cytokines, chemokines, macrophage migration inhibitory factor (MIF; as described, inter alia, in Bernhagen (1998). *Mol Med* 76 (3-4); 151-61 or Metz (1997), *Adv Immunol* 66, 197-223), T-cell receptors and soluble MHC molecules. Such immune-modulating effector molecules are well known in the art and are described, inter alia, in Paul, "Fundamental immunology", Raven Press, New York (1989). In particular, known cytokines and chemokines are described in Meager, "*The Molecular Biology of Cytokines*" (1998), John Wiley & Sons, Ltd., Chichester, West Sussex, England; (Bacon (1998). Cytokine Growth Factor Rev 9 (2): 167-73; Oppenheim (1997). *Clin Cancer Res* 12, 2682-6; Taub, (1994) *Ther. Immunol.* 1 (4), 229-46 or Michiel, (1992). *Semin Cancer Biol* 3 (1), 3-15).

Immune cell activity that may be measured include, but is not limited to, (1) cell proliferation by measuring the DNA replication; (2) enhanced cytokine production, including specific measurements for cytokines, such as IFN-γ, GM-CSF, or TNF-α; (3) cell mediated target killing or lysis; (4) cell differentiation; (5) immunoglobulin production; (6) phenotypic changes: (7) production of chemotactic factors or chemotaxis, meaning the ability to respond to a chemotactin with chemotaxis; (8) immunosuppression, by inhibition of the activity of some other immune cell type; and, (9) apoptosis, which refers to fragmentation of activated immune cells under certain circumstances, as an indication of abnormal activation.

In addition, the composition may contain adjuvants, many of which are known in the art. For example, adjuvants suitable for use in the invention include but are not limited to: bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof. Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A. Other non-toxic I.PS derivatives include monophosphoryl lipid A mimics, such as aminoalkyl glucosaminide phosphate derivatives e.g. RC-529. Lipid A derivatives include derivatives of lipid A from *Escherichia coli* such as OM-174. Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromie or poly(da) sequences have also been shown to be immunostimulatory. The CpG's can include nucleotide modifications/analogs such as phosphorothioate modifications and can be double-stranded or single-stranded. e.g. replacement of guanosine with 2'-deoxy-7-deazaguanosine. The CpG sequence may include, for example, the motif GTCGTT or TTCGTT. The CpG sequence may be specific for inducing a Th1 immune response, such as a CpG-A ODN, or it may be more specific for inducing a B cell response, such a CpG-B ODN. CpG-A and CpG-B ODNs. Preferably, the CpG is a CpG-A ODN. Preferably, the CpG oligonucleotide is constructed so that the 5' end is accessible for receptor recognition. Optionally, two CpG oligonucleotide sequences may be attached at their 3' ends to form "immunomers".

Bacterial ADP-ribosylating toxins and detoxified derivatives thereof may be used as adjuvants in the invention. Preferably, the protein is derived from *E. coli* (e.g. *E. coli* heat labile enterotoxin "LT"), cholera ("CT"), or pertussis ("PT"). The use of detoxified ADP-ribosylating toxins as mucosal adjuvants and as parenteral adjuvants is known. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, is known. Such adjuvants are described, for example, in issued U.S. Pat. No. 8,039,007 (the complete contents of which is hereby incorporated by reference in entirety). Various interleukins may also be used as adjuvants to increase the immune response in a subject. In preferred embodiments, the adjuvant is a mucosal adjuvant such as, for example, the double mutant heat-labile toxin (dmL.T) from enterotoxigenic *E. coli*.

Administration and Formulations

The vaccine compositions (preparations) and immunogenic compositions (e.g. peptides, polypeptides, oligonucleotides, polynucleotides, etc.) of the present invention may be administered by any of the many suitable means which are well known to those of skill in the art, including but not limited to by injection, inhalation, orally, intranasally, topically, inclusion in a food product, etc. In some embodiments, the mode of administration is intradermal or intramuscular. In addition, the compositions may be administered in conjunction with or in a composition which contains other antigens of interest. In other words, they may be administered as a component of a multivalent vaccine which also contains antigens against other related or non-related infectious diseases, e.g. childhood diseases, such as polio, whooping cough, tetanus, diphtheria, etc.

Recipients of the vaccine of the invention are generally mammals, frequently humans, but this is not always the While some aspects, the vaccine is used to prevent illness in humans, in other aspects, the vaccine is used to prevent illness and/or to block the carrier states in agriculturally important animals, i.e. veterinary applications are also contemplated. Animals which could benefit from receiving the vaccine/immune eliciting compositions of the invention include but are not limited to: cattle, poultry, swine, horses, sheep and goats. The vaccine is generally delivered intranasally or subcutaneously or intramuscularly, and may be delivered in combination with other agents such as other vaccinogens.

For humans, the vaccines may be administered alone or together with so-called "child hood" vaccines. Thus, the recipients are preferably human children who may be infants (e.g, up to about 1 hear of age), toddlers (e.g. up to about 2 years of age), or older, and administration may be carried out as a series of initial inoculations followed by booster doses at suitable intervals, e.g. monthly, or every 6-months, or yearly, etc. as necessary to provide protection. Thereafter, or in the case of adults who have not previously been vaccinated, the vaccines may be administered as necessary to result in a protective immune response, and subjects may be re-boosted e.g. about every 10 years throughout adult life. Of special interest is vaccination of individuals with compromised immune systems, e.g. the elderly, those receiving cancer or other immune weakening therapy, those afflicted with HIV, etc.

Vaccine recipients may have never been exposed to Salmonella, or may have been exposed or suspected of having been exposed but be asymptomatic, or may have actual symptoms of disease, and still benefit from administration of the vaccine. Vaccine administration may prevent disease symptoms entirely, or may lessen or decrease disease symptoms, the latter outcome being less than ideal but still better than experiencing full-blown disease symptoms.

In a preferred embodiment, the amount of protein that is administered per dose of vaccine is in the range of from about 0.0001 to about 1000 µg/kg. In one embodiment, the amount is in the range of from about 0.001 to about 1000 µg/kg of body weight of the recipient. In one embodiment, the amount is in the range of from about 0.01 to about 1000 µg/kg of body weight of the recipient. In one embodiment, the amount is in the range of from about 0.01 to about 100 µg/kg of body weight of the recipient. Those of skill in the art will recognize that the precise dosage may vary from situation to situation and from patient to patient, depending on e.g. age, gender, overall health, various genetic factors, and other variables known to those of skill in the art. Dosages are typically determined e.g. in the course of animal and/or human clinical trials as conducted by skilled medical personnel, e.g. physicians.

The vaccines and immunogenic compositions of the invention are broad-based vaccines and may be used to provide immune protection against a variety of Salmonella species, including both typhoidal and non-typhoidal species, and all S. enterica subspecies. Examples of these two categories of Salmonella include but are not limited to: for typhoidal Salmonella; Paratyphi A&B; and for non-typhoidal Salmonella: Typhimurium, Enteriditis, Newport, Dublin, Administration of the compositions of the invention results in the production of an immune response, which may be a protective immune response, in subjects who receive the compositions, e.g. by elicitation of antibody production against the administered antigens. Such antibodies are also encompassed by the invention, for example, those generated using laboratory techniques in experimental animals, or using cell culture, or by chemical syntheses, etc. Such antibodies may be polyclonal or monoclonal, and may be specific for the antigens (reacting with no other antigens) or selective for the antigens (reacting more strongly or preferably with the antigens, compared to other antigens). The antibodies may be multivalent. The antibodies may be used for research and/or diagnostic purposes, or alternatively, for treatment, especially of individuals who are infected with Salmonella.

The invention provides methods of vaccinating, or, alternatively, of eliciting an immune response, in a subject in need thereof. The method generally involves identifying a suitable subject, and administering the composition as described herein. The method may also encompass follow-up of administration, e.g. by assessing the production of protective antibodies by the subject, or the presence (or lack thereof) of disease symptoms, etc. The immune response that is elicited may be of any type, i.e. any type of antibody may be produced in response to administration, and cell-mediated immunity may also be elicited.

In addition, the invention provides methods of treating or preventing Salmonella infection by one or both of a typhoid Salmonella serovar and a non-typhoid Salmonella serovar in a subject, methods of lessening the severity of symptoms of Salmonella infection in a subject, and methods of decreasing fecal shedding of Salmonella from a subject who is or is likely to be infected with Salmonella. Each of these methods involves administering to the subject an amount of a composition comprising at least one Salmonella pathogenicity island 1 (SPI-1) and/or Salmonella pathogenicity island 2 (SPI-2) extracellular protein; and a physiologically acceptable carrier. The amount of the composition is administered is sufficient to elicit an immune response to the at least one Salmonella serovar in said subject, thereby of treating or preventing Salmonella infection, lessening the severity of symptoms of Salmonella infection, and/or decreasing fecal shedding of Salmonella.

In some embodiments, the compositions embodied herein, may be administered as a regimen in conjunction with other therapeutics, such, antibiotics, anti-inflammatory agents, The invention has been described in detail with reference to preferred embodiments thereof. However, it will be appreciated that those skilled in the art, upon consideration of this disclosure, may make modifications and improvements within the spirit and scope of the invention.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

In the case of Salmonella, an effective vaccine could be used to prevent illness in humans and to block the carrier activity in agriculturally important animals. Although some progress has been made in recent years, available vaccines against Salmonella spp. are not broadly protective and are almost entirely directed at the typhoid causing serovars, even though the non-typhoid serovars are a major public health problem.

Because the SPI-1 and SPI-2 proteins are surface localized prior to the invasion of host cells, they serve as prime targets for subunit vaccines. These four tip proteins are the initial tip protein SipD and the first 'translocator' protein SipB from SPI-1, and SseB and SseC from SPI-2, which are expressed and are surface exposed after entry of the bacterium into the cell. We previously demonstrated that the SipD and SipB homologs in Shigella, IpaD and IpaB, respectively, are protective antigens against challenge with serotypically distinct S. flexneri and S. sonnei strains using the mouse pulmonary model (see U.S. patent application No. 20130149329, the complete contents of which is hereby incorporated by reference in entirety). A similar Salmonella serotype-independent subunit vaccine would be of tremendous public health value. Thus, we have determined the protective efficacy of SipD, SipB and SseB administered with adjuvants against challenge by *Salmonella* spp.

For Examples 1-3 below, recombinant SipD and SseB were prepared by expression in *E. coli* using His-tag technology and pET vectors (commercially available from Novagen), and purification was carried out via column chromatography. Within the cytoplasm of *Salmonella*, SipB forms a complex with its cognant chaperone SicA, and recombinant SipB was prepared with its chaperone by co-expression of His-tagged recombinants in *E. coli* and co-purification via column chromatography in a method similar to that of Birket et al. (Biochemistry 46:8128-8137). SipB was also produced alone by inducing its release from the chaperone using different detergents.

SipB, SipD, and SseB were then examined as protective antigens by immunizing mice (Examples 1 and 2) and calves (Example 3) intranasally or subcutaneous, followed by challenge, as described below. The results showed that SseB, SipB and SipD are effective in reducing the severity and length of disease caused by *Salmonella*. These findings impart a significant advancement over the live-attenuated and lipopolysaccharide-based vaccines that are currently being tested, because they provide serotype-independent protection and they can be given to children.

Example 1

Figure 1:
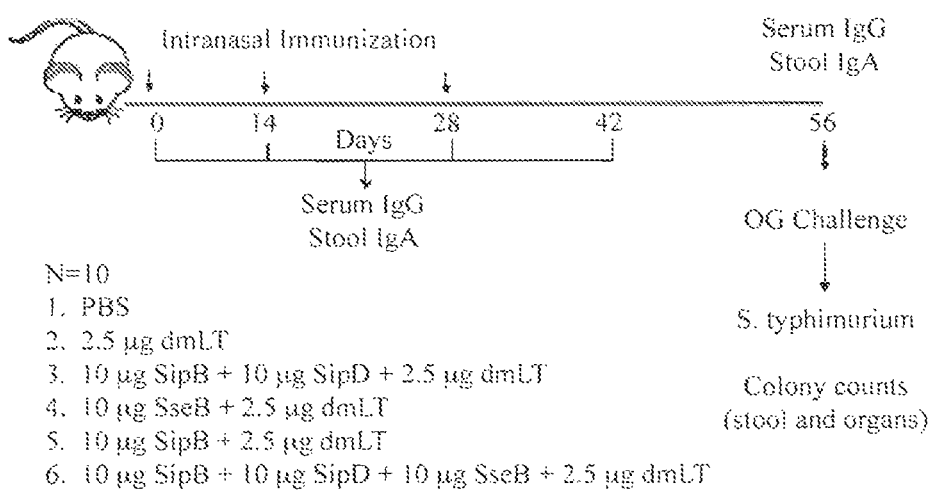
FIG. 1. Schematic illustration of the mouse testing protocol for Example 1.
Figure 2:
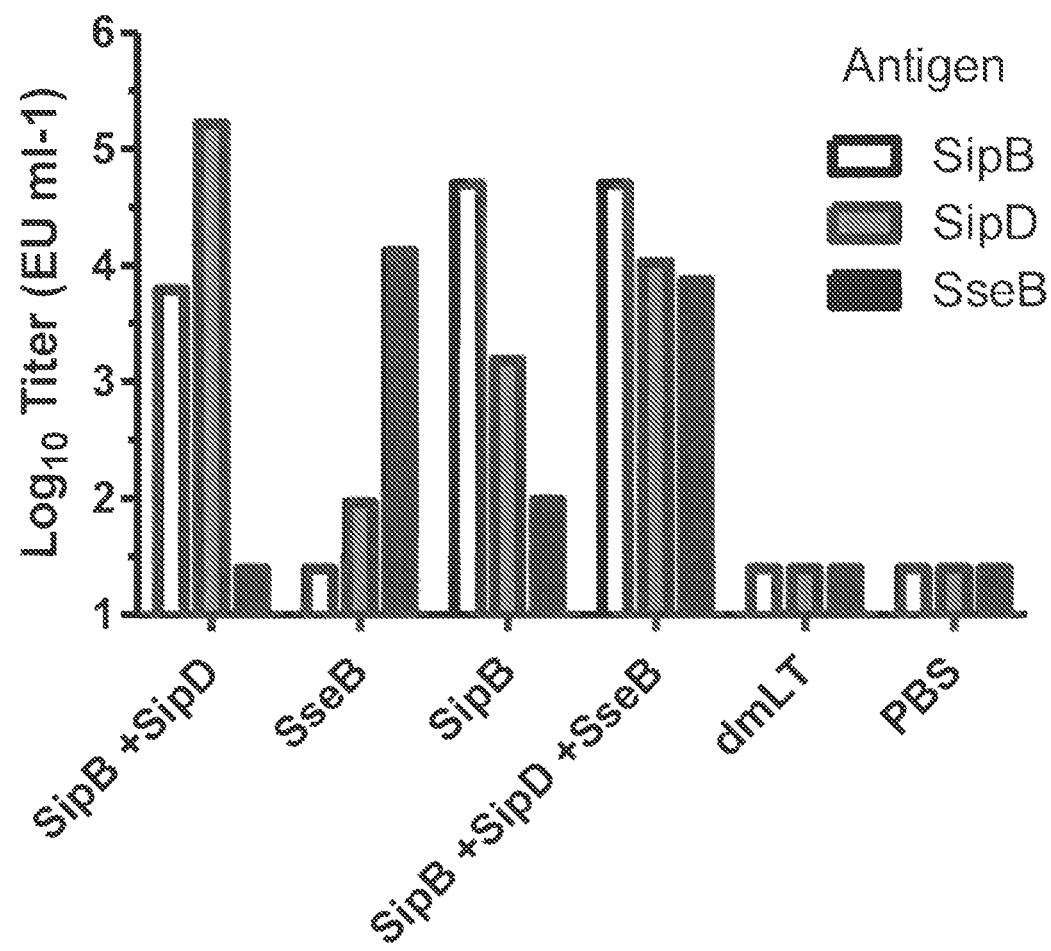
FIG. 2. IgG antibody titers from mice immunized with T3SS proteins at day 28. Each bar represents data from pooled samples (N=10).
Figure 3:
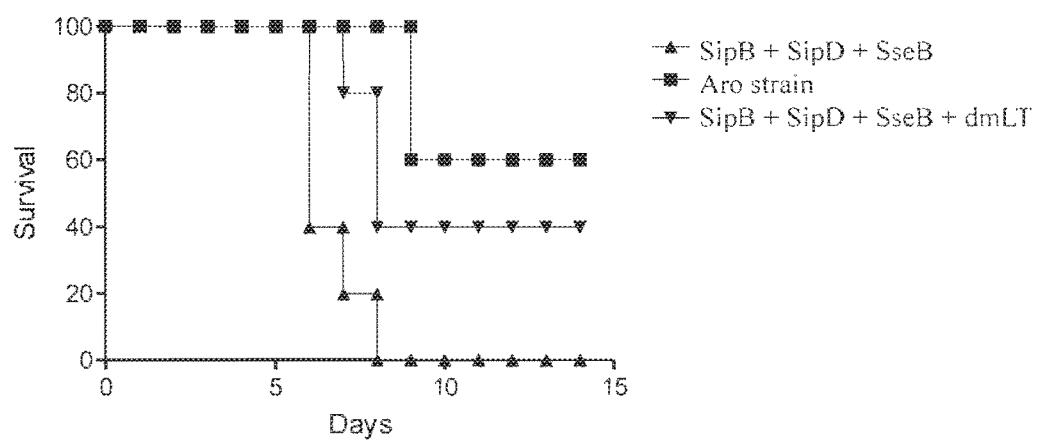
FIG. 3. Survival after challenge. Balb-c mice (N=5 per group) were vaccinated twice with attenuated *Salmonella* vaccine strain Aro, or 3 times with of a composition comprising SipB, SipD and SseB protein (10 μg of each) with or without adjuvant dmLT. Mice were challenged vias orogastric challenge with $1 \times 10^6$ CFU of *Salmonella* strain SL1344. Survival was monitored for 14 days after challenge.

FIG. 1 provides a Schematic illustration of a first mouse testing protocol for Example 1. Briefly, Balb-c mice (N=5 per group) were immunized intranasally 2 times with Aro strain or 3 times (days 0, 14 and 28) with 10 μg each of SipB/SipD/SseB protein with or without dmLT. Serum IgG and stool IgA were monitored throughout. Serum IgG antibody titers at day 28 are shown in FIG. 2. Mice were orogastrically challenged with 10" colony forming units (CFUs) of *Salmonella enterica* serovar *Typhimurium* SL1344 after streptomycin treatment on day 56 and survival after challenge was monitored for 14 days after challenge. The results are shown in FIG. 3.

As can be seen, the proteins provide protection against a *S. typhimurium* challenge at a level approaching the live attenuated vaccine (Aro strain).

Example 2

Figure 4:
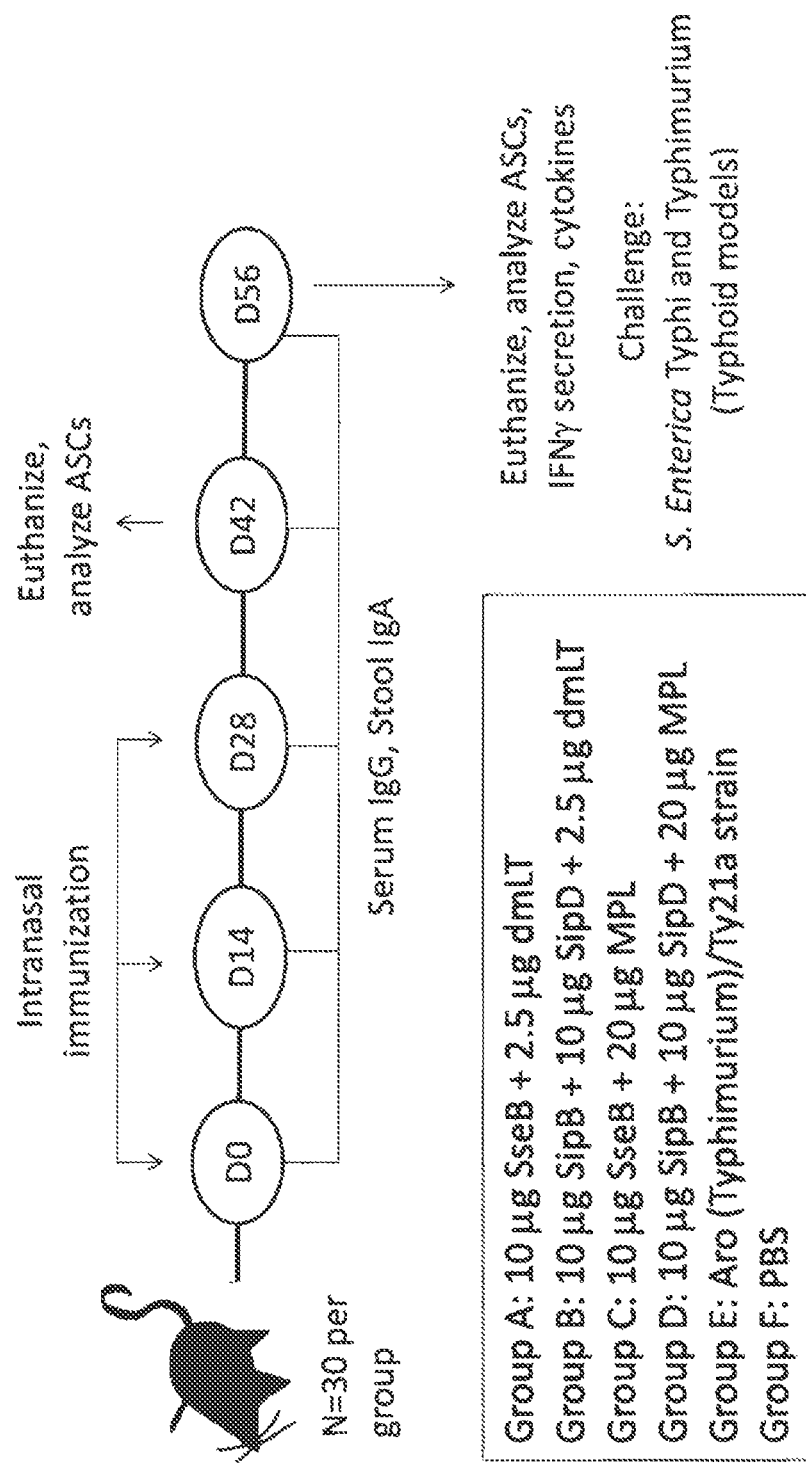
FIG. 4 contains a schematic illustration of the mouse testing protocol for Example 2.
Figure 5:
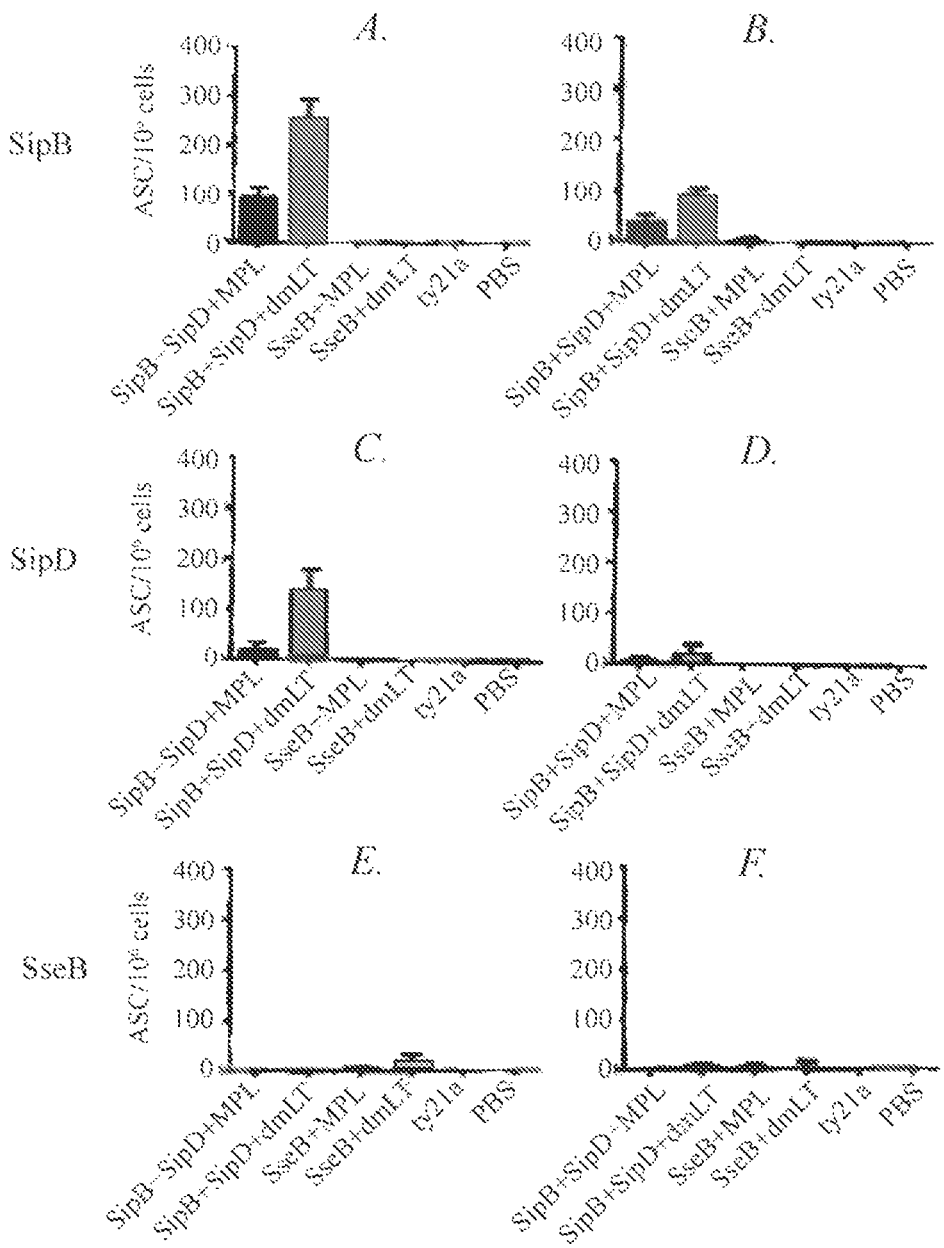
FIGS. 5A-5F. FIGS. A and B: number of SipB specific ASCs in spleens of immunized mice at days 42 and 56, respectively.

FIG. 4 provides a Schematic illustration of a mouse testing protocol for Example 2. Briefly, Balb-c mice, n=30) were immunized on Days 0, 14 and 28 as follows: Group A: 10 μg SseB+2.5 μg of dmLT (double mutant *E. coli* heat labile toxin) as adjuvant; Group B: 10 μg SipB+10 μg SipD+2.5 μg dmLT; Group C: 10 μg SseB+20 μg MPL (monophosphooryl Lipid A); Group D: 10 μg SipB+10 μg SipD+20 μg MPL; Group E: Aro (Aro attenuated *S. enterica* var. *Typhimurium* vaccine strain, "*Typhimurium*/Ty21 a strain"); Group F: phosphate buffered saline (PBS, i.e. vehicle). At day 42 post immunization, some mice were euthanized and their spleens were analyzed for antibody secreting cells (ASCs). On day 56, additional mice were euthanized and analyzed for ASCs, IFNγ secretion, and cytokine production and the remaining mice were challenged with *S. enterica typhi* or *typhimurium* (typhoid models).

Figure 6:
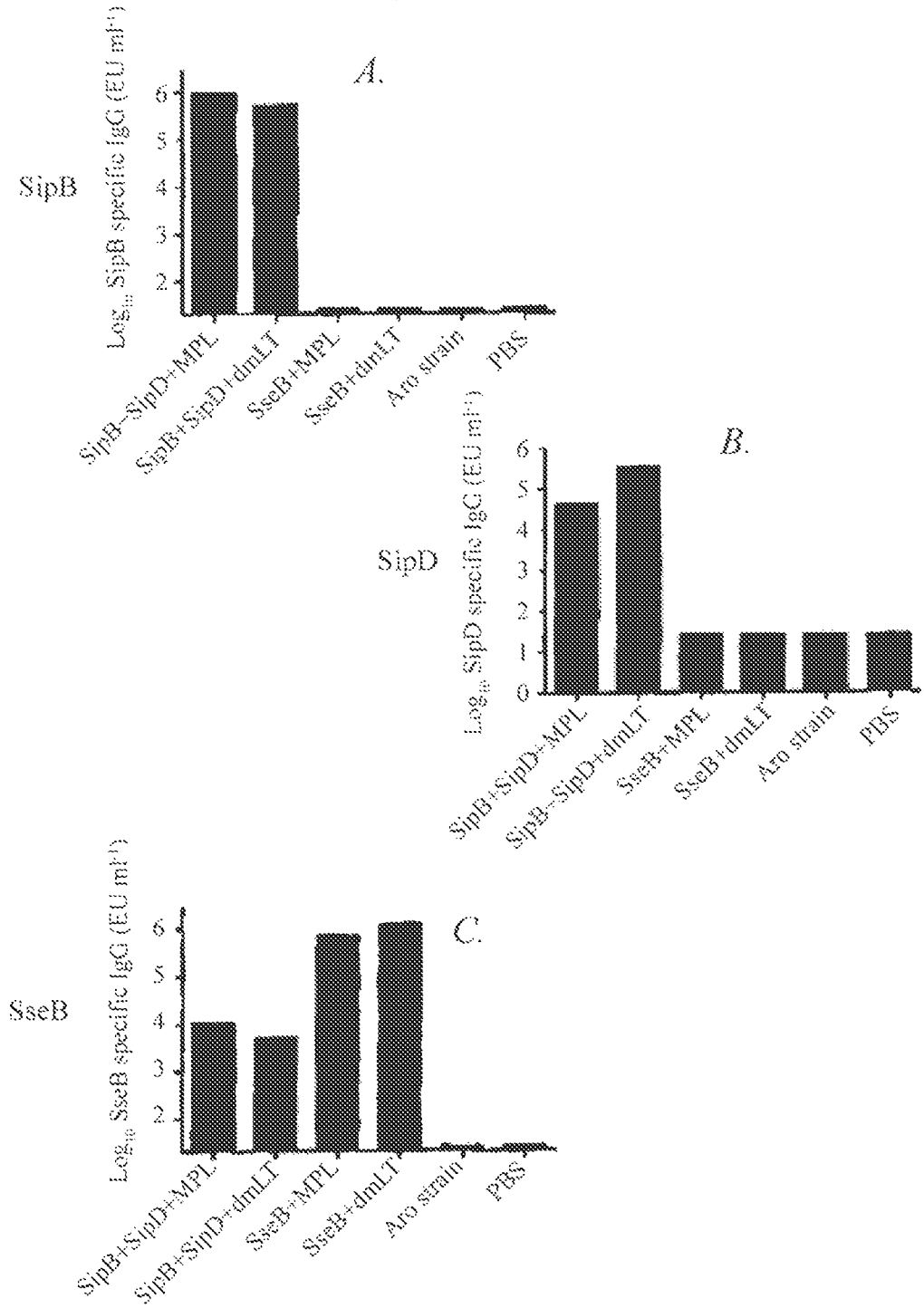
FIGS. 6A-6C. IgG titers in immunized mice at day 56.
Figure 7:
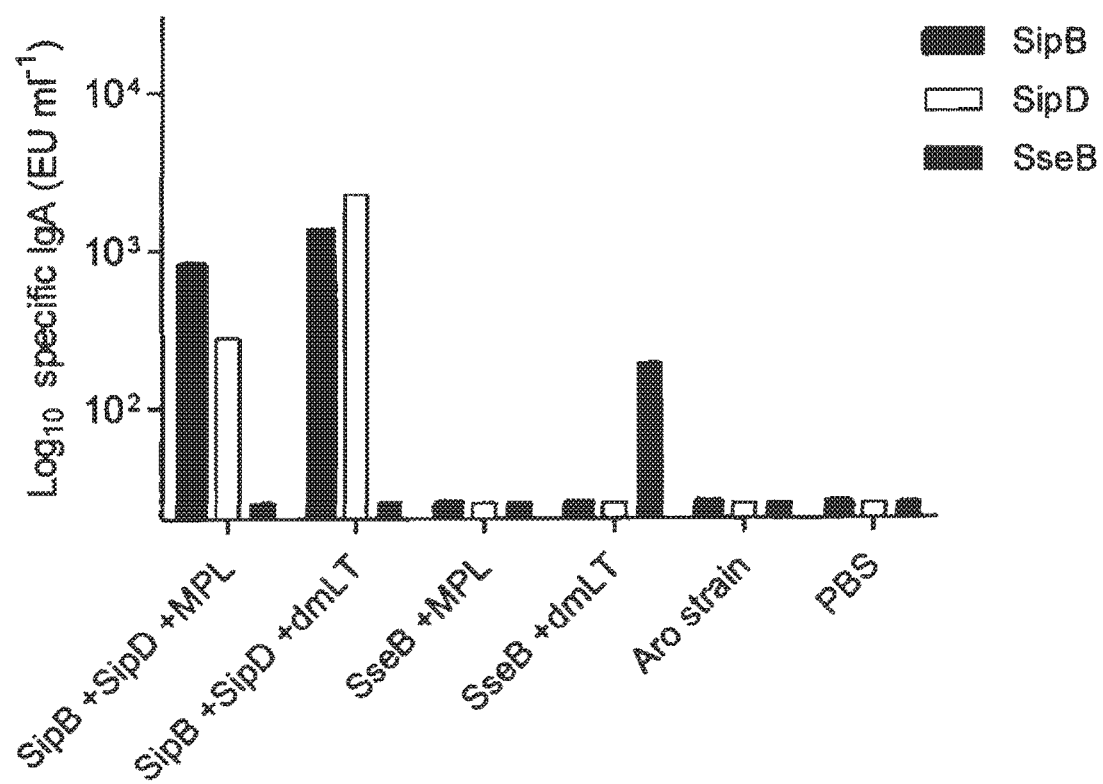
FIG. 7. Stool IgA titers in immunized mice at day 56.
Figure 8:
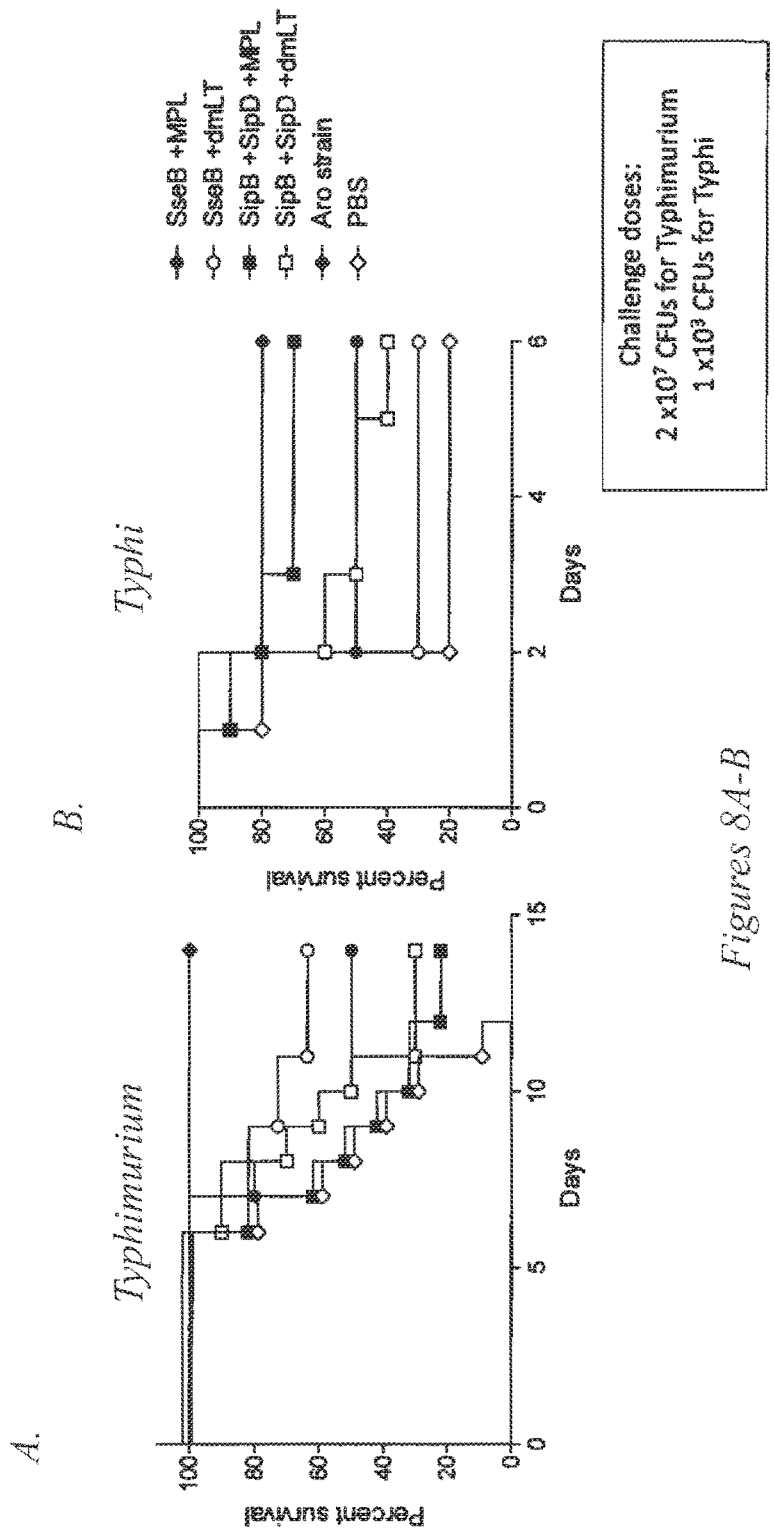
FIGS. 8A and 8B. Protection efficacy in immunized mice after challenge (at day 56) with (FIG. 8A) *S. enterica Typhi* or (FIG. 8B) *S. enterica Typhimurium*.

Immunogenicity as shown by spleen ASC results is shown in FIG. 5A-F. FIG. 6A-C shows IgG titers in immunized mice at day 56, FIG. 7 shows stool IgA titers in immunized mice at day 56, and FIG. 8A and FIG. 8B show protection efficacy in immunized mice after challenge (at day 56) with *S. enterica typhi* (FIG. 8A) or *S. enterica typhimurium* (FIG. 8B).

As can be seen, the results indicated that SipB, SipD and SseB are immunogenic in mice in that both serum and stool antibodies were detected after immunization, as were spleen ASCs specific for SipB and SipD. Interestingly, the challenge experiments showed different outcomes, with the combination of SipB/SipD being protective in *Typhi* intraperitoneal (IP) mucin challenge model and SseB being protective in the *Typhimurium* orogastric (OG) challenge model.

Example 3: First Calf Testing

Figure 9:
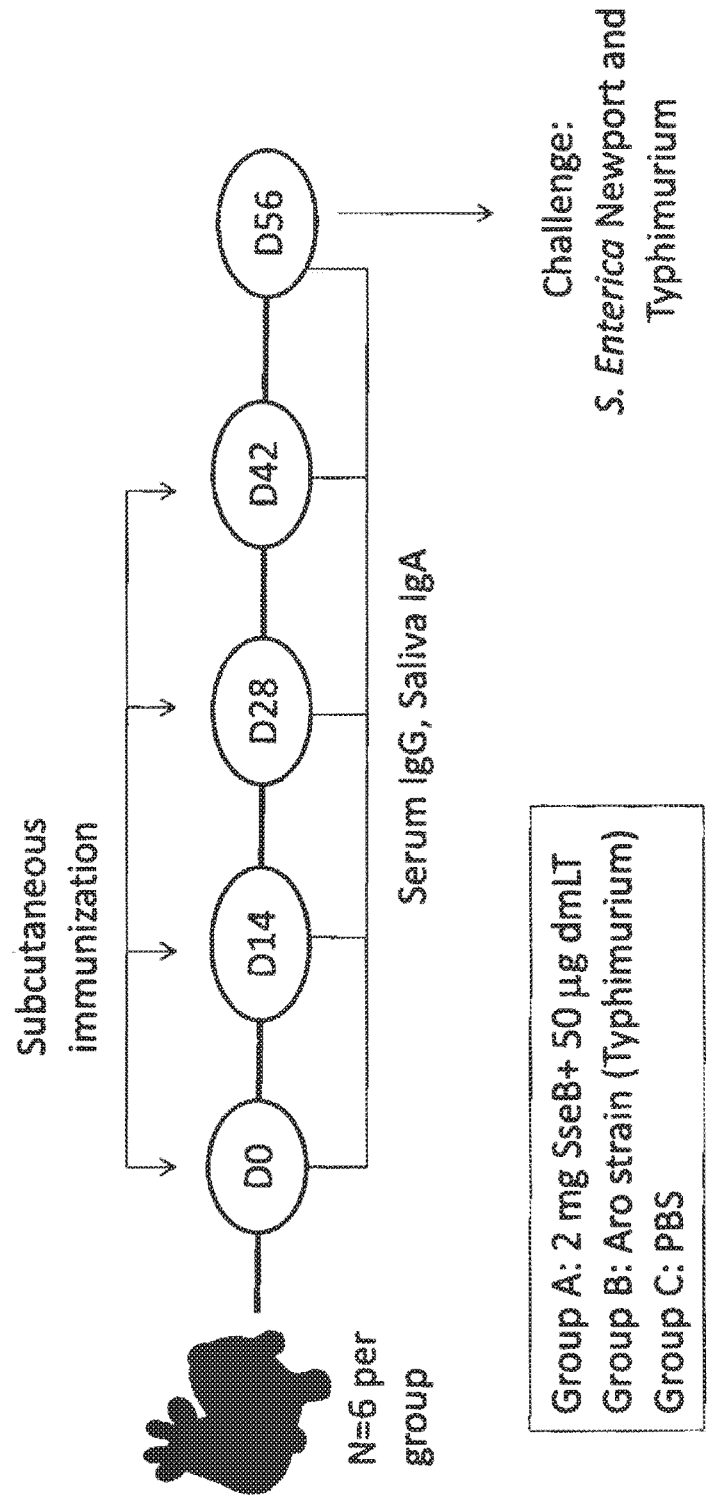
FIG. 9. Schematic illustration of the calf testing protocol for Example 3.

A schematic representation of the experimental protocol is provided in FIG. 9. Calves (21 day old male Holstein or Holstein-Jersey) were immunized subcutaneously at days 0, 14, 28 and 42 as follows: Group A, 2 mg SseB+50 μg of dmLT; Group B, Aro strain (*Typhimurium*); and Group C, PBS (control). Serum IgG (FIG. 10A) and saliva IgA (FIG. 10B) was measured. Calves were challenged with *S. enterica* Newport ($9 \times 10^3$ CFUs) or *Typhimurium* ($1.1 \times 10^3$ CFUs) on day 56. The amount of bacterial shedding in the two groups of challenged animals is shown in FIGS. 11A and B. As can be seen, the total bacterial shedding over the course of ten days for the group vaccinated with SseB+dmIT was not only lower, but the variation over the course of ten days was less than one log unit which is consistent with no effective increase in shedding over time. This is in contrast to the group vaccinated with PBS which had a higher average shedding and an average over the course of the study that spanned over 2.5 log units. Thus, the SseB+dmL.T vaccine reduced disease severity relative to the control group and reduces shedding from the initial time point.

Example 4: Preparation of a Chimeric (Fusion) Protein

A SipD-SipB chimeric protein been developed that allows the protective potential of SipD and SipB to be encompassed in single recombinant protein. This reduces the vaccine composition components to two proteins, the chimeric SipD-SipB and the SipA protein.

The sipD and sipB genes have been genetically fused in a single plasmid and co-transformed into *E. coli* TUNER (DE3) cells with a plasmid encoding sicA, using the following protocol: combine 1 μg of each plasmid with 30 μl chemically competent cells, heat shock, add one ml LB media, incubate at 37° C., for 1 hr and then plated on LB agar containing 100 μg/ml ampicillin and 30 μg Chloramphenicol. sipD was copied by PCR using primers with NdeI at 5' end and SalI at 3' end. sipB was copied by PCR using primers with SalI at 5' end and XhoI at 3' end. The PCR fragments were digested with the restriction enzymes and ligated together and then into NdeI/XhoI digested pET15b from Novagen. The ligation product was used to transform NovaBlue *E. coli*. Transformants were screened for the proper insert and subjected to double stranded sequencing. The gene encoding SicA was copied by PCR from *S. typhimurium* SL1344 (accession number J04117). The PCR fragment was digested with the restriction enzymes NdeI and XhoI and ligated into NdeI/XhoI digested pACYC-Duet-1 from Novagen. The ligation product was used to transform NovaBlue *E. coli*. Transformants were screened for the proper insert and subjected to double stranded sequencing. A plasmid containing the correct sequence for the fusion and a plasmid containing the correct sequence for SicA were transformed into TUNER (DE3) *E. coli* (Novagen). This strain was used to inoculate LB media containing ampicillin and chloramphenicol. The bacteria were grown to an absorbance at 600 of about 0.6 at which time they were induced to over express IpaB/IpgC with Isopropyl-β-D-thiogalactoside (IPTG). The bacteria were grown an additional three hours to allow protein expression to occur. Alternatively, a starter culture of 100 ml was used to inoculate a 5- or 10-liter fermentor vessel containing TB media. After growing overnight (16 hours), the bacteria were induced and allowed to express protein for three hours. The bacteria were collected by centrifugation, resuspended in binding buffer (see below for recipe), and lysed by microfluidization. This suspension was clarified by centrifugation and was loaded onto a nickel charged immobilized metal affinity column (IMAC). The column (5 ml) was washed with 10 bed volumes each of binding and wash buffers and then subjected to a gradient of 0% to 40% elution buffer. Peak fractions were collected, the buffer exchanged into IM ammonium sulfate in 50 mM sodium phosphate pH 7.0 and loaded onto a Butyl Sepharose High Performance column (5 ml) with a linear gradient from IM ammonium sulfate in 50 mM sodium phosphate pH 7.0 to 50 mM sodium phosphate. For preparation of His-tag fusion, the IMAC-bound protein complex was incubated overnight in the presence of 1% OPOE. The chaperone was removed in the flow through and subsequent wash steps. His-tag fusion was eluted in the presence of OPOE to maintain the protein in a soluble form. All proteins were concentrated by ultrafiltration and dialyzed into PBS pH 7.2. Protein concentrations were determined via absorbance at 280 nm using extinction coefficients based on the amino acid composition of each protein.

Buffers that were utilized are listed below:

TABLE 1

| 4× Charge Buffer (500 ml) | | |
|---|---|---|
| 200 mM NiSO₄ | 52.56 g | 1× = 50 mM |

TABLE 2

| 8× Binding Buffer (1 Liter) | | |
|---|---|---|
| 40 mM Imidazole | 2.72 g | 1× = 5 mM |
| 4M NaCl | 237 g | 500 mM |
| 160 mM Tris | 19.36 | 20 mM |

Mix together and pH to 7.9 with HCl.

TABLE 3

| 8× Wash Buffer (500 mL) | | |
|---|---|---|
| 480 mM Imidazole | 16.3 g | 1× = 60 mM |
| 4M NaCl | 117 g | 500 mM |
| 160 mM Tris | 19.68 | 20 mM |

Mix together and pH to 7.9 with HCl. If using urea drop the imidazole to 20 mM. 8X=160.

TABLE 4

| 4× Elution Buffer (500 mL) | | |
|---|---|---|
| 4M Imidazole | 136 g | 1× = 1M |

TABLE 4-continued

| 4× Elution Buffer (500 mL) | | |
|---|---|---|
| 2M NaCl | 58.44 | 0.5M |
| 80 mM Tris | 4.84 | 20 mM |

Mix together and pH to 7.9 with HCL

TABLE 5

| 4× Strip Buffer (500 mL) | | |
|---|---|---|
| 0.4M EDTA | 74.4 g | 1× = 100 mM |
| 2M NaCl | 58.44 | 500 mM |
| 80 mM | Tris 4.84 | 20 mM |

Mix together. Add NaOH pellets to get pH to 8.0 so that EDTA will dissolve. Then adjust pH to 7.9.

A chimeric protein containing both SipD and SipB proteins was produced (FIG. 13; SEQ ID NO: 7), together with SipA protein. This method allows a cGMP facility to produce these proteins with one fermentor run, significantly reducing the protein purification costs.

The chimeric protein is administered to a subject as described herein and, as a result, a protective immune response is elicited in the subject.

Example 5: In Vivo Vaccine Evaluation

Food safety is a health issue that affects not only the United States, but the rest of the world. Today, the globalization of the food chain means tainted beef in the United States could cause illness or death halfway across the globe. In fact, *Salmonella* tainted beef may be the most significant challenge facing ranchers and the beef industry today. From the dinner plate to the pet food bowl, *Salmonella* contamination is a top story demanding solutions. A broad and wide immunization policy with an effective vaccine that works regardless of serovar across multiple species would allow the elimination of *Salmonella* as an endemic disease on farms across the States.

The currently available *Salmonella* vaccines protect against a limited number of serovars and thus lack the impact and economic strength to change farm behavior, so subclinical infections continue to have a negative effect on both producer and consumer. By having a single vaccine that is cross-protective against virtually all *Salmonella*, would eliminate disease, morbidity and mortality for both animals and people.

The specific objective was to demonstrate homologous protection of the vaccine against *S. enterica* serovar *Typhimurium* in a calf model. The proof of concept experiments were conducted in mice and the data with one component of the vaccine demonstrated that this vaccine can reduce bacterial shedding of a heterologous serotype. S. Newport, to the serotype from which the subunit vaccine was derived.

Materials and Methods

Protein Purification. The recombinant proteins, SIF and S2F, were constructed as per the standard protocol (Chen, X., et al. *Infect Inmun.* 2015; 83 (1): 292-299; Choudhari, S. P., et al. *Protein Sci.* 2013; 22 (5): 666-670; Choudhari, S. P., et al, *J Pharm Sci.* 2014. doi: 10.1002/jps.24047). Briefly, for SIF, the sipD-sipB gene fusion was cloned into pET9d which is kanamycin resistant and the gene for the cognate SipB chaperone SicA, was cloned into pACYC which is chloramphenicol resistant. The plasmids were co-transformed into *E. coli* Tuner (DE3) for expression. The bacteria are grown at 37° C. to an $A_{600}$ of 0.8 at which point IPTG was added to induce protein expression. After three hours, the bacteria were collected by centrifugation, lysed, and the inclusion bodies collected again in the pellet. The pellet was resuspended in IMAC binding buffer containing 6M urea. The solution was clarified by centrifugation and loaded onto a nickel charged IMAC column. The column was washed and the protein eluted. The eluted protein was passed over a Q column with the eluted protein slowly refolded by step dialysis into IMAC binding buffer with 0.05% (v/v) N,N-dimethyldodecylamine N-oxide (LDAO). The solution was passed again over an IMAC column to remove the chaperone which was released from the complex by the detergent. Fractions were collected and the final dialysis step exchanges the proteins into phosphate buffered saline (PBS) containing LDAO which is required to maintain solubility of the proteins and has a GRAS (Generally Regarded As Safe) Profile. Furthermore, this detergent confers a significant degree of thermal stability to this class of proteins as well (Chen, X. et al., 2015). The proteins were concentrated to 5 mg/ml and stored at −80° C. For S2F, the sseB-sseC gene fusion has been cloned into pET9d which is kanamycin resistant and the gene for the cognate SseC chaperone SscA, was cloned into pACYC which is chloramphenicol resistant. The plasmids were co-transformed into *E. coli* Tuner (DE3) for expression. The remainder of the purification is the same as SIF.

Vaccine Preparation. The adjuvant for preparing purified subunit vaccine is monophosphoryl lipid A (MPL; Sigma Chemical Co.) combined with dipalmitoylphosphatidyl choline (DPPC) in a 4:1 molar ratio. Two milligrams of each protein were combined with ~2 mg of Alhydrogel (AH) and allowed to bind for one hour with gentle shaking at room temperature. Currently, binding isotherms are being performed to determine the actual optimal Alhydrogel ratio per unit protein. MPL (100 μg) was added to the formulation with a final vaccine formulation containing 1 ml. A live attenuated ΔSPI-1/2 *S. typhimurium* strain was used for the positive control and grown overnight at 37° C. with shaking, collected by centrifugation, washed and finally resuspended in PBS at $1\times10^7$ cfu/ml. The negative control was PBS only.

Large Animal Efficacy Study. The calf experiments are performed at the Veterinary and Biomedical Research Center (VBRC), Manhattan, KS by Kelly Lechtenberg, DVM, Ph.D. All animals used are approved by the VBRC Institutional Animal Care and Use Committee, Holstein steers, 200 pounds, are obtained from one of the commercial Holstein calf vendors that can assure study candidates are *Salmonella*-free and have not been given any commercial vaccine against *Salmonella* by pre-screening fecal samples and by control of vaccination and management protocols. Fecal samples are obtained prior to the experiment to ensure no *Salmonella* is detectable. Calves are housed individually in indoor pens. Calves are initially fed twice daily (bottle or pail) with a commercial milk replacer appropriate for the age of the calves. As calves start to consume non-medicated dry feed, milk feeding is reduced to once daily to enhance dry feed consumption. Calves will have access to fresh water ad libitum.

Vaccination. Two groups (n=10/group) of calves are vaccinated subcutaneously three times on days 0, 14, and 28, with either PBS or the SIF+S2F (2 mg each) adsorbed to AH then admixed with 100 μg MPL (see above vaccine formulation). The ΔSPI-1/2 strain (2 ml) is fed to another group of 10 calves on days 0 and 28 by mixing with milk. Groups of ten were chosen as this is the minimum number that is required to obtain significant results in both the challenge experiment and the immunology determinations. In addition, performance of a power analysis evidences that a number of 10 animals per group are enough to discern a difference of ~20% in protective capacity.

Sample collection. Blood is drawn at 0, 14, 28, and 42 to obtain serum (from clotted blood) and peripheral blood mononuclear cells (PBMCs, from Heparinized blood) via standard procedures. Fecal samples and saliva are collected at these times as well. One mg of fecal contents is suspended in I ml of PBS containing sodium azide and the suspension shaken vigorously by vortexer for 15 min. The suspension is clarified and the supernatant is frozen al-80° C. until analyzed by ELISA. Although total IgA can be detected, it is possible that rectal secretions need to be obtained to detect antigen-specific IgA in fecal samples. As an alternative, six cotton-tipped applicators are used to collect saliva from under the tongue and around the check. The saliva is transferred via centrifugation into a 50 ml conical tube from the applicators that are in a 15 ml conical tube with a hole in the bottom. Kinetics of serum IgG and fecal IgA titers are determined. The Immunological Core of the KVI performs the ELISAs to determine the antigen-specific IgG and IgA levels, (Martinez-Becerra, F. J, et al. *Infect Immun*, 2013a; 81 (12) 4470-4477; Martinez-Becerra, F. J., et al. *Vaccine*, 2013b; 31 (24): 2667-2672). The preliminary data provided for the protective efficacy of SseB in calves included determination of the kinetics of serum IgG and fecal IgA production by the calves. Peripheral blood mononuclear cells (PBMCs) separated from blood samples are incubated in plates with SipD, SipB, SseB, and SseC to assess the frequency of antibody secreting cells. Similarly, after stimulation with the antigens, the cells and supernatant are assessed for IFNγ and IL-17 levels via flow cytometry and ELISA respectively. Statistical analysis is performed using Graphpad prism and FlowJo software. Differences among treatments are analyzed using ANOVAs and t-tests. A P value <0.05 is considered significant for all analysis.

Go/No Go to Challenge. Based on previous immunological results, the titers for the anti-SipD, SipB, SseB, SseC-specific IgG were at least $10^3$-$10^4$ ELISA units/ml with IgA units being 10 ELISA units/ml. Background was less than 25 EU/ml. Similarly, there should be 100 IgG and 50 IgA antibody secreting cells (ASC) specifically directed against each antigen per $10^6$ peripheral blood mononuclear cells (PBMCs). In a previous calf experiment (see challenge results below), an increase in IFNγ and IL-17 levels were observed. If these conditions are not met, another vaccination is performed. Three vaccinations stimulate a complete immune response since maximal IgG and IgA titers were detected at the sampling associated with day 48 vaccination.

*S. typhimurium* Challenge. Calves are challenged orally with $1.2\times10^7$ *S. typhimurium* SL1344 ($Sm^2$) which is the inoculum required to result in *Salmonella*-positive peripheral lymph nodes (Brown, T. R., et al. *Journal of Food Protection*. 2015; 78 (3): 573-578). The bacteria are grown at VBRC at 37° C. overnight with shaking, collected by centrifugation, washed and finally resuspended in PBS at $1,2\times10$ cfu/ml. A sample of the final inoculum is subjected to dilution plating to determine the actual final inoculum (prior to challenge, growth, manipulation and dilution is performed until the dilution plating is within 1% error on 3 consecutive trials). Upon challenge, weight loss is monitored over a seven day period (Day 0 and Day 7). Temperature is monitored in the morning (daily). Health scores are determined (Snider, T. A., et al. *Vet Microbiol*. 2014; 170

(1-2): 65-72) in the morning (daily). Fecal shedding is monitored over a seven day period by resuspending 1 mg of fecal matter in 10 ml of PBS by vortexing, and serial dilutions plated onto TSB+streptomycin (50 µg/ml). At the end of the study, the calves are euthanized, necropsies performed, and the *Salmonella* burden assessed in the matter of the gastrointestinal tract (rumen, cecum, colon, and rectum) and in the major lymph nodes (mesenteric, subiliac, popliteal, and superficial cervical) as per standard published methods (Brown, T. R. et al. 2015).

Go/No Go to heterologous challenge and Phase II. The *Salmonella* carriage in the lymph nodes of the vaccinated calves should be reduced by 90-100% from unvaccinated animals. The shedding should be eliminated in the vaccinated calves earlier relative to the unvaccinated as well as the level of shedding should be reduced at least four logs.

Results

Figure 14:
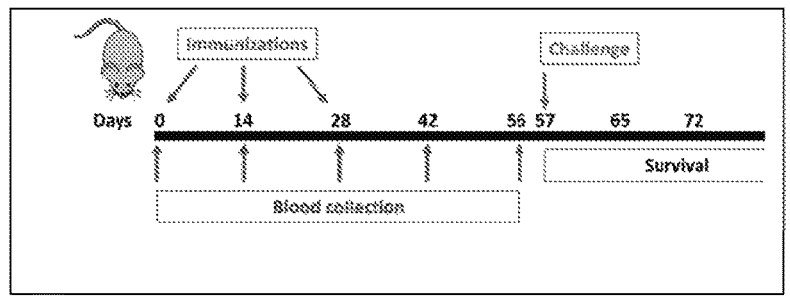
FIG. 14 is a schematic representation of an experimental plan for mouse experiments.
Figures 15A, 15B, 15C, 15D:
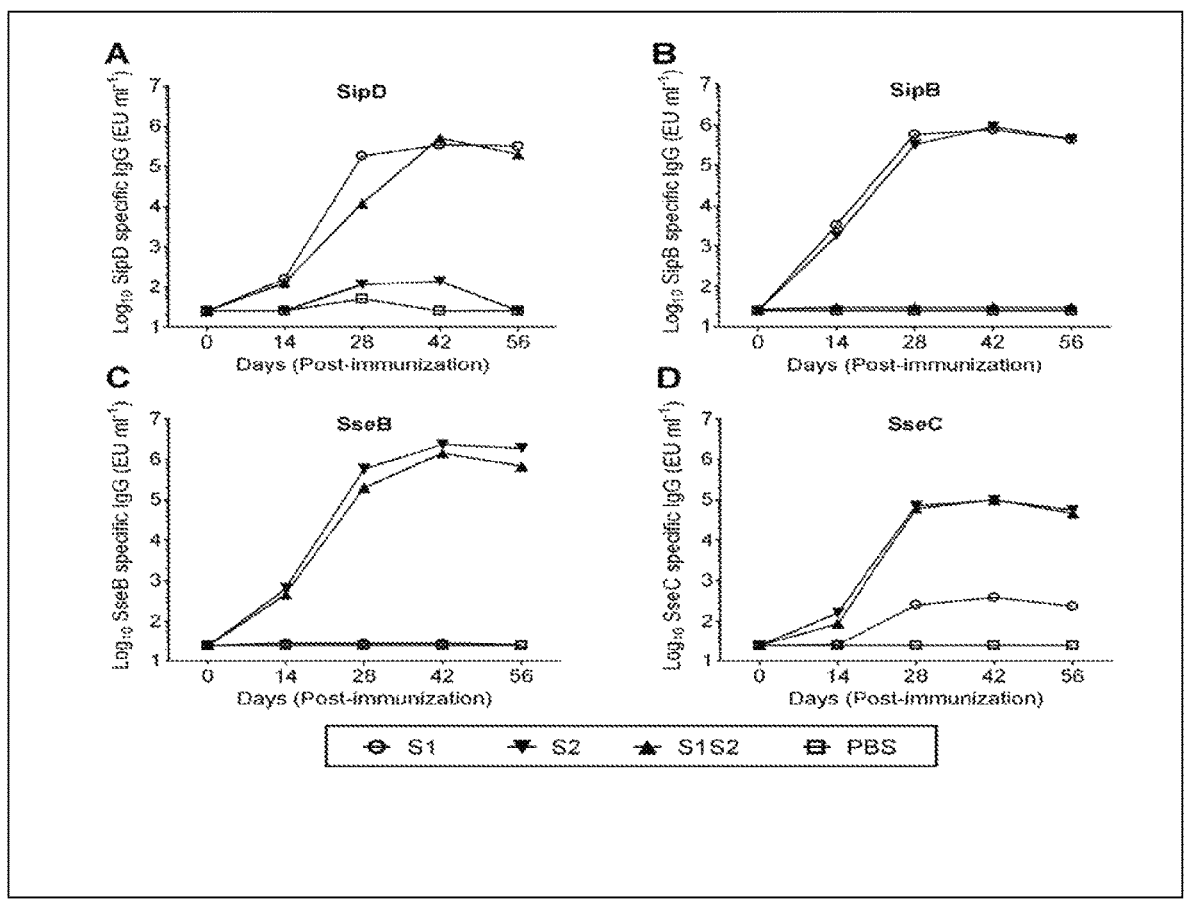
FIGS. 15A-15D are graphs showing the kinetics of serum IgG response against SipD, SipB, SseB, and SscC. Serum samples from blood collected at days 0, 14, 28, 42, and 56 were analyzed for their titers against the four proteins that are part of the SIF (SipD and B) and S2F (SseB and C). All the titers are from pooled serum from the group of mice tested (N=10).

SipD and SipB alone or together did not provide complete protective efficacy. SseB, in contrast, does provide some protection (see calf data, FIG. 17). *Salmonella* fusion proteins SIF and S2F were made recombinantly in *E. coli*. Five fotal groups (n=15) of female BALB/c mice were used with the experimental plan depicted in FIG. 14. Pour groups were vaccinated intramuscularly three times with 100 µl of vaccine formulation containing the following: 1) 20 ag SIF+50 µg monophosphoryl lipid A (MPL)+50 µg Alhydrogel (AHI); 2) 20 µg S2F+50 µg MPL+50 µg AH: 3) 20 µg SIF+20 µg S2F+50 µg MPL+50 µg AH; 4) buffer only (phosphate-buffered saline; PBS). Finally, one group was vaccinated on day 28 with a live-attenuated strain of either *S. typhimurium* or *S. Enteritidis*. Blood samples (processed to obtain serum) from all the mice were collected at day 0, 14, 18, 42 and 56 during the course of vaccination. Anti-SipB, -SipD, -SseB, and -SseC IgG serum titers were determined along with the Ig A titers from fecal samples. No IgA response against any of the antigens was detected in fecal samples. This result was observed with parenteral immunization using the *Shigella* IpaD-IpaB Fusion. Mice that were vaccinated with SIF elicited a robust anti-SipB and -SipD IgG response (FIGS. 15A-15D). Interestingly, a modest amount of cross-reactivity was detected with the S2F group. Likewise, mice vaccinated with S2F elicited a robust anti-SseB and -SseC IgG responses. Samples from mice vaccinated with live-attenuated strain were not tested since, in the past, this strain has elicited a response to LPS and not to these antigens.

At day 56 post-immunization, five mice from each immunized group were euthanized to collect spleen and bone marrow. Single cell suspensions obtained from spleens and bone marrows were stimulated with the four antigens and the frequency of IgG antigen-secreting cells (ASC) in the spleen and bone marrow was determined by ELISpot assay (FIGS. 16A, 16B). Mice groups immunized with SIF demonstrated high frequencies of anti-SipB IgG ASC, but more modest frequencies of anti-SipD IgG ASC in bone marrow. The groups immunized with S2F had high frequencies of anti-SseB IgG ASC and moderate frequencies of anti-SseC IgG ASC in bone marrow. No profound IgG ASC against the four antigens was detected in the spleens from mice vaccinated with the live-attenuated strain or PBS.

On day 56, the remaining mice were challenged with $2\times10^8$ cfu ($10LD_{50}$) of S. *Typhimurium* SL1344 (wild-type) or $8\times10^7$ cfu ($10LD_{50}$) of *S. enteritidis* (wild-type). In this model, mice do not exhibit symptoms of gastroenteritis but they do develop a systemic typhoid-like illness with death as the endpoint. Mice that were immunized with the live-attenuated strain showed 80% and 70% survival in case of *S. typhimurium* and *S. enteritidis* challenges, respectively (FIGS. 16A, 16B). This was an expected observation since the protection afforded to the mice by this strain is serotype specific. Although the SIF and $2F vaccine formulations conferred no protection, the combination of SIF+S2F showed an encouraging survival pattern with 60% protection against lethal challenges regardless of serovar used for challenge. The fact that the current vaccine formulation confers significant protection before even optimizing the vaccine formulation is promising.

Previously, SseB was tested in a calf study to assess protective efficacy. Calves were vaccinated subcutaneously (n=6) with 2 mg SseB (a component of $2F) admixed with 50 µg dmLT (double mutant labile toxin from enterotoxigenic *E. coli*) or PBS (n=6). These twelve calves were challenged with S. Newport. Each set of calves exhibited a significant increase in body temperature by day 2 indicating a successful S. Newport infection (FIG. 17, top). Except for days 2 and 3, the trend of the temperatures exhibited by the SseB+dmLT group was lower than those of the PBS group. Fecal shedding was also monitored. On day 1 both groups shed ~10° S. Newport/gram of feces (FIG. 17, middle). Over time, there was an increase in shedding from the sham-vaccinated calves and the majority of these calves continued shedding up to $10^5$ CPU/gram for most of the study. The sham-vaccinated animals were only able to achieve baseline levels on day 10. In contrast, the calves vaccinated with SseB+dmL.T did not exhibit increased fecal shedding of S. Newport. Instead, day 2 and 3 shedding was maintained near $10^4$ with a drop to baseline levels at day 4. The lack of shedding on day 4 coincided with the return of normal rectal temperatures on this day. Although a slight increase was seen on day 5 for 2 animals, the remaining days saw baseline shedding levels. When the ten day total shedding was calculated, the vaccine efficacy in reducing S. Newport shedding was significant. The total ten day bacterial shedding for the group vaccinated with SseB+dmLT was not only lower than the sham-vaccinated group, but the variation over the ten day period was less than one log unit which is consistent with no effective increase in shedding over time (FIG. 17, bottom). Thus, the SseB+dmLT vaccine reduced disease severity relative to the control group and reduced shedding from the initial time point.

CONCLUSION

Vaccine prevention of *Salmonella* infections in livestock reduces time and money spent treating infections and reduces development of antibiotic resistance. There will be, in turn, less need for segregation and/or culling of sick animals that would be reservoirs for pathogen spread. The technology described herein for the production of this vaccine is one that is of use globally. Subunit vaccines are among the safest and there is no stigma like that encountered with genetically modified agricultural products. Thus, not only can this vaccine be used within the US, but it can be marketed for sale abroad.

S1fusion ((Nde-SipD-Sal-SipB-Xho) in pET28; SEQ ID NO: 13):

```
ATGGGCAGCAGCCATCATCATCATCATCACAGCAGCGGCCTGGTGCCGCGCGGCAG
CCATATGCTTAATATTCAAAATTATTCCGCTTCTCCTCATCCGGGGATCGTTGCCGAA
CGGCCGCAGACTCCCTCGGCGAGCGAGCACGTCGAGACTGCCGTGGTACCGTCTAC
CACAGAACATCGCGGTACAGATATCATTTCATTATCGCAGGCGGCTACTAAAATCCA
CCAGGCACAGCAGACGCTGCAGTCAACGCCACCGATCTCTGAAGAGAATAATGACG
AGCGCACGCTGGCGCGCCAGCAGTTGACCAGCAGCCTGAATGCGCTGGCGAAGTCC
GGCGTGTCATTATCCGCAGAACAAAATGAGAACCTGCGGAGCGCGTTTTCTGCGCCG
ACGTCGGCCTTATTTAGCGCTTCGCCTATGGCGCAGCCGAGAACAACCATTTCTGAT
GCTGAGATTTGGGATATGGTTTCCCAAAATATATCGGCGATAGGTGACAGCTATCTG
GGCGTTTATGAAAACGTTGTCGCAGTCTATACCGATTTTTATCAGGCCTTCAGTGAT
ATTCTTTCCAAATGGGAGGCTGGTTATTACCAGGTAAGGACGGTAATACCGTTAAG
CTAGATGTTACCTCACTCAAAAATGATTTAAACAGTTTAGTCAATAAATATAATCAA
ATAAACAGTAATACCGTTTTATTTCCAGCGCAGTCAGGCAGCGGCGTTAAAGTAGCC
ACTGAAGCGGAAGCGAGACAGTGGCTCAGTGAATTGAATTTACCGAATAGCTGCCT
GAAATCTTATGGATCCGGTTATGTCGTCACCGTTGATCTGACGCCATTACAAAAAAT
GGTTCAGGATATTGATGGTTTAGGCGCGCCGGGAAAAGACTCAAAACTCGAAATGG
ATAACGCCAAATATCAAGCCTGGCAGTCGGGTTTTAAAGCGCAGGAAGAAAATATG
AAAACCACATTACAGACGCTGACGCAAAAATATAGCAATGCCAATTCATTGTACGA
CAACCTGGTAAAAGTGCTGAGCAGTACGATAAGTAGCAGCCTGGAAACCGCCAAAA
GCTTCCTGCAAGGAGTCGACATGGTAAATGACGCAAGTAGCATTAGCCGTAGCGGA
TATACCCAAAATCCGCGCCTCGCTGAGGCGGCTTTTGAAGGCGTTCGTAAGAACACG
GACTTTTTAAAAGCGGCGGATAAAGCTTTTAAAGATGTGGTGGCAACGAAAGCGGG
CGACCTTAAAGCCGGAACAAAGTCCGGCGAGAGCGCTATTAATACGGTGGGTCTAA
AGCCGCCTACGGACGCCGCCCGGGAAAAACTCTCCAGCGAAGGGCAATTGACATTA
CTGCTTGGCAAGTTAATGACCCTACTGGGCGATGTTTCGCTGTCTCAACTGGAGTCT
CGTCTGGCGGTATGGCAGGCGATGATTGAGTCACAAAAAGAGATGGGGATTCAGGT
ATCGAAAGAATTCCAGACGGCTCTGGGAGAGGCTCAGGAGGCGAAGGATTCTCTATG
AAGCCAGTATCAAAAAGACGGATACCGCCAAGAGTGTTTATGACGCTGCGACCAAA
AAACTGACGCAGGCGCAAAATAAATTGCAATCGCTGGACCCGGCTGACCCCGGCTA
TGCACAAGCTGAAGCCGCGGTAGAACAGGCCGGAAAAGAAGCGACAGAGGCGAAA
GAGGCCTTAGATAAGGCCACGGATGCGACGGTTAAAGCAGGCACAGACGCCAAAG
CGAAAGCCGAGAAAGCGGATAACATTCTGACCAAATTCCAGGGAACGGCTAATGCC
GCCTCTCAGAATCAGGTTTCCCAGGGTGAGCAGGATAATCTGTCAAATGTCGCCCGC
CTCACTATGCTCATGGCCATGTTTATTGAGATTGTGGGCAAAAATACGGAAGAAAGC
CTGCAAAACGATCTTGCGCTTTTCAACGCCTTGCAGGAAGGGCGTCAGGCGGAGAT
GGAAAAGAAATCGGCTGAATTCCAGGAAGAGACGCGCAAAGCCGAGGAAACGAAC
CGCATTATGGGATGTATCGGGAAAGTCCTCGGCGCGCTGCTAACCATTGTCAGCGTT
GTGGCCGCTGTTTTTACCGGTGGGGCGAGTCTGGCGCTGGCTGCGGTGGGACTTGCG
GTAATGGTGGCCGATGAAATTGTGAAGGCGGCGACGGGAGTGTCGTTTATTCAGCA
GGCGCTAAACCCGATTATGGAGCATGTGCTGAAGCCGTTAATGGAGCTGATTGGCA
AGGCGATTACCAAAGCGCTGGAAGGATTAGGCGTCGATAAGAAAACGGCAGAGAT
GGCCGGCAGCATTGTTGGTGCGATTGTCGCCGCTATTGCCATGGTGGCGGTCATTGT
GGTGGTCGCAGTTGTCGGGAAAGGCGCGGCGGCGAAACTGGGTAACGCGCTGAGCA
AAATGATGGGCGAAACGATTAAGAAGTTGGTGCCTAACGTGCTGAAACAGTTGGCG
CAAAACGGCAGCAAACTCTTTACCCAGGGGATGCAACGTATTACTAGCGGTCTGGG
TAATGTGGGTAGCAAGATGGGCCTGCAAACGAATGCCTTAAGTAAAGAGCTGGTAG
GTAATACCCTAAATAAAGTGGCGTTGGGCATGGAAGTCACGAATACCGCAGCCCAG
TCAGCCGGTGGTGTTGCCGAGGGCGTATTTATTAAAAATGCCAGCGAGGCGCTTGCT
GATTTTATGCTCGCCCGTTTTGCCATGGATCAGATTCAGCAGTGGCTTAAACAATCC
GTAGAAATATTTGGTGAAAACCAGAAGGTAACGGCGGAACTGCAAAAAGCCATGTC
TTCTGCGGTACAGCAAAATGCGGATGCTTCGCGTTTTATTCTGCGCCAGAGTCGCGC
ATAA
```

S1F (SEQ ID NO: 14)
MGSSHHHHHHSSGLVPRGSHMLNIQNYSASPHPGIVAERPQTPSASEHVETAVVPST
TEHRGTDIISLSQAATKIHQAQQTLQSTPPISEENNDERTLARQQLTSSLNALAKSGVSLS
AEQNENLRSAFSAPTSALFSASPMAQPRTTISDAEIVVDMVSQNISAIGDSYLGVYENVVA
VYTDFYQAFSDILSKMGGWLLPGKDGNTVKLDVTSLKNDLNSLVNKYNQINSNTVLFP
AQSGSGVKVATEAEARQWLSELNLPNSCLKSYGSGYVVTVDLTPLQKMVQDIDGLGAP
GKDSKLEMDNAKYQAWQSGFKAQEENMKTTLQTLTQKYSNANSLYDNLVKVLSSTISS
SLETAKSFLQGVDMVNDASSISRSGYTQNPRLAEAAFEGVRKNTDFLKAADKAFKDVV
ATKAGDLKAGTKSGESAINTVGLKPPTDAAREKLSSEGQLTLLLGKLMTLLGDVSLSQL
ESRLAVWQAMIESQKEMGIQVSKEFQTALGEAQEATDLYEASIKKTDTAKSVYDAATK
KLTQAQNKLQSLDPADPGYAQAEAAVEQAGKEATEAKEALDKATDATVKAGTDAKA
KAEKADNILTKFQGTANAASQNQVSQGEQDNLSNVARLTMLMAMFIEIVGKNTEESLQ
NDLALFNALQEGRQAEMEKKSAEFQEETRKAEETNRIMGCIGKVLGALLTIVSVVAAVF
TGGASLALAAVGLAVMVADEIVKAATGVSFIQQALNPIMEHVLKPLMELIGKAITKALE
GLGVDKKTAEMAGSIVGAIVAAIAMVAVIVVVAVVGKGAAAKLGNALSKMMGETIKK
LVPNVLKQLAQNGSKLFTQGMQRITSGLGNVGSKMGLQTNALSKELVGNTLNKVALG
MEVTNTAAQSAGGVAEGVFIKNASEALADFMLARFAMDQIQQWLKQSVELFGENQKVT
AELQKAMSSAVQQNADASRFILRQSRA

S2fusion ((Nde-SseB-Sac-SseC-Bam) in pET15; SEQ ID NO: 15)
```
ATGGGCAGCAGCCATCATCATCATCATCACAGCAGCGGCCTGGTGCCGCGCGGC
AGCCATATGCTCTTCAGGAAACATCTTATGGGGAAGTCAAAACCCTATTGTGTTTAAA
AATAGCTTCGGCGTCAGCAACGCTGATACCGGGAGCCAGGATGACTTATCCCAGCA
AAATCCGTTTGCCAAGGGTATGGTGTTTGCTTATTCTCCTTATGGTTATTCAGGCT
ATCGCAAATAATAAATTTATTGAAGTCCAGAAGAACGCTGAACGTGCCAGAAATAC
```

-continued

```
CCAGGAAAAGTCAAATGAGATGGATGAGGTGATTGCTAAAGCAGCCAAAGGGGAT
GCTAAAACCAAAGAGGAGGTGCCTGAGGATGTAATTAAATACATGCGTGATAATGG
TATTCTCATCGATGGTATGACCATTGATGATTATATGGCTAAATATGGCGATCATGG
GAAGCTGGATAAAGGTGGCCTACAGGCGATCAAAGCGGCTTTGGATAATGACGCCA
ACCGGAATACCGATCTTATGAGTCAGGGGCAGATAACAATTCAAAAAATGTCTCAG
GAGCTTAACGCTGTCCTTACCCAACTGACAGGGCTTATCAGTAAGTGGGGGGAAATT
TCCAGTATGATAGCGCAGAAAACGTACTCACCGCGGATGAATCGAATTCACAGTAA
TAGCGACAGCGCCGCAGGAGTAACCGCCTTAACACATCATCACTTAAGCAATGTCA
GTTGCGTTTCCTCGGGTTCGCTGGGAAAGCGCCAGCATCGTGTGAATTCTACTTTTG
GCGATGGCAACGCCGCGTGTCTGCTATCCGGGAAAATTAGTCTTCAGGAGGCAAGC
AATGCGTTGAAGCAACTGCTTGATGCCGTACCCGGAAATCATAAGCGTCCATCATTG
CCTGACTTTTTGCAGACCAATCCCGCGGTTTTATCAATGATGATGACGTCATTAATAC
TCAACGTCTTTGGTAATAACGCTCAATCGTTATGCCAACAGCTTGAGCGGGCAACTG
AGGTGCAAAATGCATTACGTAATAAGCAGGTAAAGGAGTATCAGGACGCAGATCCAG
AAAGCGATAGAGCAGGAGGATAAAGCGCGTAAAGCGGGTATTTTTGGCGCTATTTT
TGACTGGATTACCGGCATATTTGAAACCGTGATTGGCGCCTTAAAAGTTGTGGAAGG
TTTTCTGTCCGGAAATCCCGCAGAAATGGCTAGCGGCGTAGCTTATATGGCCGCAGG
TTGTGCAGGAATGGTTAAAGCCGGAGCCGAAACGGCAATGATGTGCGGTGCTGACC
ACGATACCTGTCAGGCAATTATTGACGTGACAAGTAAGATTCAATTTGGTTGTGAAG
CCGTCGCGCTGGCACTGGATGTTTTCCAGATTGGCCGTGCTTTTATGGCGACGAGAG
GTTTATCTGGCGCAGCTGCAAAAGTGCTTGACTCCGGTTTTGGCGAGGAAGTGGTTG
AGCGTATGGTAGGTGCAGGGGAAGCAGAAATAGAGGAGTTGCTGAAAAGTTTGGC
GAAGAAGTGAGCGAAAGTTTTTCCAAACAATTTGAGCCGCTTGAACGTGAAATGGC
TATGGCGAATGAGATGGCAGAGGAGGCTGCCGAGTTTTCTCGTAACGTAGAAAATA
ATATGACGCGAAGCGCGGGAAAAAGCTTTACGAAAGAGGGGGTGAAAGCCATGGC
AAAAGAAGCGGCAAAAGAAGCCCTGGAAAAATGTGTGCAAGAAGGTGGAAAGTTC
CTGTTAAAAAAATTCCGTAATAAAGTTCTCTTCAATATGTTCAAAAAAATCCTGTAT
GCCTTACTGAGGGATTGTTCATTTAAAGGCTTACAGGCTATCAGATGTGCAACCGAG
GGCGCCAGTCAGATGAATACTGGCATGGTTAACACAGAAAAAGCGAAGATCGAAAA
GAAAATAGAGCAATTAATAACTCAGCAACGGTTTCTGGATTTCATAATGCAACAAA
CAGAAAACCAGAAAAGATAGAACAAAAACGCTTAGAGGAGCTTTATAAGGGGAG
CGGTGCCGCGCTTAGAGATGTATTAGATACCATTGATCACTATAGTAGCGTTCAGGC
GAGAATAGCTGGCTATCGCGCTTAA
```

S2F (SEQ ID NO: 16):
```
MGSSHHHHHHSSGLVPRGSHMSSGNILWGSQNPIVFKNSFGVSNADTGSQDDLSQQ
NPFAEGYGVLLILLMVIQAIANNKFIEVQKNAERARNTQEKSNEMDEVIAKAAKGDAKT
KEEVPEDVIKYMRDNGILIDGMTIDDYMAKYGDHGKLDKGGLQAIKAALDNDANRNT
DLMSQGQITIQKMSQELNAVLTQLTGLISKWGEISSMIAQKTYSPRMNRIHSNSDSAAGV
TALTHHHLSNVSCVSSGSLGKRQHRVNSTFGDGNAACLLSGKISLQEASNALKQLLDAV
PGNHKRPSLPDFLQTNPAVLSMMMTSLILNVFGNNAQSLCQQLERATEVQNALRNKQV
KEYQEQIQKAIEQEDKARKAGIFGAIFDWITG1FETVIGALKVVEGFLSGNPAEMASGVA
YMAAGCAGMVKAGAETAMMCGADHDTCQAIIDVTSKIQFGCEAVALALDVFQIGRAF
MATRGLSGAAAKVLDSGFGEEVVERMVGAGEAEIEELAEKFGEEVSESFSKQFEPLERE
MAMANEMAEEAAEFSRNVENNMTRSAGKSFTKEGVKAMAKEAAKEALEKCVQEGGK
FLLKKFRNKVLFNMFKKILYALLRDCSFKGLQAIRCATEGASQMNTGMVNTEKAKIEK
KIEQLITQQRFLDFIMQQTENQKKIEQKRLEELYKGSAALRDVLDTIDHYSSVQARIAG
YRA
```

*

-continued

Salmonella typhimurium pathogenicity island 2, partial sequence (SEQ ID NO: 24):
```
M N R I H S N S D S A A G V T A L T H H H L S N V S C V S S G S L G
K R Q H R V N S T F G D G N A A C L L S G K I S L Q E A S N A L K Q
L L D A V P G N H K R P S L P D F L Q T N P A V L S M M M T S L I L
N V F G N N A Q S L C Q Q L E R A T E V Q N A L R N K Q V K E Y Q
E Q I Q K A I E Q E D K A R K A G I F G A I F D W I T G I F E T V I G
A L K V V E G F L S G N P A E M A S G V A Y M A A G C A G M V K A
G A E T A M M C G A D H D T C Q A I I D V T S K I Q F G C E A V A L
A L D V F Q I G R A F M A T R G L S G A A A K V L D S G F G E E V V
E R M V G A G E A E I E E L A E K F G E E V S E S F S K Q F E P L E R
E M A M A N E M A E E A A E F S R N V E N N M T R S A G K S F T K
E G V K A M A K E A A K E A L E K C V Q E G G K F L L K K F R N K
V L F N M F K K I L Y A L L R D C S F K G L Q A I R C A T E G A S Q
M N T G M V N T E K A K I E K K I E Q L I T Q Q R F L D F I M Q Q T
E N Q K K I E Q K R L E E L Y K G S G A A L R D V L D T I D H Y S S
V Q A R I A G Y R A -
```

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art. Such changes and modifications are encompassed within the spirit of this invention as defined by the claims.

---

SEQUENCE LISTING

```
Sequence total quantity: 25
SEQ ID NO: 1           moltype = AA   length = 593
FEATURE                Location/Qualifiers
source                 1..593
                       mol_type = protein
                       organism = Salmonella enterica
SEQUENCE: 1
MVNDASSISR SGYTQNPRLA EAAFEGVRKN TDFLKAADKA FKDVVATKAG DLKAGTKSGE    60
SAINTVGLKP PTDAAREKLS SEGQLTLLLG KLMTLLGDVS LSQLESRLAV WQAMIESQKE   120
MGIQVSKEFQ TALGEAQEAT DLYEASIKKT DTAKSVYDAA TKKLTQAQNK LQSLDPADPG   180
YAQAEAAVEQ AGKEATEAKE ALDKATDATV KAGTDAKAKA EKADNILTKF QGTANAASQN   240
QVSQGEQDNL SNVARLTMLM AMFIEIVGKN TEESLQNDLA LFNALQEGRQ AEMEKKSAEF   300
QEETRKAEET NRIMGCIGKV LGALLTIVSV VAAVFTGSAS LALAAVGLAV MVADEIVKAA   360
TGVSFIQQAL NPIMEHVLKP LMELIGKAIT KALEGLGVDK KTAEMAGSIV GAIVAAIAMV   420
AVIVVVAVVG KGAAAKLGNA LSKMMGETIK KLVPNVLKQL AQNGSKLFTQ GMQRITSGLG   480
NVGSKMGLQT NALSKELVGN TLNKVALGME VTNTAAQSAG GVAEGVFIKN ASEALADFML   540
ARFAMDQIQQ WLKQSVEIFG ENQKVTAELQ KAMSSAVQQN ADASRFILRQ SRA          593

SEQ ID NO: 2           moltype = DNA   length = 1782
FEATURE                Location/Qualifiers
source                 1..1782
                       mol_type = genomic DNA
                       organism = Salmonella enterica
SEQUENCE: 2
ttatgcgcga ctctggcgca gaataaaacg cgaagcatcc gcattttgct gtaccgcaga      60
agacatggct ttttgcagtt ccgccgttac cttctggttt tcaccaaata tttctacgga     120
ttgtttaagc cactgctgaa tctgatccat ggcaaaacgg gcgagcataa aatcagcaag     180
cgcctcgctg gcatttttaa taaatacgcc ctcggcaaca ccaccggctg actgggctgc     240
ggtattcgtg acttccatgc ccaacgccac tttatttagg gtattaccta ccagctcttt     300
acttaaggca ttcgtttgca ggcccatctt gctacccaca ttacccagac cgctagtaat     360
acgttgcatc ccctgggtaa agagtttgct gccgttttgc gccaactgtt tcagcacgtt     420
aggcaccaac ttcttaatcg tttcgcccat cattttgctc agcgcgttac ccagtttcgc     480
cgccgcgcct ttcccgacaa ctgcgaccac cacaatgacc gccaccatgg caatagcggc     540
gacaatcgca ccaacaatgc tgccggccat ctctgccgtt ttcttatcga cgcctaatcc     600
ttccagcgct ttggtaatcg ccttgccaat cagctccatt aacggcttca gcacatgctc     660
cataatcggg tttagcgcct gctgaataaa cgacactccc gtcgccgcct tcacaatttc     720
atcggccacc attaccgcaa gtcccaccgc agccagcgcc agactcgccc caccggtaaa     780
aacagcggcc acaacgctga caatggttag cagcgcgccg aggactttcc cgatacatcc     840
cataatgcgg ttcgtttcct cggctttgcg cgtctcttcc tggaattcag ccgattttct     900
ttccatctcc gcctgacgcc cttcctgcaa ggcgttgaaa agcgcaagat cgttttgcag     960
gctttcttcc gtattttgc ccacaatctc aataaacatg gccatgagca tagtgaggcg    1020
ggcgacattt gacagattat cctgctcacc ctgggaaacc tgattctgag aggcggcatt    1080
agccgttccc tggaatttgg tcagaatgtt atccgctttc tcggctttcg ctttggcgtc    1140
tgtgcctgct ttaaccgtcg catccgtggc cttatctaag gcctctttcg cctctgtcgc    1200
ttcttttccg gcctgttcta ccgcggcttc agcttgtgca tagccggggt cagccgggtc    1260
cagcgattgc aatttatttt gcgcctgcgt cagttttttg gtcgcagcgt cataaacact    1320
cttggcggta tccgtctttt tgatactggc ttcatagaga tccgtccgtc cctgagcctc    1380
tcccagagcc gtctggaatt cttcgatac ctgaatcccc atctcttttt gtgactcaat    1440
catcgcctgc cataccgcca gacgagactc cagttgagac agcgaaacat cgcccagtag    1500
ggtcattaac ttgccaagca gtaatgtcaa ttgcccttcg ctggagagtt ttccgggcc    1560
ggcgtccgta ggcggcttta gacccaccgt attaatagcg ctctcgccgg actttgttcc    1620
ggctttaagg tcgcccgctt tcgttgccac cacatcttta aaagctttat ccgccgcttt    1680
```

```
taaaaagtcc gtgttcttac gaacgccttc aaaagccgcc tcagcgaggc gcggattttg   1740
ggtatatccg ctacggctaa tgctacttgc gtcatttacc at                     1782

SEQ ID NO: 3           moltype = AA   length = 339
FEATURE                Location/Qualifiers
source                 1..339
                       mol_type = protein
                       organism = Salmonella enterica
SEQUENCE: 3
MLNIQNYSAS PHPGIVAERP QTPSASEHAE IAVVPSTTEH RGTDIISLSQ AATKIQQAQQ    60
TLQSTPPISE ENNDERTLAR QQLTSSLNAL AKSGVSLSAE QNENLRSTFS ARRRPYLALR   120
LWPARTTISD AEIWDMVSQN ISAIGDSYLG VYENVVAVYT DFYQAFSDIL SKMGGWLSPG   180
KDGNTIKLNV DSLKSEISSL INKYTQINKN TILFPSQTGS GMTTATKAEA EQWIKELNLP   240
DSCLKASGSG YVVLVDTGPL SKMVSDLNGI GSGSALELDN AKYQAWQSGF KAQEENLKTT   300
LQTLTQKYSN ANSLYDNLVK VLSSTISSSL ETAKSFLQG                          339

SEQ ID NO: 4           moltype = DNA   length = 1020
FEATURE                Location/Qualifiers
source                 1..1020
                       mol_type = genomic DNA
                       organism = Salmonella enterica
SEQUENCE: 4
atgcttaata ttcaaaatta ttccgcttct cctcatccgg ggatcgttgc cgaacggccg    60
cagactcctt cggcgagcga gcacgccgag attgccgtgg taccgtctac cacagaacat   120
cgcggcacag atatcatttc attatcgcag gcggctacta aaatccagca ggcacagcag   180
acgcagt caacgccacc gatttctgaa gagaatactg acgacgcac gctggcgcgc       240
caacagttga ccagcagcct gaatgcgctg gcgaagtccg gcgtgtcatt atccgcagaa   300
caaaatgaga acctgcggag cacgtttcct gcgcgacgtc ggcctatt agcgcttcgc    360
ctatggccga cgaacaac catttctgat gctgagattt gggatatggt ttcccaaaat    420
atatcggcga taggtgacag ctacctgggc gtttatgaaa acgttgtcgc agtctatacc   480
gattttatc aggccttcag tgatattctt tccaaaatgg gaggctggtt atcgcctggt    540
aaggatggaa ataccattaa gctaaatgtt gactcactta aaagtgaaat aagtagttta   600
attaataaat acactcaaat aaataaaaat acgatttat ttccctcgca aactggcagc    660
ggaatgacaa cagcaacgaa agcggaagct gagcagtgga ttaaagaatt gaatttaccg   720
gacagctgtc taaaggcgtc tggttctggt tatgtcgtac tggtggatac ggggccactg   780
agcaaaatgg ttagcgatct taatggaata ggatcgggtt cagcccttga actggataac   840
gccaaatatc aagcctggca gtcgggtttt aaagcacagg aagaaaatct gaaaaccaca   900
ttacagacgc tgacgcaaaa atatagcaat gccaattcat gtacgacaa cctggtaaaa   960
gtgctgagca gtacgataag tagcagcctg gaaaccgcca aagcttcct gcaaggataa  1020

SEQ ID NO: 5           moltype = AA   length = 196
FEATURE                Location/Qualifiers
source                 1..196
                       mol_type = protein
                       organism = Salmonella enterica
SEQUENCE: 5
MSSGNILWGS QNPIVFKNSF GVSNADTGSQ DDLSQQNPFA EGYGVLLILL MVIQAIANNK    60
FIEVQKNAER ARNTQEKSNE MDEVIAKAAK GDAKTKEEVP EDVIKYMRDN GILIDGMTID   120
DYMAKYGDHG KLDKGGLQAI KAALDNDANR NTDLMSQGQI TIQKMSQELN AVLTQLTGLI   180
SKWGEISSMI AQKTYS                                                   196

SEQ ID NO: 6           moltype = DNA   length = 591
FEATURE                Location/Qualifiers
source                 1..591
                       mol_type = genomic DNA
                       organism = Salmonella enterica
SEQUENCE: 6
atgtcttcag gaaacatctt atggggaagt caaaaccta ttgtgtttaa aaatagcttc     60
ggcgtcagca acgctgatac cgggagccag gatgacttat cccagcaaaa tccgtttgcc   120
gaagggtatg gtgttttgct tattctcctt atggttattc aggctatcgc aaataataaa   180
tttattgaag tccagaagaa cgctgaacgt gccagaaata cccaggaaaa gtcaaatgag   240
atggatgagg tgattgctaa agcagccaaa ggggatgcta aaaccaaaga ggaggtgcct   300
gaggatgtaa ttaaatacat gcgtgataat ggtattctca tcgatggtat gaccattgat   360
gattatatgg ctaaatatgg cgatcatggg aagctgataa aaggtggcct acaggcgatc   420
aaagcggctt tggataatga cgccaaccgg aataccgatc ttatgagtca ggggcagata   480
acaattcaaa aaatgtctca ggagcttaac gctgtcctta cccaactgac agggcttatc   540
agtaagtggg gggaaatttc cagtatgata gcgcagaaaa cgtactcatg a            591

SEQ ID NO: 7           moltype = AA   length = 934
FEATURE                Location/Qualifiers
REGION                 1..934
                       note = Description of Artificial Sequence: Synthetic
                       SipD-SipB chimera
source                 1..934
                       mol_type = protein
                       organism = synthetic construct
SEQUENCE: 7
MLNIQNYSAS PHPGIVAERP QTPSASEHAE IAVVPSTTEH RGTDIISLSQ AATKIQQAQQ    60
TLQSTPPISE ENNDERTLAR QQLTSSLNAL AKSGVSLSAE QNENLRSTFS ARRRPYLALR   120
```

-continued

```
LWPARTTISD AEIWDMVSQN ISAIGDSYLG VYENVVAVYT DFYQAFSDIL SKMGGWLSPG  180
KDGNTIKLNV DSLKSEISSL INKYTQINKN TILFPSQTGS GMTTATKAEA EQWIKELNLP  240
DSCLKASGSG YVVLVDTGPL SKMVSDLNGI GSGSALELDN AKYQAWQSGF KAQEENLKTT  300
LQTLTQKYSN ANSLYDNLVK VLSSTISSSL ETAKSFLQGV DMVNDASSIS RSGYTQNPRL  360
AEAAFEGVRK NTDFLKAADK AFKDVVATKA GDLKAGTKSG ESAINTVGLK PPTDAAREKL  420
SSEGQLTLLL GKLMTLLGDV SLSQLESRLA VWQAMIESQK EMGIQVSKEF QTALGEAQEA  480
TDLYEASIKK TDTAKSVYDA ATKKLTQAQN KLQSLDPADP GYAQAEAAVE QAGKEATEAK  540
EALDKATDAT VKAGTDAKAK AEKADNILTK FQGTANAASQ NQVSQGEQDN LSNVARLTML  600
MAMFIEIVGK NTEESLQNDL ALFNALQEGR QAEMEKKSAE FQEETRKAEE TNRIMGCIGK  660
VLGALLTIVS VVAAVFTGGA SLALAAVGLA VMVADEIVKA ATGVSFIQQA LNPIMEHVLK  720
PLMELIGKAI TKALEGLGVD KKTAEMAGSI VGAIVAAIAM VAVIVVVAVV GKGAAAKLGN  780
ALSKMMGETI KKLVPNVLKQ LAQNGSKLFT QGMQRITSGL GNVGSKMGLQ TNALSKELVG  840
NTLNKVALGM EVTNTAAQSA GGVAEGVFIK NASEALADFM LARFAMDQIQ QWLKQSVEIF  900
GENQKVTAEL QKAMSSAVQQ NADASRFILR QSRA                             934

SEQ ID NO: 8           moltype = DNA  length = 2817
FEATURE                Location/Qualifiers
misc_feature           1..2817
                       note = Description of Artificial Sequence: Synthetic
                        nucleic acidsequence encoding SipD-SipB chimera
source                 1..2817
                       mol_type = other DNA
                       organism = synthetic construct
SEQUENCE: 8
atgcttaata ttcaaaatta ttccgcttct cctcatccgg ggatcgttgc cgaacggccg  60
cagactccct cggcgagcga gcacgtcgag actgccgtgg taccgtctac cacagaacat  120
cgcggtacag atatcatttc attatcgcag gcggctacta aaatccacca ggcacagcag  180
acgctgcagt caacgccacc gatctctgaa gagaataatg acgagcgcac gctggcgcgc  240
cagcagttga ccagcagcct gaatgcgctg gcgaagtccg gcgtgtcatt atccgcagaa  300
caaaatgaga acctgcggag cgcgttttct gcgccgacgt cggccttatt tagcgcttcg  360
cctatggcgc agccgagaac aaccatttct gatgctgaga tttgggatat ggtttcccaa  420
aatatatcgg cgataggtga cagctatctg ggcgtttatg aaaacgttgt cgcagtctat  480
accgattttt atcaggcctt cagtgatatt ctttccaaaa tgggaggctg gttattacca  540
ggtaaggacg gtaataccgt taagctagat gttacctcac tcaaaaatga tttaaacagt  600
ttagtcaata aatataatca aataaacagt aataccgttt tatttccagc gcagtcaggc  660
agcggcgtta aagtagccac tgaagcggaa gcgagacagt ggctcagtga attgaattta  720
ccgaatagct gcctgaaatc ttatggatcc ggttatgtcg tcaccgttga tctgacgcca  780
ttacaaaaaa tggttcagga tattgatggt ttaggcgcgc cgggaaaaga ctcaaaactc  840
gaaatggata acgccaaata tcaagcctgg cagtcgggtt ttaaagcgca ggaagaaaat  900
atgaaaacca cattacagac gctgacgcaa aaatatagca atgccaattc attgtacgac  960
aacctggtaa aagtgctgag cagtacgata agtagcagcc tggaaaccgc caaaagcttc  1020
ctgcaaggag tcgacatggt aaatgacgca agtagcatta gccgtagcgg atatacccaa  1080
aatccgcgcc tcgctgaggc ggcttttgaa ggcgttcgta agaacacgga ctttttaaaa  1140
gcggcggata aagcttttaa agatgtggtg gcaacgaaag cgggcgacct taaagccgga  1200
acaaagtccg gcgagagcgc tattaatacg gtgggtctaa agccgcctac ggacgccgcc  1260
cgggaaaaac tctccagcga agggcaattg acattactgc ttggcaagtt aatgacccta  1320
ctgggcgatg tttcgctgtc tcaactggag tctcgtctgg cggtatggca ggcgatgatt  1380
gagtcacaaa aagagatggg gattcaggta tcgaaagaat tccagacggc tctgggagag  1440
gctcaggagg cgacggatct ctatgaagcc agtatcaaaa agacggatac cgccaagagt  1500
gtttatgacg ctgcgaccaa aaaactgacg caggcgcaaa ataaattgca atcgctggac  1560
ccggctgacc ccggctatgc acaagctgaa gccgcggtag aacaggccgg aaaagaagcg  1620
acagaggcga aagaggcctt agataaggcc acggatgcga cggttaaagc aggcacagac  1680
gccaaagcga aagccgagaa agcggataac attctgacca aattccaggg aacggctaat  1740
gccgcctctc agaatcaggt ttcccagggt gagcaggata atctgtcaaa tgtcgcccgc  1800
ctcactatgc tcatggccat gtttattgag attgtgggca aaaatacgga agaaagcctg  1860
caaaacgatc ttgcgctttt caacgccttg caggaagggc gtcaggcgga gatggaaaag  1920
aaatcggctg aattccagga agagacgcgc aaagccgagg aaacgaaccg cattatggga  1980
tgtatcggga aagtcctcgg cgcgctgcta accattgtca gcgttgtggc cgctgttttt  2040
accggtgggg cgagtctggc gctggctgcg gtgggacttg cggtaatggt ggccgatgaa  2100
attgtgaagg cggcgacggg agtgtcgttt attcagcagg cgctaaaccc gattatggag  2160
catgtgctga agccgttaat ggagctgatt ggcaaggcga ttaccaaagc gctggaagga  2220
ttaggcgtcg ataagaaaac ggcagagatg gccggcagca ttgttggtgc gattgtcgcc  2280
gctattgcca tggtggcggt cattgtggtg gtcgcagttg tcgggaaagg cgcggcggcg  2340
aaactgggta acgcgctgag caaaatgatg ggcgaaacga ttaagaagtt ggtgcctaac  2400
gtgctgaaac agttggcgca aaacggcagc aaactcttta cccaggggat gcaacgtatt  2460
actagcggtc tgggtaatgt gggtagcaag atgggcctgc aaacgaatgc cttaagtaaa  2520
gagctggtag gtaataccct aaataaagtg gcgttgggca tggaagtcac gaataccgca  2580
gcccagtcag ccggtggtgt tgccgagggc gtatttatta aaaatgccag cgaggcgctt  2640
gctgatttta tgctcgcccg ttttgccatg gatcagattc agcagtggct taaacaatcc  2700
gtagaaatat ttggtgaaaa ccagaaggta acggcggaac tgcaaaaagc catgtcttct  2760
gcggtacagc aaaatgcgga tgcttcgcgt tttattctgc gccagagtcg cgcataa     2817

SEQ ID NO: 9           moltype =   length =
SEQUENCE: 9
000

SEQ ID NO: 10          moltype =   length =
SEQUENCE: 10
000
```

| SEQ ID NO: 11 | moltype = length = |
|---|---|
| SEQUENCE: 11 | |
| 000 | |

| SEQ ID NO: 12 | moltype = length = |
|---|---|
| SEQUENCE: 12 | |
| 000 | |

| SEQ ID NO: 13 | moltype = DNA length = 2877 |
|---|---|
| FEATURE | Location/Qualifiers |
| misc_feature | 1..2877 |
| | note = Description of Artificial Sequence: Synthetic polynucleotide |
| source | 1..2877 |
| | mol_type = other DNA |
| | organism = synthetic construct |

SEQUENCE: 13

```
atgggcagca gccatcatca tcatcatcac agcagcggcc tggtgccgcg cggcagccat   60
atgcttaata ttcaaaatta ttccgcttct cctcatccgg ggatcgttgc cgaacggccg  120
cagactccct cggcgagcga gcacgtcgag actgccgtgg taccgtctac acagaacat   180
cgcggtacag atatcatttc attatcgcag gcggctacta aaatccacca ggcacagcag  240
acgctgcagt caacgccacc gatctctgaa gagaataatg acgagcgcac gctggcgcgc  300
cagcagttga ccagcagcct gaatgcgctg gcgaagtccg gcgtgtcatt atccgcagaa  360
caaaatgaga acctgcggag cgcgtttct gcgccgacgt cggccttatt tagcgcttcg   420
cctatgcggc agccgagaac aaccatttct gatgctgaag tttgggatat ggtttcccaa  480
aatatatcgg cgataggtga cagctatctg ggcgtttatg aaaacgttgt cgcagtctat  540
accgattttt atcaggcctt cagtgatatt ctttccaaaa tgggaggctg ttattacca   600
ggtaaggacg gtaataccgt taagctagat gttacctcac tcaaaaatga tttaaacagt  660
ttagtcaata aatataatca aataaacagt aataccgttt tatttccagc gcagtcaggc  720
agcggcgtta aagtagccac tgaagcggaa gcgagacagt ggctcagtga attgaattta  780
ccgaatagct gcctgaaatc ttatggatcc ggttatgtcg tcaccgttga tctgacgcca  840
ttacaaaaaa tggttcagga tattgatggt ttaggcgcgc cggggaaaga ctcaaaactc  900
gaaatggata acgccaaata tcaagcctgg cagtcgggtt ttaaagcgca ggaagaaat   960
atgaaaacca cattacgagac gctgacgcaa aaatatgaca atgccaattc attgtacgac 1020
aacctggtaa aagtgctgag cagtacgata agtagcagcc tggaaccgc caaaagcttc  1080
ctgcaaggag tcgacatggt aaatgacgca agtagcatta gccgtagcgg atatacccaa  1140
aatccgcgcc tcgctgaggc ggcttttgaa ggcgttcgta gaacacgga cttttaaaa   1200
gcggcggata aagctttaa agatgtggtg gcaacgaaag cgggcgacct taagccggca  1260
acaaagtccg gcgagagcgc tattaatacg gtgggtctaa agccgcctac ggacgccgcc  1320
cgggaaaaac tctccagcga agggcaattg acattactgc ttggcaagtt aatgacccta  1380
ctgggcgatg tttcgctgtc tcaactggag tctcgtctgg cggtatggca ggcgatgatt  1440
gagtcacaaa aagagatggg gattcaggta tcgaaagaat tccagcagga tctggagag   1500
gctcaggagg cgacggatct ctatgaagcc agtatcaaaa agacggatac cgccaagagt  1560
gtttatgacg ctgcgaccaa aaaactgacg caggcgcaaa ataaattgca atcgctggac  1620
ccggctgacc ccggctatgc acaagctgaa gccgcgtag aacaggccgg aaaagaagcg  1680
acagaggcga aagaggcctt agataaggcc acggatgcga cggttaaagc aggcacagac  1740
gccaaagcga aagccgagaa agcggataac attctgacca aattccaggg aacggcaat   1800
gccgcctctc agaatcaggt ttcccagggt gagcaggata tctgtcaaa tgtcgcccgc  1860
ctcactatgc tcatgccat gtttattgag attgtgggca aaaatacgga gaaagcctg   1920
caaaacgatc ttgcgctttt caacgccttg caggaaggc gtcaggcgga gatggaaaag  1980
aaatcggctg aattccagga agagacgcgc aaagccgagg aaacgaaccg cattatggga  2040
tgtatcggga aagtcctcgg cgcgctgcta accattgtca gcgttgtggc cgctgttttt  2100
accggtgggg cgagtctggc gctggctgcg gtgggacttg cggtaatggt ggccgatgaa  2160
attgtgaagg cggcgacggg agtgtcgttt attcagcagg cgctaaaccc gattatggag  2220
catgtgctga gccgttaat ggagctgatt gcaaggcga ttaccaaagc gctgaagga   2280
ttaggcgtcg ataagaaaac ggcagagatg gccggcagca ttgttggtgc gattgtcgcc  2340
gctattgcca tggtggcggt cattgtggtg gtcgcagttg tcgggaaagg cgcggcggcg  2400
aaactgggta acgcgctgag caaaatgatg gcgaaacga ttaagaagtt ggtgcctaac   2460
gtgctgaaac agttggcgca aaacggcagc aaactcttta cccagggat gcaacgtatt  2520
actagcggtc tgggtaatgt gggtagcaag atgggcctgc aaacgaatgc cttaagtaaa  2580
gagctggtag gtaatacct aaataaagtg cgttgggca tggaagtcac gaataccgca  2640
gcccagtcag ccggtggtgt tgccgagggc gtatttatta aaatgccag cgaggcgctt  2700
gctgatttta tgctcgcccg tttttgccatg gatcagattc cgcagtggct taaacaatcc  2760
gtagaaatat ttggtgaaaa ccagaaggta acgcgggaac tgcaaaaagc catgtcttct  2820
gcggtacagc aaaaatgcgga tgcttcgcgt tttattctgc gccagagtcg cgcataa    2877
```

| SEQ ID NO: 14 | moltype = AA length = 958 |
|---|---|
| FEATURE | Location/Qualifiers |
| REGION | 1..958 |
| | note = Description of Artificial Sequence: Synthetic polypeptide |
| source | 1..958 |
| | mol_type = protein |
| | organism = synthetic construct |

SEQUENCE: 14

```
MGSSHHHHHH SSGLVPRGSH MLNIQNYSAS PHPGIVAERP QTPSASEHVE TAVVPSTTEH   60
RGTDIISLSQ AATKIHQAQQ TLQSTPPISE ENNDERTLAR QQLTSSLNAL AKSGVSLSAE  120
QNENLRSAFS APTSALFSAS PMAQPRTTIS DAEIWDMVSQ NISAIGDSYL GVYENVVAVY  180
```

```
TDFYQAFSDI  LSKMGGWLLP  GKDGNTVKLD  VTSLKNDLNS  LVNKYNQINS  NTVLFPAQSG  240
SGVKVATEAE  ARQWLSELNL  PNSCLKSYGS  GYVVTVDLTP  LQKMVQDIDG  LGAPGKDSKL  300
EMDNAKYQAW  QSGFKAQEEN  MKTTLQTLTQ  KYSNANSLYD  NLVKVLSSTI  SSSLETAKSF  360
LQGVDMVNDA  SSISRSGYTQ  NPRLAEAAFE  GVRKNTDFLK  AADKAFKDVV  ATKAGDLKAG  420
TKSGESAINT  VGLKPPTDAA  REKLSSEGQL  TLLLGKLMTL  LGDVSLSQLE  SRLAVWQAMI  480
ESQKEMGIQV  SKEFQTALGE  AQEATDLYEA  SIKKTDTAKS  VYDAATKKLT  QAQNKLQSLD  540
PADPGYAQAE  AAVEQAGKEA  TEAKEALDKA  TDATVKAGTD  AKAKAEKADN  ILTKFQGTAN  600
AASQNQVSQG  EQDNLSNVAR  LTMLMAMFIE  IVGKNTEESL  QNDLALFNAL  QEGRQAEMEK  660
KSAEFQEETR  KAEETNRIMG  CIGKVLGALL  TIVSVVAAVF  TGGASLALAA  VGLAVMVADE  720
IVKAATGVSF  IQQALNPIME  HVLKPLMELI  GKAITKALEG  LGVDKKTAEM  AGSIVGAIVA  780
AIAMVAVIVV  VAVVGKGAAA  KLGNALSKMM  GETIKKLVPN  VLKQLAQNGS  KLFTQGMQRI  840
TSGLGNVGSK  MGLQTNALSK  ELVGNTLNKV  ALGMEVTNTA  AQSAGGVAEG  VFIKNASEAL  900
ADFMLARFAM  DQIQQWLKQS  VEIFGENQKV  TAELQKAMSS  AVQQNADASR  FILRQSRA    958

SEQ ID NO: 15            moltype = DNA  length = 2109
FEATURE                  Location/Qualifiers
misc_feature             1..2109
                         note = Description of Artificial Sequence: Synthetic
                         polynucleotide
source                   1..2109
                         mol_type = other DNA
                         organism = synthetic construct
SEQUENCE: 15
atgggcagca gccatcatca tcatcatcac agcagcggcc tggtgccgcg cggcagccat    60
atgtcttcag gaaacatctt atggggaagt caaacccca ttgtgtttaa aaatagcttc     120
ggcgtcagca acgctgatac cgggagccag gatgacttat cccagcaaaa tccgtttgcc    180
gaagggtatg gtgttttgct tattctcctt atggttattc aggctatcgc aaataataaa    240
tttattgaag tccagaagaa cgctgaacgt gccagaaata cccaggaaaa gtcaaatgag    300
atggatgagg tgattgctaa agcagccaaa ggggatgcta aaaccaaaga ggaggtgcct    360
gaggatgtaa ttaaatacat gcgtgataat ggtattctca tgggtgatac cattgataac    420
gattatatgg ctaaatatgg cgatcatggg aagctggata aaggtggcct acaggcgatc    480
aaaagcggct tggataatga cgccaaccgg ataccgatc ttatgagtca ggggcagata    540
acaattcaaa aaatgtctca ggagcttaac gctgtcctta cccaactgac agggcttatc    600
agtaagtggg gggaaatttc cagtatgata gcgcagaaaa cgtactcacc gcgcatgaat    660
cgaattcaca gtaatagcga cagcgccgca ggagtaaccg ccttaacaca tcatcactta    720
agcaatgtca gttgcgtttc ctcggggtcg ctgggaaagc gccagcatcg tgtgaattct    780
acttttggcg atggcaacgc cgcgtgtctg ctatccggga aaattagtct tcaggaggca    840
agcaatgcgt tgaagcaact gcttgatgcc gtacccggaa atcataagcg tccatcattg    900
cctgacttt tgcagaccaa tcccggtt tatcaatga tgatgacgtc attaatactc          960
aacgtctttg gtaataacgc tcaatcgtta tgccaacagc ttgagcgggc aactgaggtg    1020
caaaatgcat acgtaataa gcaggtaaag gagtatcagg agcagatcca aaagcgata     1080
gagcaggagg ataaagcgcg taaagcgggt atttttggcg ctattttga ctggattacc      1140
ggcatatttg aaaccgtgat tggcgcctta aaagttgtga aaggtttttct gtccggaaat    1200
cccgcagaaa tggctagcgg cgtagcttat atggccgcag gttgtgcagg aatggttaaa    1260
gccggagccg aaacgcaat gatgtgcggt gctgaccacg ataccgtca ggcaattatt      1320
gacgtgacaa gtaagattca atttggttgt gaagccgtcg cgctggcact ggatgttttc    1380
cagattggcc gtgcttttat ggcgacgaga ggtttatctg gcgcagctgc aaaagtgctt    1440
gactccggtt ttggcgagga agtggttgag cgtatgggtag gtgcagggga gcagaaaata    1500
gaggagttgg ctgaaaagtt tggcgaagaa gtgagcgaaa gttttcccaa acaatttgag    1560
ccgcttgaac gtgaaatggc tatggcgaat gagatgcag aggaggctgc cgagttttct     1620
cgtaacgtag aaaataatat gacgcgaagc gcgggaaaaa gctttacgaa agggggcgtg    1680
aaagccatgg caaaagaagc ggcaaaagaa gccctggaaa aatgtgtgca agaaggtgga    1740
aagttcctgt taaaaaaatt ccgtaataaa gttctcttca atatgttcaa aaaaatcctg    1800
tatgccttac tgagggattg ttcatttaaa ggcttacagg ctatcagatg tgcaaccgag    1860
ggcgccagtc agatgaatac tggcatggtt aacacagaaa aagcgaagat cgaaaagaaa    1920
atagagcaat taataactca gcaacggttt ctggatttca taatgcaaca aacagaaaac    1980
cagaaaaaga tagaacaaaa acgctagag gagctttata aggggagcgg tgccgcgctt    2040
agagatgtat tagataccat tgatcactat agtagcgttc aggcgagaat agctggctat    2100
cgcgcttaa                                                            2109

SEQ ID NO: 16            moltype = AA  length = 702
FEATURE                  Location/Qualifiers
REGION                   1..702
                         note = Description of Artificial Sequence: Synthetic
                         polypeptide
source                   1..702
                         mol_type = protein
                         organism = synthetic construct
SEQUENCE: 16
MGSSHHHHHH  SSGLVPRGSH  MSSGNILWGS  QNPIVFKNSF  GVSNADTGSQ  DDLSQQNPFA  60
EGYGVLLILL  MVIQAIANNK  FIEVQKNAER  ARNTQEKSNE  MDEVIAKAAK  GDAKTKEEVP  120
EDVIKYMRDN  GILIDGMTID  DYMAKYGDHG  KLDKGGLQAI  KAALDNDANR  NTDLMSQGQI  180
TIQKMSQELN  AVLTQLTGLI  SKWGEISSMI  AQKTYSPRMN  RIHSNSDSAA  GVTALTHHHL  240
SNVSCVSSGS  LGKRQHRVNS  TFGDGNAACL  LSGKISLQEA  SNALKQLLDA  VPGNHKRPSL  300
PDFLQTNPAV  LSMMMTSLIL  NVFGNNAQSL  CQQLERATEV  QNALRNKQVK  EYQEQIQKAI  360
EQEDKARKAG  IFGAIFDWIT  GIFETVIGAL  KVVEGFLSGN  PAEMASGVAY  MAAGCAGMVK  420
AGAETAMMCG  ADHDTCQAII  DVTSKIQFGC  EAVALALDVF  QIGRAFMATR  GLSGAAAKVL  480
DSGFGEEVVE  RMVGAGEAEI  EELAEKFGEE  VSESFSKQFE  PLEREMAMAN  EMAEEEAAEFS  540
RNVENNMTRS  AGKSFTKEGV  KAMAKEAAKE  ALEKCVQEGG  KFLLKKFRNK  VLFNMFKKIL  600
```

```
YALLRDCSFK GLQAIRCATE GASQMNTGMV NTEKAKIEKK IEQLITQQRF LDFIMQQTEN    660
QKKIEQKRLE ELYKGSGAAL RDVLDTIDHY SSVQARIAGY RA                      702

SEQ ID NO: 17           moltype =   length =
SEQUENCE: 17
000

SEQ ID NO: 18           moltype =   length =
SEQUENCE: 18
000

SEQ ID NO: 19           moltype =   length =
SEQUENCE: 19
000

SEQ ID NO: 20           moltype =   length =
SEQUENCE: 20
000

SEQ ID NO: 21           moltype =   length =
SEQUENCE: 21
000

SEQ ID NO: 22           moltype =   length =
SEQUENCE: 22
000

SEQ ID NO: 23           moltype = DNA   length = 1455
FEATURE                 Location/Qualifiers
source                  1..1455
                        mol_type = genomic DNA
                        organism = Salmonella typhimurium
SEQUENCE: 23
atgaatcgaa ttcacagtaa tagcgacagc gccgcaggag taaccgcctt aacacatcat    60
cacttaagca atgtcagttg cgtttcctcg ggttcgctgg gaaagcgcca gcatcgtgtg   120
aattctactt ttggcgatgg caacgccgcg tgtctgctat ccgggaaaat tagtcttcag   180
gaggcaagca atgcgttgaa gcaactgctt gatgccgtac ccggaaatca taagcgtcca   240
tcattgcctg acttttgtca gaccaatccc gcggttttat caatgatgat gacgtcatta   300
atactcaacg tctttggtaa taacgctcaa tcgttatgcc aacagcttga gcgggcaact   360
gaggtgcaaa atgcattacg taataagcag gtaaaggagt atcaggagca gatccagaaa   420
gcgatagagc aggaggataa agcgcgtaaa gcgggtattt ttggcgctat ttttgactgg   480
attaccggca tatttgaaac cgtgattggc gccttaaaag ttgtggaagg ttttctgtcc   540
ggaaatcccg cagaaatggc tagcggcgta gcttatatgg ccgcaggttg tgcaggaagca  600
gttaaagccg gagccgaaac ggcaatgatg tgccggtgctg accacgatac ctgtcaggca   660
attattgacg tgacaagtaa gattcaattt ggttgtgaag ccgtcgcgct ggcactggat   720
gttttccaga ttggccgtgc ttttatgcg acgagaggtt tatctggcgc agctgcaaaa    780
gtgcttgact ccggttttgg cgaggaagtg gttgagcgta tggtaggtgc aggggaagca   840
gaaatagagg agttggctga aaagtttggc gaagaagtga gcgaaagttt ttccaaacaa   900
tttgagccgc ttaacgtgaa aatggctatg gcgaatgaga tggcagagga ggctgccgag   960
ttttctcgta acgtagaaaa taatatgacg cgaagcgcgg gaaaaagctt tacgaaagag  1020
gggggtgaaag ccatggcaaa agaagcggca aaagaagccc tggaaaaatg tgtgcaagaa  1080
ggtggaaagt tcctgttaaa aaaattccgt aataaagttc tcttcaatat gttcaaaaaa  1140
atcctgtatg ccttactgag ggattgttca tttaaaggct acaggctat cagatgtgca   1200
accgagggcg ccagtcagat gaatactggc atggttaaca cagaaaaagc gaagatcgaa   1260
aagaaaatag agcaattaat aactcagcaa cggttctgg atttcattat gcaacaaaca   1320
gaaaaccaga aaaagataga acaaaaacgc ttagaggagc tttataaggg gagcggtgcc   1380
gcgcttagag atgtattaga taccattgat cactatagta gcgttcaggc gagaatagct   1440
ggctatcgcg cttaa                                                  1455

SEQ ID NO: 24           moltype = AA   length = 484
FEATURE                 Location/Qualifiers
source                  1..484
                        mol_type = protein
                        organism = Salmonella typhimurium
SEQUENCE: 24
MNRIHSNSDS AAGVTALTHH HLSNVSCVSS GSLGKRQHRV NSTFGDGNAA CLLSGKISLQ    60
EASNALKQLL DAVPGNHKRP SLPDFLQTNP AVLSMMMTSL ILNVFGNNAQ SLCQQLERAT   120
EVQNALRNKQ VKEYQEQIQK AIEQEDKARK AGIFGAIFDW ITGIFETVIG ALKVVEGFLS   180
GNPAEMASGV AYMAAGCAGM VKAGAETAMM CGADHDTCQA IIDVTSKIQF GCEAVALALD   240
VFQIGRAFMA TRGLSGAAAK VLDSGFGEEV VERMVGAGEA EIEELAEKFG EEVSESFSKQ   300
FEPLEREMAM ANEMAEEAE FSRNVENNMT RSAGKSFTKE GVKAMAKEAA KEALEKCVQE   360
GGKFLLKKFR NKVLFNMFKK ILYALLRDCS FKGLQAIRCA TEGASQMNTG MVNTEKAKIE   420
KKIEQLITQQ RFLDFIMQQT ENQKKIEQKR LEELYKGSGA ALRDVLDTID HYSSVQARIA   480
GYRA                                                               484

SEQ ID NO: 25           moltype = AA   length = 9
FEATURE                 Location/Qualifiers
REGION                  1..9
                        note = Description of Artificial Sequence: Synthetic peptide
```

```
source                  1..9
                        mol_type = protein
                        organism = synthetic construct
SEQUENCE: 25
CYGGRGDTP                                                                    9
```

What is claimed:

1. A method of protecting against or treating an infection in a subject at risk of, or infected by a *Salmonella* serovar, comprising administering to the subject a composition comprising *Salmonella* pathogenicity island 1 (SPI-1) and *Salmonella* pathogenicity island 2 (SPI-2) extracellular protein; a physiologically acceptable carrier; wherein the SPI-1 extracellular protein comprises SipD or SipB; wherein the SPI-2 extracellular protein comprises SseB; and wherein the composition is administered in an amount so as to elicit an immune response to a *Salmonella* serovar SPI-1 and/or SPI-2 antigen in the subject.

2. The method of claim 1, wherein the composition further comprises SseC.

3. The method of claim 1, wherein the *Salmonella* serovar is a *Salmonella enterica* serovar.

4. The method of claim 1, wherein the composition further comprises an adjuvant.

* * * * *